United States Patent
Al-Ali et al.

(10) Patent No.: US 11,717,210 B2
(45) Date of Patent: Aug. 8, 2023

(54) DEPTH OF CONSCIOUSNESS MONITOR INCLUDING OXIMETER

(71) Applicant: Masimo Corporation, Irvine, CA (US)

(72) Inventors: Ammar Al-Ali, San Juan Capistrano, CA (US); Yassir Kamel Abdul-Hafiz, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 43 days.

(21) Appl. No.: 16/741,541

(22) Filed: Jan. 13, 2020

(65) Prior Publication Data

US 2020/0253498 A1 Aug. 13, 2020

Related U.S. Application Data

(63) Continuation of application No. 15/389,285, filed on Dec. 22, 2016, now Pat. No. 10,531,811, which is a
(Continued)

(51) Int. Cl.
| | |
|---|---|
| *A61B 5/369* | (2021.01) |
| *A61B 5/00* | (2006.01) |
| *A61B 5/1455* | (2006.01) |
| *A61B 5/291* | (2021.01) |
| *A61B 5/374* | (2021.01) |
| *A61B 5/16* | (2006.01) |

(52) U.S. Cl.
CPC ............ *A61B 5/369* (2021.01); *A61B 5/0006* (2013.01); *A61B 5/1455* (2013.01); *A61B 5/14551* (2013.01); *A61B 5/14552* (2013.01); *A61B 5/14553* (2013.01); *A61B 5/165* (2013.01); *A61B 5/291* (2021.01); *A61B 5/374* (2021.01); *A61B 5/4821* (2013.01); *A61B 5/6814* (2013.01); *A61B 5/742* (2013.01); *A61B 5/6803* (2013.01); *A61B 5/6833* (2013.01); *A61B 2562/164* (2013.01)

(58) Field of Classification Search
None
See application file for complete search history.

(56) References Cited

U.S. PATENT DOCUMENTS

| | | | |
|---|---|---|---|
| 3,638,640 A | 2/1972 | Shaw | |
| 3,895,523 A * | 7/1975 | Nollen | G01K 5/00 374/E5.001 |

(Continued)

FOREIGN PATENT DOCUMENTS

| | | |
|---|---|---|
| EP | 0 505 491 | 9/1992 |
| EP | 0 541 393 | 11/1992 |

(Continued)

OTHER PUBLICATIONS

US 8,845,543 B2, 09/2014, Diab et al. (withdrawn)
(Continued)

*Primary Examiner* — Shirley X Jian
(74) *Attorney, Agent, or Firm* — Knobbe Martens Olson & Bear LLP

(57) ABSTRACT

The present disclosure relates to a sensor for monitoring the depth of consciousness of a patient. The sensor includes a plurality of light sources, light detectors, and in some embodiments, electrodes. In an embodiment, the sensor includes reusable and disposable portions.

8 Claims, 41 Drawing Sheets

Related U.S. Application Data continuation of application No. 14/470,819, filed on Aug. 27, 2014, now Pat. No. 9,538,949, which is a continuation of application No. 13/246,725, filed on Sep. 27, 2011, now Pat. No. 8,821,397.

(60) Provisional application No. 61/387,457, filed on Sep. 28, 2010.

(56) References Cited

U.S. PATENT DOCUMENTS

| | | |
|---|---|---|
| 4,223,680 A | 9/1980 | Jobsis |
| 4,281,645 A | 8/1981 | Jobsis |
| 4,321,930 A | 3/1982 | Jobsis et al. |
| 4,380,240 A | 4/1983 | Jobsis et al. |
| 4,510,938 A | 4/1985 | Jobsis et al. |
| 4,796,184 A | 1/1989 | Bahr et al. |
| 4,803,997 A | 2/1989 | Bowman |
| 4,805,623 A | 2/1989 | Jobsis |
| 4,901,238 A | 2/1990 | Suzuki et al. |
| 4,907,876 A | 3/1990 | Suzuki et al. |
| 4,908,762 A | 3/1990 | Suzuki et al. |
| 4,917,116 A | 4/1990 | LaViola et al. |
| 4,928,696 A | 5/1990 | Henderson et al. |
| 4,938,218 A | 7/1990 | Goodman et al. |
| 4,957,000 A | 9/1990 | Delpy et al. |
| 4,960,128 A | 10/1990 | Gordon et al. |
| 4,964,408 A | 10/1990 | Hink et al. |
| 4,967,038 A | 10/1990 | Gevins et al. |
| 4,972,331 A | 11/1990 | Chance |
| 4,996,992 A | 3/1991 | LaViola et al. |
| 5,022,403 A | 6/1991 | LaViola |
| 5,032,024 A | 7/1991 | Cope |
| 5,038,782 A | 8/1991 | Gevins et al. |
| 5,041,187 A | 8/1991 | Hink et al. |
| 5,069,213 A | 12/1991 | Hink et al. |
| 5,090,415 A | 2/1992 | Yamashita et al. |
| 5,099,842 A | 3/1992 | Mannheimer et al. |
| 5,101,830 A | 4/1992 | Duffy et al. |
| 5,103,829 A | 4/1992 | Suzuki et al. |
| 5,109,849 A | 5/1992 | Goodman et al. |
| 5,119,815 A | 6/1992 | Chance |
| 5,122,974 A | 6/1992 | Chance |
| 5,154,180 A | 10/1992 | Blanchet et al. |
| 5,163,438 A | 11/1992 | Gordon et al. |
| 5,179,570 A | 1/1993 | Imran |
| 5,179,957 A | 1/1993 | Williams |
| 5,181,520 A | 1/1993 | Wertheim et al. |
| 5,187,672 A | 2/1993 | Chance et al. |
| 5,195,531 A | 3/1993 | Bennett |
| 5,211,174 A | 5/1993 | Imran |
| 5,213,105 A | 5/1993 | Gratton et al. |
| 5,218,962 A | 6/1993 | Mannheimer et al. |
| 5,220,502 A | 6/1993 | Qian et al. |
| 5,226,417 A | 7/1993 | Swedlow et al. |
| 5,228,440 A | 7/1993 | Chung et al. |
| 5,233,983 A | 8/1993 | Markowitz |
| 5,247,932 A | 9/1993 | Chung et al. |
| 5,253,646 A | 10/1993 | Delpy et al. |
| 5,280,793 A | 1/1994 | Rosenfeld et al. |
| 5,289,822 A | 3/1994 | Highe et al. |
| 5,295,482 A | 3/1994 | Clare et al. |
| 5,299,118 A | 3/1994 | Martens et al. |
| 5,299,822 A | 4/1994 | Mayr et al. |
| 5,319,355 A | 6/1994 | Russek |
| 5,320,109 A | 6/1994 | Chamoun et al. |
| 5,327,888 A | 7/1994 | Imran |
| 5,331,959 A | 7/1994 | Imran |
| 5,337,744 A | 8/1994 | Branigan |
| 5,337,745 A | 8/1994 | Benaron |
| 5,341,805 A | 8/1994 | Stavridi et al. |
| 5,345,934 A | 9/1994 | Highe et al. |
| 5,353,799 A | 10/1994 | Chance |
| 5,361,773 A | 11/1994 | Ives |
| D353,195 S | 12/1994 | Savage et al. |
| D353,196 S | 12/1994 | Savage et al. |
| 5,377,674 A | 1/1995 | Kuestner |
| 5,377,675 A | 1/1995 | Ruskewicz et al. |
| 5,377,676 A | 1/1995 | Vari et al. |
| 5,381,804 A | 1/1995 | Shambroom |
| 5,386,827 A | 2/1995 | Chance et al. |
| 5,402,778 A | 4/1995 | Chance |
| 5,406,957 A | 4/1995 | Tansey |
| 5,413,098 A | 5/1995 | Benaron |
| D359,546 S | 6/1995 | Savage et al. |
| 5,421,329 A | 6/1995 | Casciani et al. |
| 5,424,843 A | 6/1995 | Tromberg et al. |
| 5,431,170 A | 7/1995 | Mathews |
| 5,435,316 A | 7/1995 | Kruse |
| 5,436,499 A | 7/1995 | Namavar et al. |
| D361,840 S | 8/1995 | Savage et al. |
| 5,441,054 A | 8/1995 | Tsuchiya |
| D362,063 S | 9/1995 | Savage et al. |
| 5,448,997 A | 9/1995 | Kruse et al. |
| 5,450,855 A | 9/1995 | Rosenfeld et al. |
| 5,452,717 A | 9/1995 | Branigan et al. |
| 5,452,718 A | 9/1995 | Clare et al. |
| D363,120 S | 10/1995 | Savage et al. |
| 5,456,252 A | 10/1995 | Vari et al. |
| 5,458,117 A | 10/1995 | Chamoun et al. |
| 5,477,051 A | 12/1995 | Tsuchiya |
| 5,479,934 A | 1/1996 | Imran |
| 5,482,034 A | 1/1996 | Lewis et al. |
| 5,482,036 A | 1/1996 | Diab et al. |
| 5,483,969 A | 1/1996 | Testerman et al. |
| 5,485,851 A | 1/1996 | Erickson |
| 5,490,505 A | 2/1996 | Diab et al. |
| 5,492,118 A | 2/1996 | Gratton et al. |
| 5,494,043 A | 2/1996 | O'Sullivan et al. |
| 5,497,769 A | 3/1996 | Gratton et al. |
| 5,511,552 A | 4/1996 | Johnson |
| 5,517,987 A | 5/1996 | Tsuchiya |
| 5,520,176 A | 5/1996 | Cohen |
| 5,520,683 A | 5/1996 | Subramaniam et al. |
| 5,522,862 A | 6/1996 | Testerman et al. |
| 5,529,065 A | 6/1996 | Tsuchiya |
| 5,533,511 A | 7/1996 | Kaspari et al. |
| 5,534,851 A | 7/1996 | Russek |
| 5,540,722 A | 7/1996 | Clare et al. |
| 5,540,733 A | 7/1996 | Testerman et al. |
| 5,546,952 A | 8/1996 | Erikson |
| 5,549,655 A | 8/1996 | Erikson |
| 5,553,614 A | 9/1996 | Chance |
| 5,561,275 A | 10/1996 | Savage et al. |
| 5,562,002 A | 10/1996 | Lalin |
| 5,564,417 A | 10/1996 | Chance |
| 5,564,418 A | 10/1996 | Ozaki et al. |
| 5,582,169 A | 12/1996 | Oda et al. |
| 5,590,649 A | 1/1997 | Caro et al. |
| 5,596,038 A | 1/1997 | Subramaniam |
| 5,596,987 A | 1/1997 | Chance |
| 5,602,924 A | 2/1997 | Durand et al. |
| 5,605,157 A | 2/1997 | Panescu et al. |
| 5,626,145 A | 5/1997 | Clapp et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,640,247 A | 6/1997 | Tsuchiya et al. |
| 5,645,440 A | 7/1997 | Tobler et al. |
| 5,664,574 A | 9/1997 | Chance |
| 5,671,914 A | 9/1997 | Kalkhoran et al. |
| 5,673,701 A | 10/1997 | Chance |
| 5,676,142 A | 10/1997 | Miwa et al. |
| 5,678,558 A | 10/1997 | Johnson |
| 5,678,560 A | 10/1997 | Sakamoto et al. |
| 5,685,299 A | 11/1997 | Diab et al. |
| 5,686,516 A | 11/1997 | Tzur |
| 5,694,931 A | 12/1997 | Tsuchiya |
| 5,697,367 A | 12/1997 | Lewis et al. |
| 5,706,821 A | 1/1998 | Matcher et al. |
| 5,711,316 A | 1/1998 | Elsberry et al. |
| 5,713,923 A | 2/1998 | Ward et al. |
| 5,726,440 A | 3/1998 | Kalkhoran et al. |
| 5,727,547 A | 3/1998 | Levinson et al. |

(56) References Cited

U.S. PATENT DOCUMENTS

| | | |
|---|---|---|
| D393,830 S | 4/1998 | Tobler et al. |
| 5,743,260 A | 4/1998 | Chung et al. |
| 5,743,262 A | 4/1998 | Lepper, Jr. et al. |
| 5,746,210 A | 5/1998 | Benaron et al. |
| 5,747,806 A | 5/1998 | Khalil et al. |
| 5,750,994 A | 5/1998 | Schlager |
| 5,752,519 A | 5/1998 | Benaron et al. |
| 5,752,914 A | 5/1998 | Delonzor et al. |
| 5,755,739 A | 5/1998 | Sun et al. |
| 5,758,644 A | 6/1998 | Diab et al. |
| 5,760,910 A | 6/1998 | Lepper, Jr. et al. |
| 5,765,563 A | 6/1998 | Schaaf et al. |
| 5,769,785 A | 6/1998 | Diab et al. |
| 5,772,587 A | 6/1998 | Gratton et al. |
| 5,772,588 A | 6/1998 | Miwa et al. |
| 5,772,605 A | 6/1998 | Weijand |
| 5,775,330 A | 7/1998 | Kangas et al. |
| 5,776,058 A | 7/1998 | Levinson et al. |
| 5,779,631 A | 7/1998 | Chance |
| 5,782,237 A | 7/1998 | Casciani et al. |
| 5,782,756 A | 7/1998 | Mannheimer |
| 5,782,757 A | 7/1998 | Diab et al. |
| 5,785,658 A | 7/1998 | Benaron et al. |
| 5,785,659 A | 7/1998 | Caro et al. |
| 5,791,347 A | 8/1998 | Flaherty et al. |
| 5,792,069 A | 8/1998 | Greenwald et al. |
| 5,807,261 A | 9/1998 | Benaron et al. |
| 5,807,263 A | 9/1998 | Chance |
| 5,810,734 A | 9/1998 | Caro et al. |
| 5,813,404 A | 9/1998 | Devlin et al. |
| 5,813,980 A | 9/1998 | Levinson et al. |
| 5,813,993 A | 9/1998 | Kaplan et al. |
| 5,816,247 A | 10/1998 | Maynard |
| 5,820,558 A | 10/1998 | Chance |
| 5,823,950 A | 10/1998 | Diab et al. |
| 5,823,952 A | 10/1998 | Levinson et al. |
| 5,830,131 A | 11/1998 | Caro et al. |
| 5,833,618 A | 11/1998 | Caro et al. |
| 5,833,709 A | 11/1998 | Rise et al. |
| 5,846,208 A | 12/1998 | Pichlmayr et al. |
| 5,851,179 A | 12/1998 | Ritson et al. |
| 5,853,370 A | 12/1998 | Chance et al. |
| RE36,044 E | 1/1999 | Benaron |
| 5,857,979 A | 1/1999 | Ryu et al. |
| 5,860,919 A | 1/1999 | Kiani-Azarbayjany et al. |
| 5,865,736 A | 2/1999 | Baker, Jr. et al. |
| 5,873,821 A | 2/1999 | Chance et al. |
| 5,879,294 A | 3/1999 | Anderson et al. |
| 5,890,929 A | 4/1999 | Mills et al. |
| 5,902,235 A | 5/1999 | Lewis et al. |
| 5,904,654 A | 5/1999 | Wohltmann et al. |
| 5,917,190 A | 6/1999 | Yodh et al. |
| 5,919,134 A | 7/1999 | Diab |
| 5,934,925 A | 8/1999 | Tobler et al. |
| 5,940,182 A | 8/1999 | Lepper, Jr. et al. |
| 5,954,053 A | 9/1999 | Chance et al. |
| 5,975,085 A | 11/1999 | Rise |
| 5,983,121 A | 11/1999 | Tsuchiya |
| 5,987,343 A | 11/1999 | Kinast |
| 5,987,346 A | 11/1999 | Benaron et al. |
| 5,987,351 A | 11/1999 | Chance |
| 5,995,855 A | 11/1999 | Kiani et al. |
| 5,997,343 A | 12/1999 | Mills et al. |
| 5,999,846 A | 12/1999 | Pardey et al. |
| 6,002,952 A | 12/1999 | Diab et al. |
| 6,010,937 A | 1/2000 | Karam et al. |
| 6,011,986 A | 1/2000 | Diab et al. |
| 6,011,990 A | 1/2000 | Schultz et al. |
| 6,077,223 A | 1/2000 | Satherley |
| 6,027,452 A | 2/2000 | Flaherty et al. |
| 6,032,064 A | 2/2000 | Devlin et al. |
| 6,032,065 A | 2/2000 | Brown et al. |
| 6,032,072 A | 2/2000 | Greenwald et al. |
| 6,035,223 A | 3/2000 | Baker, Jr. |
| 6,036,642 A | 3/2000 | Diab et al. |
| 6,040,578 A | 3/2000 | Malin et al. |
| 6,041,783 A | 3/2000 | Gruenke |
| 6,045,509 A | 4/2000 | Caro et al. |
| 6,052,619 A | 4/2000 | John |
| 6,058,324 A | 5/2000 | Chance |
| 6,058,331 A | 5/2000 | King |
| 6,066,204 A | 5/2000 | Haven |
| 6,067,462 A | 5/2000 | Diab et al. |
| 6,067,467 A | 5/2000 | John |
| 6,069,975 A | 5/2000 | Lehmann et al. |
| 6,070,098 A | 5/2000 | Moore-Ede et al. |
| 6,075,610 A | 6/2000 | Ueda et al. |
| 6,076,010 A | 6/2000 | Boas et al. |
| 6,078,833 A | 6/2000 | Hueber |
| 6,081,735 A | 6/2000 | Diab et al. |
| 6,088,607 A | 7/2000 | Diab et al. |
| 6,108,571 A | 8/2000 | Minoz et al. |
| 6,109,269 A | 8/2000 | Rise et al. |
| 6,110,522 A | 8/2000 | Lepper, Jr. et al. |
| 6,115,622 A | 9/2000 | Minoz |
| 6,115,673 A | 9/2000 | Malin et al. |
| 6,119,029 A | 9/2000 | Williams |
| 6,124,597 A | 9/2000 | Shehada et al. |
| 6,128,520 A | 10/2000 | Minoz |
| 6,128,521 A | 10/2000 | Marro et al. |
| 6,129,675 A | 10/2000 | Jay |
| 6,141,574 A | 10/2000 | Satherley et al. |
| 6,142,938 A | 11/2000 | Satherley |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,154,669 A | 11/2000 | Hunter et al. |
| 6,157,850 A | 12/2000 | Diab et al. |
| 6,157,857 A | 12/2000 | Dimpfel |
| 6,165,005 A | 12/2000 | Mills et al. |
| 6,176,242 B1 | 1/2001 | Rise |
| 6,184,521 B1 | 2/2001 | Coffin, IV et al. |
| 6,192,260 B1 | 2/2001 | Chance |
| 6,192,261 B1 | 2/2001 | Gratton et al. |
| 6,200,264 B1 | 3/2001 | Satherley et al. |
| 6,206,830 B1 | 3/2001 | Diab et al. |
| 6,216,021 B1 | 4/2001 | Franceschini et al. |
| 6,227,203 B1 | 5/2001 | Rise et al. |
| 6,229,856 B1 | 5/2001 | Diab et al. |
| 6,232,609 B1 | 5/2001 | Snyder et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,236,874 B1 | 5/2001 | Devlin et al. |
| 6,236,885 B1 | 5/2001 | Hunter et al. |
| 6,240,305 B1 | 5/2001 | Tsuchiya |
| 6,241,683 B1 | 6/2001 | Macklem et al. |
| 6,245,013 B1 | 6/2001 | Minoz et al. |
| 6,246,892 B1 | 6/2001 | Chance |
| 6,251,126 B1 | 6/2001 | Ottenhoff et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,221 B1 | 7/2001 | Chance et al. |
| 6,263,222 B1 | 7/2001 | Diab et al. |
| 6,263,237 B1 | 7/2001 | Rise |
| 6,269,269 B1 | 7/2001 | Ottenhoff et al. |
| 6,272,363 B1 | 8/2001 | Casciani et al. |
| 6,272,367 B1 | 8/2001 | Chance |
| 6,272,378 B1 | 8/2001 | Baumgart-Schmitt |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,298,252 B1 | 10/2001 | Kovach et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,335,792 B1 | 1/2002 | Tsuchiya |
| 6,337,997 B1 | 1/2002 | Rise |
| 6,338,713 B1 | 1/2002 | Chamoun et al. |

(56) References Cited

U.S. PATENT DOCUMENTS

| | | |
|---|---|---|
| 6,343,224 B1 | 1/2002 | Parker |
| 6,343,229 B1 | 1/2002 | Siebler et al. |
| 6,349,228 B1 | 2/2002 | Kiani et al. |
| 6,356,784 B1 | 3/2002 | Lozano et al. |
| 6,360,114 B1 | 3/2002 | Diab et al. |
| 6,368,283 B1 | 4/2002 | Xu et al. |
| 6,368,287 B1 | 4/2002 | Hadas |
| 6,371,921 B1 | 4/2002 | Caro et al. |
| 6,374,140 B1 | 4/2002 | Rise |
| 6,377,829 B1 | 4/2002 | Al-Ali |
| 6,377,840 B1 | 4/2002 | Gritsenko et al. |
| 6,385,486 B1 | 5/2002 | John et al. |
| 6,388,240 B2 | 5/2002 | Schulz et al. |
| 6,397,091 B2 | 5/2002 | Diab et al. |
| 6,397,099 B1 | 5/2002 | Chance |
| 6,397,845 B1 | 6/2002 | Burton |
| 6,411,373 B1 | 6/2002 | Garside et al. |
| 6,415,167 B1 | 7/2002 | Blank et al. |
| 6,416,480 B1 | 7/2002 | Nenov |
| 6,430,437 B1 | 8/2002 | Marro |
| 6,430,525 B1 | 8/2002 | Weber et al. |
| 6,456,862 B2 | 9/2002 | Benni |
| 6,463,310 B1 | 10/2002 | Swedlow et al. |
| 6,463,311 B1 | 10/2002 | Diab |
| 6,470,199 B1 | 10/2002 | Kopotic et al. |
| 6,473,632 B1 | 10/2002 | Myers |
| 6,481,899 B1 | 11/2002 | Quast et al. |
| 6,487,343 B1 | 11/2002 | Lewandowski et al. |
| 6,487,429 B2 | 11/2002 | Hockersmith et al. |
| 6,496,724 B1 | 12/2002 | Levendowski et al. |
| 6,497,658 B2 | 12/2002 | Roizen et al. |
| 6,501,975 B2 | 12/2002 | Diab et al. |
| 6,505,059 B1 | 1/2003 | Kollias et al. |
| 6,511,424 B1 | 1/2003 | Moore-Ede et al. |
| 6,515,273 B2 | 2/2003 | Al-Ali |
| 6,516,209 B2 | 2/2003 | Cheng et al. |
| 6,516,214 B1 | 2/2003 | Boas |
| 6,519,487 B1 | 2/2003 | Parker |
| 6,525,386 B1 | 2/2003 | Mills et al. |
| 6,526,300 B1 | 2/2003 | Kiani et al. |
| 6,526,309 B1 | 2/2003 | Chance |
| 6,534,012 B1 | 3/2003 | Hazen et al. |
| 6,537,228 B1 | 3/2003 | Lambert |
| 6,541,756 B2 | 4/2003 | Schulz et al. |
| 6,542,764 B1 | 4/2003 | Al-Ali et al. |
| 6,542,772 B1 | 4/2003 | Chance |
| 6,549,284 B1 | 4/2003 | Boas et al. |
| 6,564,076 B1 | 5/2003 | Chance |
| 6,567,165 B1 | 5/2003 | Tsuchiya et al. |
| 6,572,542 B1 | 6/2003 | Houben et al. |
| 6,575,902 B1 | 6/2003 | Burton |
| 6,577,884 B1 | 6/2003 | Boas |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,587,703 B2 | 7/2003 | Cheng et al. |
| 6,591,123 B2 | 7/2003 | Fein et al. |
| 6,594,513 B1 | 7/2003 | Jobsis et al. |
| 6,594,518 B1 | 7/2003 | Benaron et al. |
| 6,595,316 B2 | 7/2003 | Cybulski et al. |
| 6,597,931 B1 | 7/2003 | Cheng et al. |
| 6,597,932 B2 | 7/2003 | Tian et al. |
| 6,597,933 B2 | 7/2003 | Kiani et al. |
| 6,597,944 B1 | 7/2003 | Hadas |
| 6,599,281 B1 | 7/2003 | Struys et al. |
| 6,605,072 B2 | 8/2003 | Struys et al. |
| 6,606,511 B1 | 8/2003 | Ali et al. |
| 6,609,024 B1 | 8/2003 | Ryu et al. |
| 6,615,065 B1 | 9/2003 | Barrett et al. |
| 6,618,614 B1 | 9/2003 | Chance |
| 6,631,291 B2 | 10/2003 | Viertio-Oja et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,654,626 B2 | 11/2003 | Devlin et al. |
| 6,654,632 B2 | 11/2003 | Lange et al. |
| 6,658,276 B2 | 12/2003 | Kiani et al. |
| 6,661,161 B1 | 12/2003 | Lanzo et al. |
| 6,662,033 B2 | 12/2003 | Casciani et al. |
| 6,665,560 B2 | 12/2003 | Becker et al. |
| 6,667,803 B1 | 12/2003 | Flessland et al. |
| 6,671,530 B2 | 12/2003 | Chung et al. |
| 6,671,531 B2 | 12/2003 | Al-Ali |
| 6,671,555 B2 | 12/2003 | Gielen et al. |
| 6,675,031 B1 | 1/2004 | Porges et al. |
| 6,678,543 B2 | 1/2004 | Diab et al. |
| 6,684,090 B2 | 1/2004 | Ali et al. |
| 6,684,091 B2 | 1/2004 | Parker |
| 6,687,524 B1 | 2/2004 | Svejk |
| 6,690,959 B2 | 2/2004 | Thompson |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,701,170 B2 | 3/2004 | Stetson |
| 6,708,048 B1 | 3/2004 | Chance |
| 6,708,049 B1 | 3/2004 | Berson et al. |
| 6,711,426 B2 | 3/2004 | Benaron et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,728,564 B2 | 4/2004 | Lahteenmaki |
| 6,731,975 B1 | 5/2004 | Viertio-Oja |
| 6,735,458 B2 | 5/2004 | Cheng et al. |
| 6,735,459 B2 | 5/2004 | Parker |
| 6,738,652 B2 | 5/2004 | Mattu et al. |
| 6,745,060 B2 | 6/2004 | Diab et al. |
| 6,748,259 B1 | 6/2004 | Benaron et al. |
| 6,748,263 B2 | 6/2004 | Griffiths et al. |
| 6,751,499 B2 | 6/2004 | Lange et al. |
| 6,757,558 B2 | 6/2004 | Lange et al. |
| 6,760,607 B2 | 7/2004 | Al-Ali |
| 6,768,920 B2 | 7/2004 | Lange et al. |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,795,724 B2 | 9/2004 | Hogan |
| 6,801,648 B2 | 10/2004 | Cheng |
| 6,801,797 B2 | 10/2004 | Mannheimer et al. |
| 6,801,803 B2 | 10/2004 | Viertio-Oja |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,047 B2 | 12/2004 | Heitmeier et al. |
| 6,830,711 B2 | 12/2004 | Mills et al. |
| 6,836,502 B2 | 12/2004 | Canady et al. |
| 6,839,583 B1 | 1/2005 | Lewandowski et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,871,098 B2 | 5/2005 | Nuttin et al. |
| 6,892,006 B2 | 5/2005 | Lewandowski et al. |
| 6,898,452 B2 | 5/2005 | Al-Ali et al. |
| 6,907,280 B2 | 6/2005 | Becerra et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,934,579 B2 | 8/2005 | Mantzxaridis et al. |
| 6,939,305 B2 | 9/2005 | Flaherty et al. |

(56) References Cited

U.S. PATENT DOCUMENTS

| | | |
|---|---|---|
| 6,943,348 B1 | 9/2005 | Coffin, IV |
| 6,944,497 B2 | 9/2005 | Stypulkowski |
| 6,950,687 B2 | 9/2005 | Al-Ali |
| 6,950,698 B2 | 9/2005 | Sarkela et al. |
| 6,956,649 B2 | 10/2005 | Acosta et al. |
| 6,956,650 B2 | 10/2005 | Boas et al. |
| 6,957,368 B2 | 10/2005 | Neumiller et al. |
| 6,958,815 B2 | 10/2005 | Bevilacqua et al. |
| 6,961,598 B2 | 11/2005 | Diab |
| 6,970,792 B1 | 11/2005 | Diab |
| 6,975,901 B2 | 12/2005 | Philip |
| 6,979,812 B2 | 12/2005 | Al-Ali |
| 6,985,763 B2 | 1/2006 | Boas et al. |
| 6,985,764 B2 | 1/2006 | Mason et al. |
| 6,985,833 B2 | 1/2006 | Shambroom et al. |
| 6,990,364 B2 | 1/2006 | Ruchti et al. |
| 6,993,371 B2 | 1/2006 | Kiani et al. |
| 6,993,380 B1 | 1/2006 | Modarres |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,010,341 B2 | 3/2006 | Chance |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,035,744 B2 | 4/2006 | Cheriet et al. |
| 7,039,449 B2 | 5/2006 | Al-Ali |
| 7,041,060 B2 | 5/2006 | Flaherty et al. |
| 7,044,918 B2 | 5/2006 | Diab |
| 7,047,054 B2 | 5/2006 | Benni |
| 7,047,055 B2 | 5/2006 | Boas et al. |
| 7,047,056 B2 | 5/2006 | Hannula et al. |
| 7,048,687 B1 | 5/2006 | Reuss et al. |
| 7,054,680 B1 | 5/2006 | Genger et al. |
| 7,067,893 B2 | 6/2006 | Mills et al. |
| 7,072,701 B2 | 7/2006 | Chen et al. |
| 7,079,977 B2 | 7/2006 | Osorio et al. |
| D526,719 S | 8/2006 | Richie, Jr. et al. |
| 7,085,597 B2 | 8/2006 | Fein et al. |
| 7,087,075 B2 | 8/2006 | Briscoe et al. |
| 7,092,748 B2 | 8/2006 | Valdes et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,134,438 B2 | 11/2006 | Makower et al. |
| 7,139,603 B2 | 11/2006 | Chance |
| 7,142,901 B2 | 11/2006 | Kiani et al. |
| 7,146,211 B2 | 12/2006 | Frei et al. |
| 7,149,561 B2 | 12/2006 | Diab |
| 7,149,572 B2 | 12/2006 | Frei et al. |
| 7,162,306 B2 | 1/2007 | Caby et al. |
| 7,167,743 B2 | 1/2007 | Heruth et al. |
| 7,174,206 B2 | 2/2007 | Frei et al. |
| 7,179,279 B2 | 2/2007 | Radons et al. |
| 7,186,966 B2 | 3/2007 | Al-Ali |
| 7,190,261 B2 | 3/2007 | Al-Ali |
| 7,209,861 B2 | 4/2007 | Hively |
| 7,215,984 B2 | 5/2007 | Diab et al. |
| 7,215,986 B2 | 5/2007 | Diab et al. |
| 7,218,964 B2 | 5/2007 | Hill et al. |
| 7,220,240 B2 | 5/2007 | Struys et al. |
| 7,221,971 B2 | 5/2007 | Diab et al. |
| 7,221,975 B2 | 5/2007 | Lindstrom |
| 7,221,979 B2 | 5/2007 | Zhou et al. |
| 7,225,006 B2 | 5/2007 | Al-Ali et al. |
| 7,225,007 B2 | 5/2007 | Al-Ali et al. |
| 7,225,013 B2 | 5/2007 | Geva et al. |
| RE39,672 E | 6/2007 | Shehada et al. |
| 7,228,169 B2 | 6/2007 | Viertio-Oja |
| 7,229,430 B2 | 6/2007 | Hickle et al. |
| 7,231,245 B2 | 6/2007 | Greenwald et al. |
| 7,231,246 B2 | 6/2007 | Rautee et al. |
| 7,232,435 B2 | 6/2007 | Hildebrand et al. |
| 7,239,385 B2 | 7/2007 | Schmitz et al. |
| 7,239,901 B2 | 7/2007 | Gritsenko |
| 7,239,905 B2 | 7/2007 | Kiani-Azarbayjany et al. |
| 7,239,988 B2 | 7/2007 | Hasson et al. |
| 7,242,983 B2 | 7/2007 | Frei et al. |
| 7,245,953 B1 | 7/2007 | Parker |
| 7,248,909 B2 | 7/2007 | Lee et al. |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,254,500 B2 | 8/2007 | Makeig et al. |
| 7,266,412 B2 | 9/2007 | Stypulkowski |
| 7,272,425 B2 | 9/2007 | Al-Ali |
| 7,274,955 B2 | 9/2007 | Kiani et al. |
| D554,263 S | 10/2007 | Al-Ali et al. |
| 7,277,741 B2 | 10/2007 | Debreczeny et al. |
| 7,277,831 B1 | 10/2007 | Pawelzik et al. |
| 7,280,858 B2 | 10/2007 | Al-Ali et al. |
| 7,280,867 B2 | 10/2007 | Frei et al. |
| 7,288,066 B2 | 10/2007 | Drew |
| 7,289,835 B2 | 10/2007 | Mansfield et al. |
| 7,289,837 B2 | 10/2007 | Mannheimer et al. |
| 7,292,883 B2 | 11/2007 | De Felice et al. |
| 7,295,866 B2 | 11/2007 | Al-Ali |
| 7,308,304 B2 | 12/2007 | Hampton et al. |
| 7,313,427 B2 | 12/2007 | Benni |
| 7,328,053 B1 | 2/2008 | Diab et al. |
| 7,332,784 B2 | 2/2008 | Mills et al. |
| 7,333,647 B2 | 2/2008 | Boas et al. |
| 7,340,287 B2 | 3/2008 | Mason et al. |
| 7,341,559 B2 | 3/2008 | Schulz et al. |
| 7,343,186 B2 | 3/2008 | Lamego et al. |
| 7,343,187 B2 | 3/2008 | Stetson |
| 7,349,726 B2 | 3/2008 | Casciani et al. |
| D566,282 S | 4/2008 | Al-Ali et al. |
| 7,355,512 B1 | 4/2008 | Al-Ali |
| 7,355,688 B2 | 4/2008 | Lash et al. |
| 7,356,365 B2 | 4/2008 | Schurman et al. |
| 7,359,837 B2 | 4/2008 | Drew et al. |
| D568,479 S | 5/2008 | Mao et al. |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,373,198 B2 | 5/2008 | Bibian et al. |
| 7,376,453 B1 | 5/2008 | Diab et al. |
| 7,376,454 B2 | 5/2008 | Casciani et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,385,443 B1 | 6/2008 | Denison |
| 7,391,257 B1 | 6/2008 | Denison et al. |
| 7,392,074 B2 | 6/2008 | Isaacson et al. |
| 7,395,158 B2 | 7/2008 | Monfre et al. |
| 7,415,297 B2 | 8/2008 | Al-Ali et al. |
| 7,415,298 B2 | 8/2008 | Casciani et al. |
| 7,418,290 B2 | 8/2008 | Devlin et al. |
| 7,421,297 B2 | 9/2008 | Giftakis et al. |
| 7,427,165 B2 | 9/2008 | Benaron et al. |
| 7,428,432 B2 | 9/2008 | Ali et al. |
| 7,428,434 B2 | 9/2008 | Tromberg et al. |
| 7,429,938 B1 | 9/2008 | Corndorf |
| 7,438,683 B2 | 10/2008 | Al-Ali et al. |
| 7,440,787 B2 | 10/2008 | Diab |
| 7,454,240 B2 | 11/2008 | Diab et al. |
| 7,457,652 B2 | 11/2008 | Porges et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,474,245 B1 | 1/2009 | Wang et al. |
| 7,474,247 B1 | 1/2009 | Heinks et al. |
| 7,478,108 B2 | 1/2009 | Townsend et al. |
| 7,479,910 B1 | 1/2009 | Heinks et al. |
| 7,483,729 B2 | 1/2009 | Al-Ali et al. |
| 7,483,730 B2 | 1/2009 | Diab et al. |

(56) References Cited

U.S. PATENT DOCUMENTS

| | | |
|---|---|---|
| 7,483,731 B2 | 1/2009 | Hoarau et al. |
| 7,486,977 B2 | 2/2009 | Sweitzer et al. |
| 7,489,958 B2 | 2/2009 | Diab et al. |
| 7,496,391 B2 | 2/2009 | Diab et al. |
| 7,496,393 B2 | 2/2009 | Diab et al. |
| 7,496,400 B2 | 2/2009 | Hoskonen et al. |
| D587,657 S | 3/2009 | Al-Ali et al. |
| 7,499,740 B2 | 3/2009 | Nordstrom et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,153 B2 | 3/2009 | Blank et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,515,948 B1 | 4/2009 | Balberg et al. |
| 7,519,406 B2 | 4/2009 | Blank et al. |
| 7,522,949 B2 | 4/2009 | Berson et al. |
| 7,526,328 B2 | 4/2009 | Diab et al. |
| 7,526,335 B2 | 4/2009 | Ferek-Petric |
| 7,526,340 B2 | 4/2009 | Drew |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,542,803 B2 | 6/2009 | Heruth et al. |
| 7,563,110 B2 | 7/2009 | Al-Ali et al. |
| 7,590,455 B2 | 9/2009 | Heruth et al. |
| 7,593,230 B2 | 9/2009 | Abul-Haj et al. |
| 7,594,889 B2 | 9/2009 | Ores et al. |
| 7,596,398 B2 | 9/2009 | Al-Ali et al. |
| 7,606,608 B2 | 10/2009 | Blank et al. |
| 7,610,082 B2 | 10/2009 | Chance |
| 7,610,083 B2 | 10/2009 | Drew et al. |
| 7,618,375 B2 | 11/2009 | Flaherty et al. |
| 7,620,674 B2 | 11/2009 | Ruchti et al. |
| 7,623,053 B2 | 11/2009 | Terry et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| 7,684,872 B2 | 3/2010 | Carney et al. |
| D614,305 S | 4/2010 | Al-Ali et al. |
| 7,697,966 B2 | 4/2010 | Monfre et al. |
| 7,698,002 B2 | 4/2010 | Music et al. |
| 7,698,105 B2 | 4/2010 | Ruchti et al. |
| 7,706,871 B2 | 4/2010 | Devlin et al. |
| 7,706,889 B2 | 4/2010 | Gerber et al. |
| 7,706,896 B2 | 4/2010 | Music et al. |
| RE41,317 E | 5/2010 | Parker |
| RE41,333 E | 5/2010 | Blank et al. |
| 7,714,757 B2 | 5/2010 | Denison et al. |
| 7,715,919 B2 | 5/2010 | Osorio et al. |
| 7,717,932 B2 | 5/2010 | McFarlin et al. |
| 7,729,733 B2 | 6/2010 | Al-Ali et al. |
| 7,729,773 B2 | 6/2010 | Sloan |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,761,145 B2 | 7/2010 | Virag et al. |
| 7,761,146 B2 | 7/2010 | Carlson et al. |
| 7,764,982 B2 | 7/2010 | Dalke et al. |
| 7,764,988 B2 | 7/2010 | Drew et al. |
| 7,764,989 B2 | 7/2010 | Carlson et al. |
| D621,516 S | 8/2010 | Kiani et al. |
| 7,769,464 B2 | 8/2010 | Gerber et al. |
| 7,775,993 B2 | 8/2010 | Heruth et al. |
| 7,791,155 B2 | 9/2010 | Diab |
| 7,792,583 B2 | 9/2010 | Miesel et al. |
| 7,801,581 B2 | 9/2010 | Diab |
| 7,805,196 B2 | 9/2010 | Miesel et al. |
| 7,809,434 B2 | 10/2010 | Kofol et al. |
| 7,819,909 B2 | 10/2010 | Goetz et al. |
| 7,822,452 B2 | 10/2010 | Schurman et al. |
| 7,822,481 B2 | 10/2010 | Gerber et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,853,322 B2 | 12/2010 | Bourget et al. |
| 7,865,222 B2 | 1/2011 | Weber et al. |
| 7,865,244 B2 | 1/2011 | Giftakis et al. |
| 7,873,497 B2 | 1/2011 | Weber et al. |
| 7,957,797 B2 | 1/2011 | Bourget et al. |
| 7,880,606 B2 | 2/2011 | Al-Ali |
| 7,880,626 B2 | 2/2011 | Al-Ali et al. |
| 7,881,798 B2 | 2/2011 | Miesel et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,904,168 B2 | 3/2011 | Corndorf |
| 7,909,772 B2 | 3/2011 | Popov et al. |
| 7,910,875 B2 | 3/2011 | Al-Ali |
| 7,912,537 B2 | 3/2011 | Lee et al. |
| 7,917,199 B2 | 3/2011 | Drew et al. |
| 7,935,935 B2 | 3/2011 | Roberts et al. |
| 7,953,492 B2 | 3/2011 | Corndorf |
| 7,919,713 B2 | 4/2011 | Al-Ali et al. |
| 7,925,511 B2 | 4/2011 | Li et al. |
| 7,933,646 B2 | 4/2011 | Frei et al. |
| 7,933,658 B2 | 4/2011 | Corndorf |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,944,551 B2 | 5/2011 | Addison et al. |
| 7,951,086 B2 | 5/2011 | Flaherty et al. |
| 7,957,780 B2 | 6/2011 | Lamego et al. |
| 7,957,799 B2 | 6/2011 | Sullivan et al. |
| 7,957,809 B2 | 6/2011 | Bourget et al. |
| 7,957,812 B2 | 6/2011 | Corndorf |
| 7,962,188 B2 | 6/2011 | Kiani et al. |
| 7,962,190 B1 | 6/2011 | Diab et al. |
| 7,976,472 B2 | 7/2011 | Kiani |
| 7,979,130 B2 | 7/2011 | Carlson et al. |
| 7,983,757 B2 | 7/2011 | Miyazawa et al. |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,000,788 B2 | 8/2011 | Giftakis et al. |
| 8,005,534 B2 | 8/2011 | Greenwald et al. |
| 8,008,088 B2 | 8/2011 | Bellott et al. |
| RE42,753 E | 9/2011 | Kiani-Azarbayjany et al. |
| 8,016,776 B2 | 9/2011 | Bourget et al. |
| 8,016,846 B2 | 9/2011 | McFarlin et al. |
| 8,019,400 B2 | 9/2011 | Diab et al. |
| 8,021,299 B2 | 9/2011 | Miesel et al. |
| 8,024,029 B2 | 9/2011 | Drew et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,050,751 B2 | 11/2011 | Zhang et al. |
| 8,055,348 B2 | 11/2011 | Heruth et al. |
| 8,099,170 B2 | 1/2012 | Jensen et al. |
| 8,103,328 B2 | 1/2012 | Turner et al. |
| 8,108,033 B2 | 1/2012 | Drew et al. |
| 8,108,038 B2 | 1/2012 | Giftakis et al. |
| 8,209,009 B2 | 1/2012 | Giftakis et al. |
| RE43,169 E | 2/2012 | Parker |
| 8,112,148 B2 | 2/2012 | Giftakis et al. |
| 8,112,153 B2 | 2/2012 | Giftakis et al. |
| 8,118,620 B2 | 2/2012 | Al-Ali et al. |
| 8,121,694 B2 | 2/2012 | Molnar et al. |

(56) References Cited

U.S. PATENT DOCUMENTS

| | | |
|---|---|---|
| 8,126,528 B2 | 2/2012 | Diab et al. |
| 8,128,572 B2 | 3/2012 | Diab et al. |
| 8,130,105 B2 | 3/2012 | Al-Ali et al. |
| 8,135,473 B2 | 3/2012 | Miesel et al. |
| 8,145,287 B2 | 3/2012 | Diab et al. |
| 8,150,487 B2 | 4/2012 | Diab et al. |
| 8,160,683 B2 | 4/2012 | Shah et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,187,181 B2 | 5/2012 | Osorio et al. |
| 8,190,223 B2 | 5/2012 | Al-Ali et al. |
| 8,190,227 B2 | 5/2012 | Diab et al. |
| 8,190,251 B2 | 5/2012 | Molnar et al. |
| 8,200,340 B2 | 6/2012 | Skelton et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,209,018 B2 | 6/2012 | Osorio et al. |
| 8,209,019 B2 | 6/2012 | Giftakis et al. |
| 8,209,029 B2 | 6/2012 | Gray et al. |
| 8,214,035 B2 | 7/2012 | Giftakis et al. |
| 8,219,172 B2 | 7/2012 | Schurman et al. |
| 8,219,206 B2 | 7/2012 | Skelton et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,229,559 B2 | 7/2012 | Westendorp et al. |
| 8,231,556 B2 | 7/2012 | Skelton et al. |
| 8,233,955 B2 | 7/2012 | Al-Ali et al. |
| 8,244,325 B2 | 8/2012 | Al-Ali et al. |
| 8,244,339 B2 | 8/2012 | Shen et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,265,769 B2 | 9/2012 | Denison |
| 8,274,360 B2 | 9/2012 | Sampath et al. |
| 8,280,473 B2 | 10/2012 | Al-Ali |
| 8,287,451 B2 | 10/2012 | Hu et al. |
| 8,287,520 B2 | 10/2012 | Drew et al. |
| 8,290,596 B2 | 10/2012 | Wei et al. |
| 8,301,217 B2 | 10/2012 | Al-Ali et al. |
| 8,301,233 B2 | 10/2012 | Zhang et al. |
| 8,306,596 B2 | 11/2012 | Schurman et al. |
| 8,308,661 B2 | 11/2012 | Miesel et al. |
| 8,310,336 B2 | 11/2012 | Muhsin et al. |
| 8,315,683 B2 | 11/2012 | Al-Ali et al. |
| 8,315,709 B2 | 11/2012 | Corndorf |
| RE43,860 E | 12/2012 | Parker |
| 8,326,418 B2 | 12/2012 | Sommer et al. |
| 8,326,431 B2 | 12/2012 | Werder et al. |
| 8,332,041 B2 | 12/2012 | Skelton et al. |
| 8,337,403 B2 | 12/2012 | Al-Ali et al. |
| 8,340,769 B2 | 12/2012 | Receveur et al. |
| 8,346,190 B2 | 1/2013 | Corndorf |
| 8,346,330 B2 | 1/2013 | Lamego |
| 8,352,039 B2 | 1/2013 | Davis et al. |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,359,094 B2 | 1/2013 | Bonner et al. |
| 8,364,223 B2 | 1/2013 | Al-Ali et al. |
| 8,364,226 B2 | 1/2013 | Diab et al. |
| 8,364,272 B2 | 1/2013 | Goetz |
| 8,473,063 B2 | 1/2013 | Gupta et al. |
| 8,374,665 B2 | 2/2013 | Lamego |
| 8,376,943 B2 | 2/2013 | Kovach et al. |
| 8,380,314 B2 | 2/2013 | Panken et al. |
| 8,385,995 B2 | 2/2013 | Al-Ali et al. |
| 8,385,996 B2 | 2/2013 | Smith et al. |
| 8,386,053 B2 | 2/2013 | Kornet |
| 8,388,353 B2 | 3/2013 | Kiani et al. |
| 8,388,555 B2 | 3/2013 | Panken et al. |
| 8,396,526 B2 | 3/2013 | Benni |
| 8,399,822 B2 | 3/2013 | Al-Ali |
| 8,400,290 B2 | 3/2013 | Baker et al. |
| 8,401,602 B2 | 3/2013 | Kiani |
| 8,401,666 B2 | 3/2013 | Skelton et al. |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,419,982 B2 | 4/2013 | Copp-Howland et al. |
| 8,423,106 B2 | 4/2013 | Lamego et al. |
| 8,428,674 B2 | 4/2013 | Duffy et al. |
| 8,428,675 B2 | 4/2013 | McKenna |
| 8,428,733 B2 | 4/2013 | Carlson et al. |
| 8,428,744 B2 | 4/2013 | Stancer et al. |
| 8,428,967 B2 | 4/2013 | Olsen et al. |
| 8,430,817 B1 | 4/2013 | Al-Ali et al. |
| 8,406,890 B2 | 5/2013 | Goetz |
| 8,437,825 B2 | 5/2013 | Dalvi et al. |
| 8,447,406 B2 | 5/2013 | Wu et al. |
| 8,452,364 B2 | 5/2013 | Hannula et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,485,979 B2 | 7/2013 | Giftakis et al. |
| 8,489,196 B2 | 7/2013 | Miesel et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,515,510 B2 | 8/2013 | MacLaughlin |
| 8,515,550 B2 | 8/2013 | Skelton et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| 8,532,757 B2 | 9/2013 | Molnar et al. |
| 8,538,513 B2 | 9/2013 | Molnar et al. |
| 8,538,705 B2 | 9/2013 | Greenwald |
| 8,543,214 B2 | 9/2013 | Osorio et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,548,557 B2 | 10/2013 | Garstka et al. |
| 8,554,331 B2 | 10/2013 | Gerber et al. |
| 8,560,032 B2 | 10/2013 | Al-Ali et al. |
| 8,560,034 B1 | 10/2013 | Diab et al. |
| 8,560,064 B2 | 10/2013 | Bonner et al. |
| 8,565,886 B2 | 10/2013 | Nelson et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,577,440 B2 | 11/2013 | Afanasewicz et al. |
| 8,578,082 B2 | 11/2013 | Medina et al. |
| 8,579,786 B2 | 11/2013 | Osorio et al. |
| 8,579,834 B2 | 11/2013 | Davis et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,594,779 B2 | 11/2013 | Denison et al. |
| 8,594,798 B2 | 11/2013 | Osorio et al. |
| 8,600,467 B2 | 12/2013 | Al-Ali et al. |
| 8,606,342 B2 | 12/2013 | Diab |
| 8,615,299 B2 | 12/2013 | Goetz |
| 8,617,152 B2 | 12/2013 | Werneth et al. |
| 8,626,255 B2 | 1/2014 | Al-Ali et al. |
| 8,630,691 B2 | 1/2014 | Lamego et al. |

(56) References Cited

U.S. PATENT DOCUMENTS

| | | |
|---|---|---|
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,660,799 B2 | 2/2014 | Watson et al. |
| 8,663,107 B2 | 3/2014 | Kiani |
| 8,666,468 B1 | 3/2014 | Al-Ali |
| 8,666,505 B2 | 3/2014 | O'Brien et al. |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,671,237 B2 | 3/2014 | Ma et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,688,185 B2 | 4/2014 | Scholl et al. |
| 8,690,799 B2 | 4/2014 | Telfort et al. |
| 8,700,112 B2 | 4/2014 | Kiani |
| 8,700,122 B2 | 4/2014 | Cordero et al. |
| 8,702,627 B2 | 4/2014 | Telfort et al. |
| 8,706,179 B2 | 4/2014 | Parker |
| 8,706,181 B2 | 4/2014 | Stypulkowski et al. |
| 8,708,934 B2 | 4/2014 | Skelton et al. |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,725,244 B2 | 5/2014 | Miesel et al. |
| 8,728,059 B2 | 5/2014 | Karst et al. |
| 8,740,792 B1 | 6/2014 | Kiani et al. |
| 8,744,587 B2 | 6/2014 | Miesel et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,871 B2 | 6/2014 | Weng et al. |
| 8,755,872 B1 | 6/2014 | Marinow |
| 8,761,850 B2 | 6/2014 | Lamego |
| 8,761,890 B2 | 6/2014 | Gupta et al. |
| 8,764,671 B2 | 7/2014 | Kiani |
| 8,768,423 B2 | 7/2014 | Shakespeare et al. |
| 8,768,446 B2 | 7/2014 | Drew et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,792,991 B2 | 7/2014 | Gerber et al. |
| 8,798,708 B2 | 8/2014 | Tremblay |
| 8,798,764 B2 | 8/2014 | Molnar et al. |
| 8,801,613 B2 | 8/2014 | Al-Ali et al. |
| 8,805,465 B2 | 8/2014 | Hodge et al. |
| 8,805,528 B2 | 8/2014 | Corndorf |
| 8,805,537 B1 | 8/2014 | Cong et al. |
| 8,812,098 B2 | 8/2014 | Giftakis et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,838,254 B2 | 9/2014 | McClure et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,095 B2 | 10/2014 | Schlottau et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,868,173 B2 | 10/2014 | Nelson et al. |
| 8,868,212 B2 | 10/2014 | Gray |
| 8,870,792 B2 | 10/2014 | Al-Ali et al. |
| 8,880,576 B2 | 11/2014 | Ochs et al. |
| 8,886,271 B2 | 11/2014 | Kiani et al. |
| 8,886,323 B2 | 11/2014 | Wu et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,892,207 B2 | 11/2014 | Nelson et al. |
| 8,897,847 B2 | 11/2014 | Al-Ali |
| 8,898,037 B2 | 11/2014 | Watson et al. |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,914,115 B2 | 12/2014 | Giftakis et al. |
| 8,914,119 B2 | 12/2014 | Wu et al. |
| 8,918,176 B2 | 12/2014 | Nelson et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,922,788 B2 | 12/2014 | Addison et al. |
| 8,929,964 B2 | 1/2015 | Al-Ali et al. |
| 8,936,630 B2 | 1/2015 | Denison et al. |
| 8,941,523 B1 | 1/2015 | Shen et al. |
| 8,942,777 B2 | 1/2015 | Diab et al. |
| 8,948,834 B2 | 2/2015 | Diab et al. |
| 8,948,835 B2 | 2/2015 | Diab |
| 8,958,870 B2 | 2/2015 | Gerber et al. |
| 8,965,471 B2 | 2/2015 | Lamego |
| 8,983,564 B2 | 3/2015 | Al-Ali |
| 8,986,207 B2 | 3/2015 | Li et al. |
| 8,989,831 B2 | 3/2015 | Al-Ali et al. |
| 8,996,085 B2 | 3/2015 | Kiani et al. |
| 8,998,809 B2 | 4/2015 | Kiani |
| 9,008,788 B2 | 4/2015 | Jenison |
| 9,028,429 B2 | 5/2015 | Telfort et al. |
| 9,037,207 B2 | 5/2015 | Al-Ali et al. |
| 9,050,471 B2 | 6/2015 | Skelton et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,072,870 B2 | 7/2015 | Wu et al. |
| 9,077,030 B2 | 7/2015 | Norton et al. |
| 9,078,560 B2 | 7/2015 | Schurman et al. |
| 9,079,039 B2 | 7/2015 | Carlson et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,830 B2 | 8/2015 | Galen et al. |
| 9,113,831 B2 | 8/2015 | Al-Ali |
| 9,113,832 B2 | 8/2015 | Al-Ali |
| 9,119,595 B2 | 9/2015 | Lamego |
| 9,119,597 B2 | 9/2015 | Dripps et al. |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,900 B2 | 9/2015 | Afanasewicz et al. |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,183 B2 | 9/2015 | McKenna et al. |
| 9,138,192 B2 | 9/2015 | Weber et al. |
| 9,142,117 B2 | 9/2015 | Muhsin et al. |
| 9,149,635 B2 | 10/2015 | Denison et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,173,609 B2 | 11/2015 | Nelson |
| 9,176,141 B2 | 11/2015 | Al-Ali et al. |
| 9,179,876 B2 | 11/2015 | Ochs et al. |
| 9,186,102 B2 | 11/2015 | Bruinsma et al. |
| 9,186,519 B2 | 11/2015 | Kivi |
| 9,192,312 B2 | 11/2015 | Al-Ali |

(56) References Cited

U.S. PATENT DOCUMENTS

| | | |
|---|---|---|
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,204,794 B2 | 12/2015 | Lisogurski et al. |
| 9,209,824 B2 | 12/2015 | Shen et al. |
| 9,211,072 B2 | 12/2015 | Kiani |
| 9,211,095 B1 | 12/2015 | Al-Ali |
| 9,211,411 B2 | 12/2015 | Wu et al. |
| 9,218,454 B2 | 12/2015 | Kiani et al. |
| 9,220,409 B2 | 12/2015 | Lisogurski |
| 9,220,436 B2 | 12/2015 | Sandmore et al. |
| 9,226,696 B2 | 1/2016 | Kiani |
| 9,226,709 B2 | 1/2016 | Montague |
| 9,241,662 B2 | 1/2016 | Al-Ali et al. |
| 9,245,668 B1 | 1/2016 | Vo et al. |
| 9,247,896 B2 | 2/2016 | Dripps et al. |
| 9,259,160 B2 | 2/2016 | Watson et al. |
| 9,259,185 B2 | 2/2016 | Abdul-Hafiz et al. |
| 9,267,572 B2 | 2/2016 | Barker et al. |
| 9,267,875 B2 | 2/2016 | Yap et al. |
| 9,277,880 B2 | 3/2016 | Poeze et al. |
| 9,289,136 B2 | 3/2016 | Addison et al. |
| 9,289,167 B2 | 3/2016 | Diab et al. |
| 9,295,421 B2 | 3/2016 | Kiani et al. |
| 9,348,974 B2 | 3/2016 | Goetz |
| 9,307,928 B1 | 4/2016 | Al-Ali et al. |
| 9,314,168 B2 | 4/2016 | Watson et al. |
| 9,323,894 B2 | 4/2016 | Kiani |
| D755,392 S | 5/2016 | Hwang et al. |
| 9,326,712 B1 | 5/2016 | Kiani |
| 9,327,070 B2 | 5/2016 | Skelton et al. |
| 9,333,316 B2 | 5/2016 | Kiani |
| 9,333,350 B2 | 5/2016 | Rise et al. |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,351,688 B2 | 5/2016 | Iyer et al. |
| 9,357,934 B2 | 6/2016 | Watson et al. |
| 9,357,949 B2 | 6/2016 | Drew |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |

(56) References Cited

U.S. PATENT DOCUMENTS

| | | |
|---|---|---|
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,531,811 B2 | 1/2020 | Al-Ali et al. |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,575,779 B2 | 3/2020 | Poeze et al. |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0019588 A1 | 2/2002 | Marro et al. |
| 2002/0029005 A1 | 3/2002 | Levendowski et al. |
| 2002/0038080 A1 | 3/2002 | Makarewicz et al. |
| 2002/0058864 A1 | 5/2002 | Mansfield et al. |
| 2002/0082513 A1 | 6/2002 | Ennen et al. |
| 2002/0085174 A1 | 7/2002 | Bolger et al. |
| 2002/0091335 A1 | 7/2002 | John et al. |
| 2002/0123693 A1 | 9/2002 | Lange et al. |
| 2002/0133080 A1 | 9/2002 | Apruzzese et al. |
| 2002/0183634 A1 | 12/2002 | Rantala et al. |
| 2002/0188216 A1 | 12/2002 | Kayyali et al. |
| 2003/0013975 A1 | 1/2003 | Kiani |
| 2003/0018243 A1 | 1/2003 | Gerhardt et al. |
| 2003/0055473 A1* | 3/2003 | Ramsden .................. A61F 7/10 607/109 |
| 2003/0144582 A1 | 7/2003 | Cohen et al. |
| 2003/0145854 A1 | 8/2003 | Hickle |
| 2003/0156288 A1 | 8/2003 | Barnum et al. |
| 2003/0158587 A1 | 8/2003 | Esteller et al. |
| 2003/0204148 A1 | 10/2003 | Lange et al. |
| 2003/0212312 A1 | 11/2003 | Coffin, IV et al. |
| 2003/0069516 A1 | 12/2003 | Becker et al. |
| 2003/0225323 A1 | 12/2003 | Kiani et al. |
| 2004/0030258 A1* | 2/2004 | Williams ................ A61B 5/291 600/544 |
| 2004/0039271 A1 | 2/2004 | Blank et al. |
| 2004/0073098 A1 | 4/2004 | Geva et al. |
| 2004/0073129 A1 | 4/2004 | Caldwell et al. |
| 2004/0082862 A1 | 4/2004 | Chance |
| 2004/0082876 A1 | 4/2004 | Viertio-Oja et al. |
| 2004/0106163 A1 | 6/2004 | Workman, Jr. et al. |
| 2004/0167418 A1 | 8/2004 | Nguyen et al. |
| 2004/0193068 A1 | 9/2004 | Burton et al. |
| 2004/0243017 A1 | 12/2004 | Causevic |
| 2004/0267153 A1 | 12/2004 | Bergethon |
| 2005/0010116 A1 | 1/2005 | Korhonen et al. |
| 2005/0055276 A1 | 3/2005 | Kiani et al. |
| 2005/0059899 A1 | 3/2005 | Merilainen et al. |

(56) References Cited

U.S. PATENT DOCUMENTS

| | | |
|---|---|---|
| 2005/0081847 A1 | 4/2005 | Lee et al. |
| 2005/0090754 A1 | 4/2005 | Wolff et al. |
| 2005/0113704 A1 | 5/2005 | Lawson et al. |
| 2005/0119547 A1 | 6/2005 | Shastri et al. |
| 2005/0217674 A1 | 10/2005 | Burton et al. |
| 2005/0234317 A1 | 10/2005 | Kiani |
| 2005/0277819 A1 | 12/2005 | Kiani et al. |
| 2005/0280531 A1* | 12/2005 | Fadem .................. A61B 5/282 340/539.12 |
| 2006/0073719 A1 | 4/2006 | Kiani |
| 2006/0084852 A1 | 4/2006 | Mason et al. |
| 2006/0100538 A1 | 5/2006 | Genger et al. |
| 2006/0116556 A1 | 6/2006 | Duhamel |
| 2006/0161054 A1 | 7/2006 | Reuss et al. |
| 2006/0167368 A1 | 7/2006 | Sarkela |
| 2006/0189861 A1 | 8/2006 | Chen et al. |
| 2006/0189871 A1 | 8/2006 | Al-Ali et al. |
| 2006/0217628 A1 | 9/2006 | Huiku |
| 2006/0235315 A1 | 10/2006 | Akselrod |
| 2006/0241356 A1 | 10/2006 | Flaherty |
| 2006/0241562 A1 | 10/2006 | Erwin et al. |
| 2006/0293608 A1 | 12/2006 | Rothman et al. |
| 2007/0010755 A1 | 1/2007 | Sarkela et al. |
| 2007/0010756 A1 | 1/2007 | Viertio-Oja |
| 2007/0010795 A1 | 1/2007 | Sarkela et al. |
| 2007/0073116 A1 | 3/2007 | Kiani et al. |
| 2007/0100218 A1* | 5/2007 | Sweitzer ............ A61B 5/14551 600/323 |
| 2007/0180140 A1 | 8/2007 | Welch et al. |
| 2007/0185407 A1 | 8/2007 | Xu et al. |
| 2007/0208269 A1 | 9/2007 | Mumford et al. |
| 2007/0244377 A1 | 10/2007 | Cozad et al. |
| 2007/0244721 A1 | 10/2007 | Sackner-Bernstein et al. |
| 2007/0249952 A1 | 10/2007 | Rubin et al. |
| 2007/0282478 A1 | 12/2007 | Al-Ali et al. |
| 2008/0017800 A1 | 1/2008 | Benni |
| 2008/0064965 A1 | 3/2008 | Jay et al. |
| 2008/0094228 A1 | 4/2008 | Welch et al. |
| 2008/0139953 A1* | 6/2008 | Baker ................ A61B 5/14542 600/509 |
| 2008/0200783 A9 | 8/2008 | Blank et al. |
| 2008/0200786 A1 | 8/2008 | Berndsen |
| 2008/0221418 A1 | 9/2008 | Al-Ali et al. |
| 2008/0221461 A1 | 9/2008 | Zhou et al. |
| 2008/0234597 A1 | 9/2008 | Becker et al. |
| 2008/0255469 A1 | 10/2008 | Shieh et al. |
| 2008/0285029 A1 | 11/2008 | Benni et al. |
| 2008/0294063 A1 | 11/2008 | Bibian et al. |
| 2008/0300469 A1 | 12/2008 | Kuo et al. |
| 2008/0300473 A1 | 12/2008 | Benni |
| 2008/0300474 A1 | 12/2008 | Benni et al. |
| 2009/0018427 A1 | 1/2009 | Causevic et al. |
| 2009/0018429 A1 | 1/2009 | Saliga et al. |
| 2009/0036759 A1 | 2/2009 | Ault et al. |
| 2009/0036799 A1 | 2/2009 | Sandhu et al. |
| 2009/0088619 A1 | 4/2009 | Turner et al. |
| 2009/0093687 A1 | 4/2009 | Telfort et al. |
| 2009/0095926 A1 | 4/2009 | MacNeish, III |
| 2009/0108205 A1 | 4/2009 | Duffy et al. |
| 2009/0182209 A1 | 7/2009 | Benni |
| 2009/0182394 A1* | 7/2009 | Bachinski ............ A61N 1/0452 607/59 |
| 2009/0247924 A1 | 10/2009 | Lamego et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2009/0281403 A1 | 11/2009 | Benni |
| 2009/0299157 A1 | 12/2009 | Telfort et al. |
| 2010/0004518 A1 | 1/2010 | Vo et al. |
| 2010/0030040 A1 | 2/2010 | Poeze et al. |
| 2010/0041962 A1 | 2/2010 | Causevie et al. |
| 2010/0049018 A1 | 2/2010 | Duffy et al. |
| 2010/0063438 A1* | 3/2010 | Bengtsson ............ A61B 5/349 340/691.4 |
| 2010/0069725 A1 | 3/2010 | Al-Ali |
| 2010/0099964 A1 | 4/2010 | O'Reilly et al. |
| 2010/0113897 A1* | 5/2010 | Brenneman ........ A61B 5/14532 29/428 |
| 2010/0130840 A1 | 5/2010 | Isaacson |
| 2010/0234718 A1 | 9/2010 | Sampath et al. |
| 2010/0261979 A1 | 10/2010 | Al-Ali et al. |
| 2010/0270257 A1 | 10/2010 | Wachman et al. |
| 2010/0317936 A1 | 12/2010 | Al-Ali et al. |
| 2011/0001605 A1 | 1/2011 | Kiani et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0087083 A1 | 4/2011 | Poeze et al. |
| 2011/0105854 A1 | 5/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2011/0172967 A1 | 7/2011 | Al-Ali et al. |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2011/0237924 A1 | 9/2011 | McGusty et al. |
| 2011/0237969 A1 | 9/2011 | Eckerbom et al. |
| 2012/0029308 A1* | 2/2012 | Paquet .................... A61B 5/01 600/549 |
| 2012/0041316 A1 | 2/2012 | Al Ali et al. |
| 2012/0046557 A1 | 2/2012 | Kiani |
| 2012/0059267 A1 | 3/2012 | Lamego et al. |
| 2012/0083673 A1 | 4/2012 | Al-Ali et al. |
| 2012/0088984 A1 | 4/2012 | Al-Ali et al. |
| 2012/0116175 A1 | 5/2012 | Al-Ali et al. |
| 2012/0123231 A1 | 5/2012 | O'Reilly |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0227739 A1 | 9/2012 | Kiani |
| 2012/0265039 A1 | 10/2012 | Kiani |
| 2012/0283524 A1 | 11/2012 | Kiani et al. |
| 2012/0286955 A1 | 11/2012 | Welch et al. |
| 2012/0296178 A1 | 11/2012 | Lamego et al. |
| 2012/0302894 A1 | 11/2012 | Diab et al. |
| 2012/0316459 A1 | 12/2012 | Abreu |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0030267 A1 | 1/2013 | Lisogurski |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0079610 A1 | 3/2013 | Al-Ali |
| 2013/0096405 A1 | 4/2013 | Garfio |
| 2013/0096936 A1 | 4/2013 | Sampath et al. |
| 2013/0104288 A1 | 5/2013 | Schlottau et al. |
| 2013/0109935 A1 | 5/2013 | Al-Ali et al. |
| 2013/0162433 A1 | 6/2013 | Muhsin et al. |
| 2013/0178749 A1 | 7/2013 | Lamego |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | O'Neil et al. |
| 2013/0317327 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0324817 A1 | 12/2013 | Diab |
| 2013/0331670 A1 | 12/2013 | Kiani |
| 2013/0338461 A1 | 12/2013 | Lamego et al. |
| 2013/0345921 A1 | 12/2013 | Al-Ali et al. |

(56) References Cited

U.S. PATENT DOCUMENTS

| | | |
|---|---|---|
| 2014/0012100 A1 | 1/2014 | Al-Ali et al. |
| 2014/0012153 A1 | 1/2014 | Greenwald |
| 2014/0025306 A1 | 1/2014 | Weber et al. |
| 2014/0031650 A1 | 1/2014 | Weber et al. |
| 2014/0034353 A1 | 2/2014 | Al-Ali et al. |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0073167 A1 | 3/2014 | Al-Ali et al. |
| 2014/0077956 A1 | 3/2014 | Sampath et al. |
| 2014/0081097 A1 | 3/2014 | Al-Ali et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142399 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0155712 A1 | 6/2014 | Lamego et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0257073 A1 | 9/2014 | Machon et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275875 A1 | 9/2014 | Su et al. |
| 2014/0275881 A1 | 9/2014 | Lamego et al. |
| 2014/0275893 A1 | 9/2014 | Booker |
| 2014/0288400 A1 | 9/2014 | Diab et al. |
| 2014/0296664 A1 | 10/2014 | Bruinsma et al. |
| 2014/0303459 A1 | 10/2014 | Wada et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0336481 A1 | 11/2014 | Shakespeare et al. |
| 2014/0357966 A1 | 12/2014 | Al-Ali et al. |
| 2014/0371548 A1 | 12/2014 | Al-Ali et al. |
| 2014/0371632 A1 | 12/2014 | Al-Ali et al. |
| 2014/0378784 A1 | 12/2014 | Kiani et al. |
| 2015/0005600 A1 | 1/2015 | Blank et al. |
| 2015/0011857 A1 | 1/2015 | Henson et al. |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0025406 A1 | 1/2015 | Al-Ali |
| 2015/0032029 A1 | 1/2015 | Al-Ali et al. |
| 2015/0038812 A1 | 2/2015 | Ayaz et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0140863 A1 | 5/2015 | Al-Ali et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0196249 A1 | 7/2015 | Brown et al. |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272496 A1 | 10/2015 | Klappert et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank et al. |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali et al. |
| 2016/0143548 A1 | 5/2016 | Al-Ali |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |

(56) References Cited

U.S. PATENT DOCUMENTS

| | | |
|---|---|---|
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0021099 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego |
| 2017/0202490 A1 | 7/2017 | Al-Ali et al. |
| 2017/0224262 A1 | 8/2017 | Al-Ali |
| 2017/0228516 A1 | 8/2017 | Sampath |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani |
| 2017/0367632 A1 | 12/2017 | Al-Ali et al. |
| 2018/0008146 A1 | 1/2018 | Al-Ali et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0103874 A1 | 4/2018 | Lee et al. |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0199871 A1 | 7/2018 | Pauley et al. |
| 2018/0213583 A1 | 7/2018 | Al-Ali |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0289325 A1 | 10/2018 | Poeze et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0117070 A1 | 4/2019 | Muhsin et al. |
| 2019/0133525 A1 | 5/2019 | Al-Ali et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |

FOREIGN PATENT DOCUMENTS

| | | |
|---|---|---|
| EP | 0 638 193 | 2/1995 |
| EP | 1 250 886 | 10/2002 |
| EP | 1 624 798 | 11/2004 |
| EP | 1 779 257 | 5/2007 |
| JP | 2010-088928 | 4/2010 |
| WO | WO 91/009372 | 6/1991 |
| WO | WO 91/019453 | 12/1991 |
| WO | WO 92/002176 | 2/1992 |
| WO | WO 93/021615 | 10/1993 |
| WO | WO 99/008589 | 2/1999 |
| WO | WO 00/021432 | 10/1999 |
| WO | WO 00/021435 | 4/2000 |
| WO | WO 00/056211 | 9/2000 |
| WO | WO 00/056212 | 9/2000 |
| WO | WO 01/030414 | 5/2001 |
| WO | WO 2004/028362 | 4/2004 |

(56) References Cited

FOREIGN PATENT DOCUMENTS

| WO | WO 2004/054441 | 7/2004 |
|---|---|---|
| WO | WO 2007/059248 | 5/2007 |
| WO | WO 2007/140535 | 12/2007 |
| WO | WO 2007/140536 | 12/2007 |
| WO | WO 2007/149553 | 12/2007 |
| WO | WO 2008/015449 | 2/2008 |
| WO | WO 2008/040846 | 4/2008 |
| WO | WO 2008/043365 | 4/2008 |
| WO | WO 2008/109694 | 9/2008 |
| WO | WO 2008/109699 | 9/2008 |
| WO | WO 2008/119029 | 10/2008 |
| WO | WO 2008/119031 | 10/2008 |
| WO | WO 2008/122082 | 10/2008 |
| WO | WO 2008/138340 | 11/2008 |
| WO | WO 2016/057553 | 4/2016 |

OTHER PUBLICATIONS

US 2022/0192529 A1, 06/2022, Al-Ali et al. (withdrawn)
Partial International Search Report for International Application No. PCT/US2011/053540, dated Jan. 30, 2012, in 4 pages.
International Search Report for International Application No. PCT/US2011/053540, dated May 3, 2012, in 14 pages.
International Preliminary Report on Patentability for International Application No. PCT/US2011/053540, dated Apr. 11, 2013, in 9 pages.
International Search Report and Written Opinion received in PCT application No. PCT/US2015/054293, dated Dec. 17, 2015.
International Preliminary Report on Patentability and Written Opinion received in PCT application No. PCT/US2015/054293, dated Apr. 11, 2017.

* cited by examiner

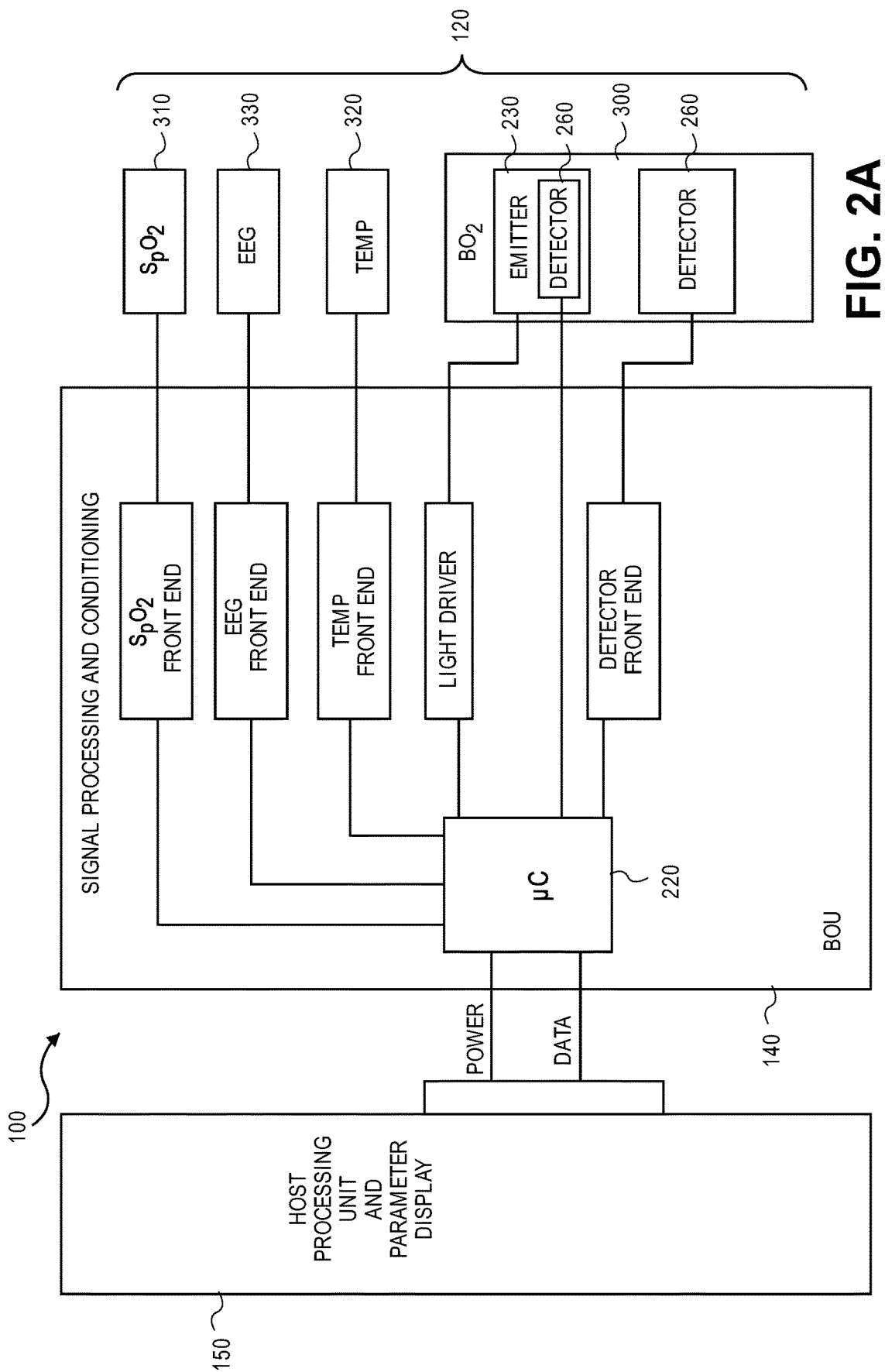

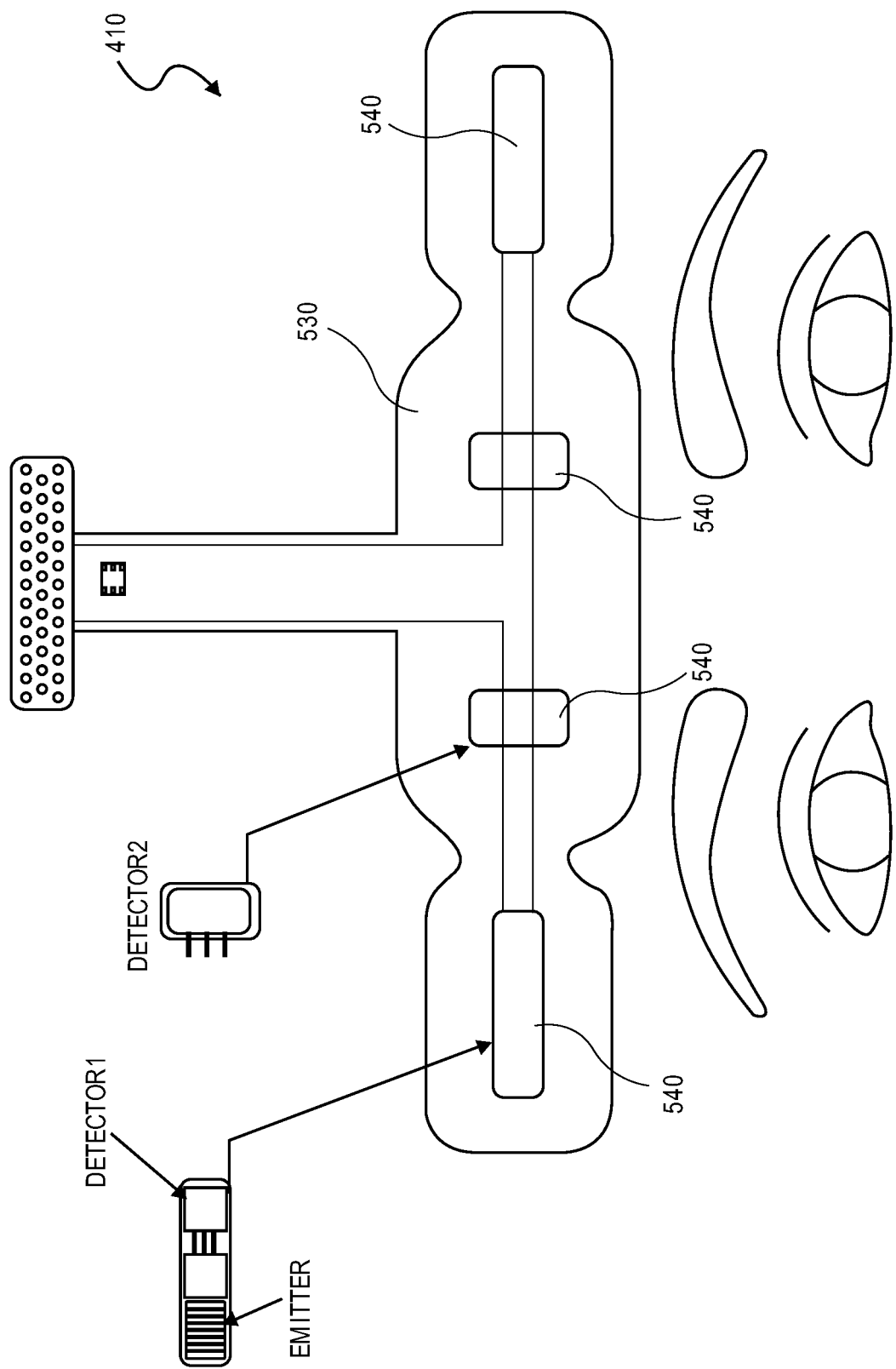

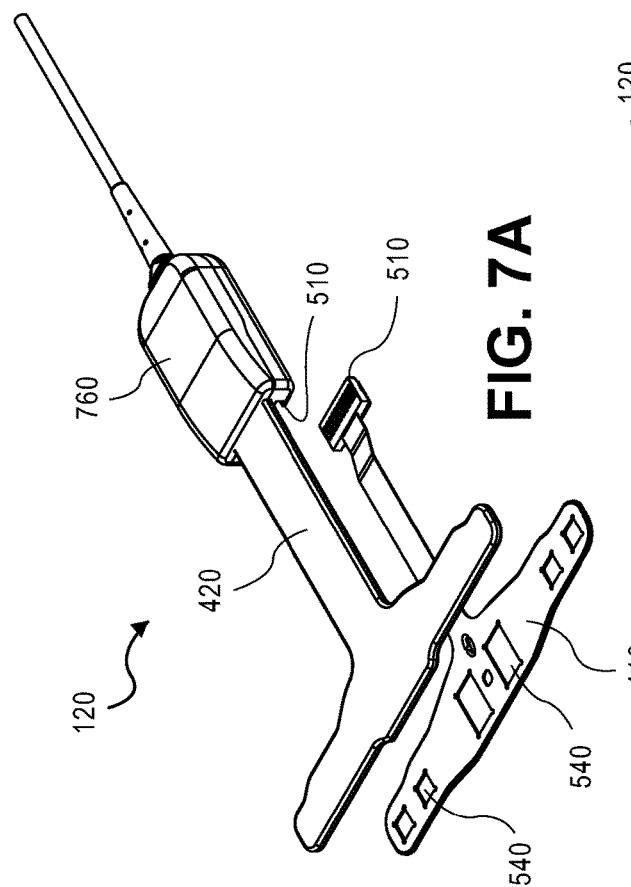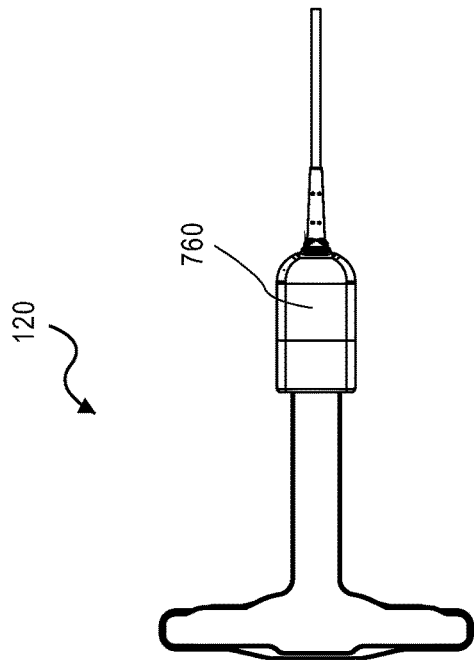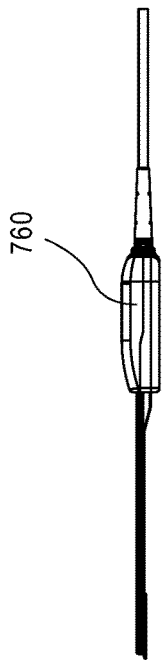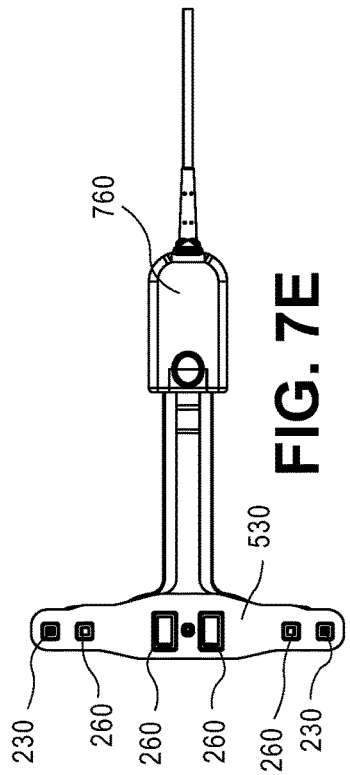

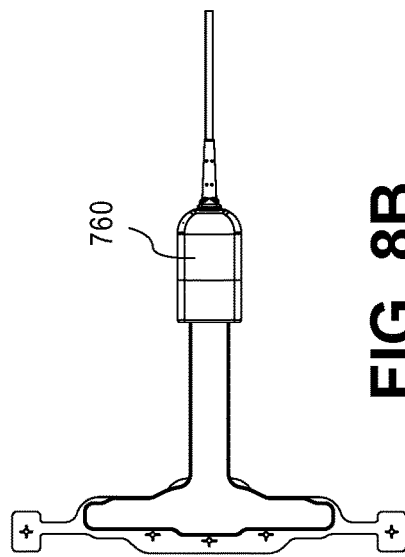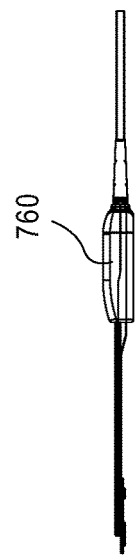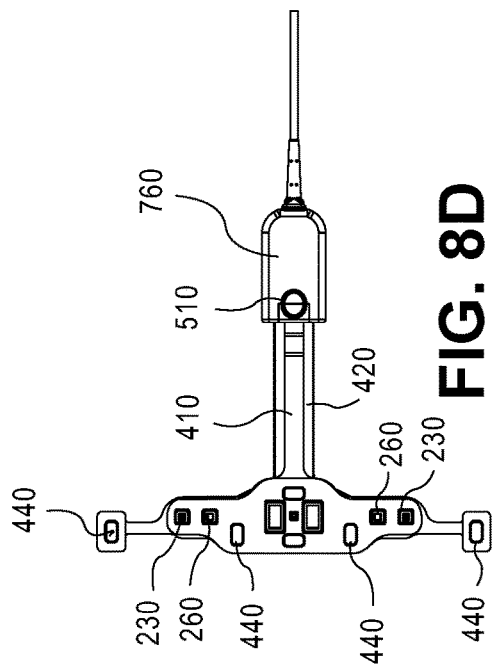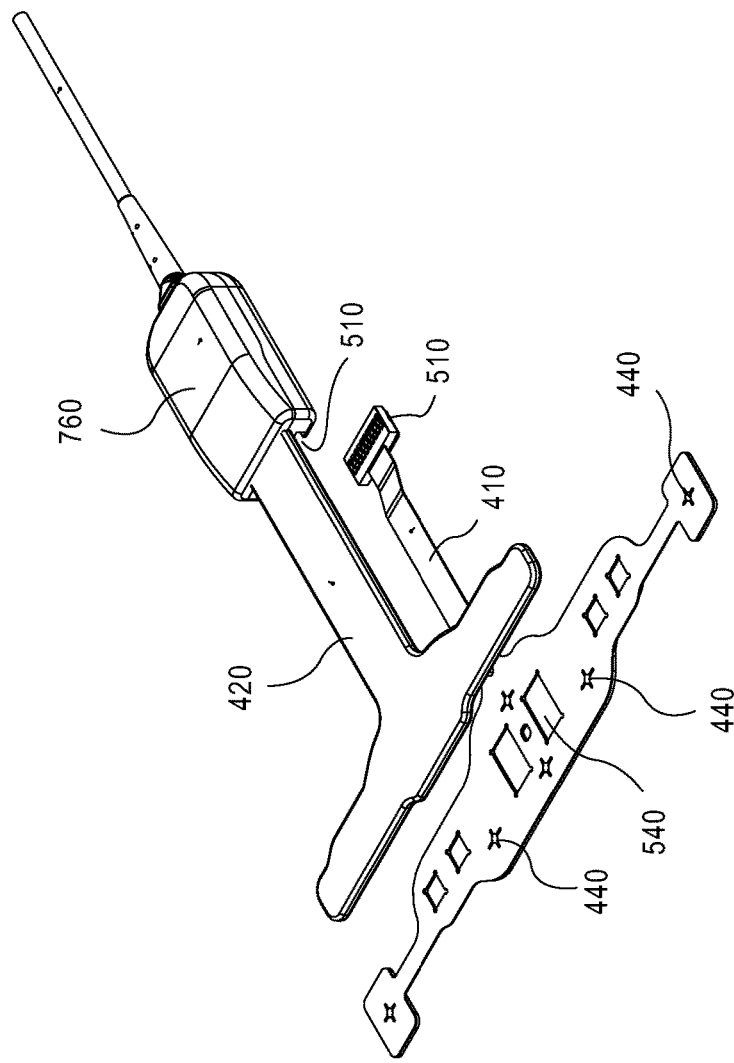
FIG. 8B
FIG. 8C
FIG. 8D
FIG. 8A

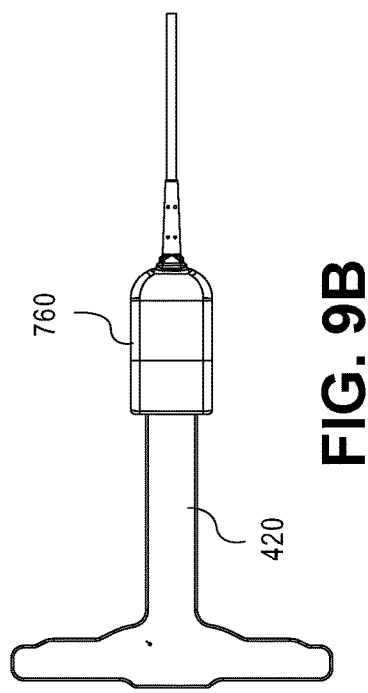
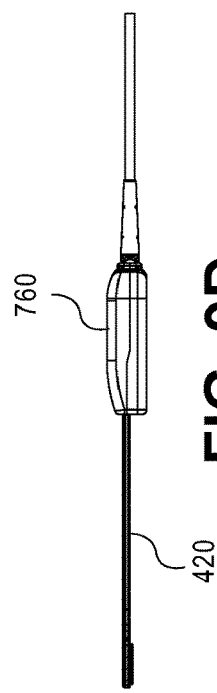
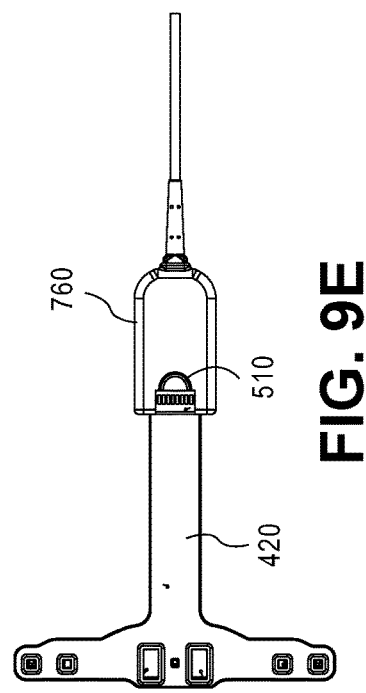
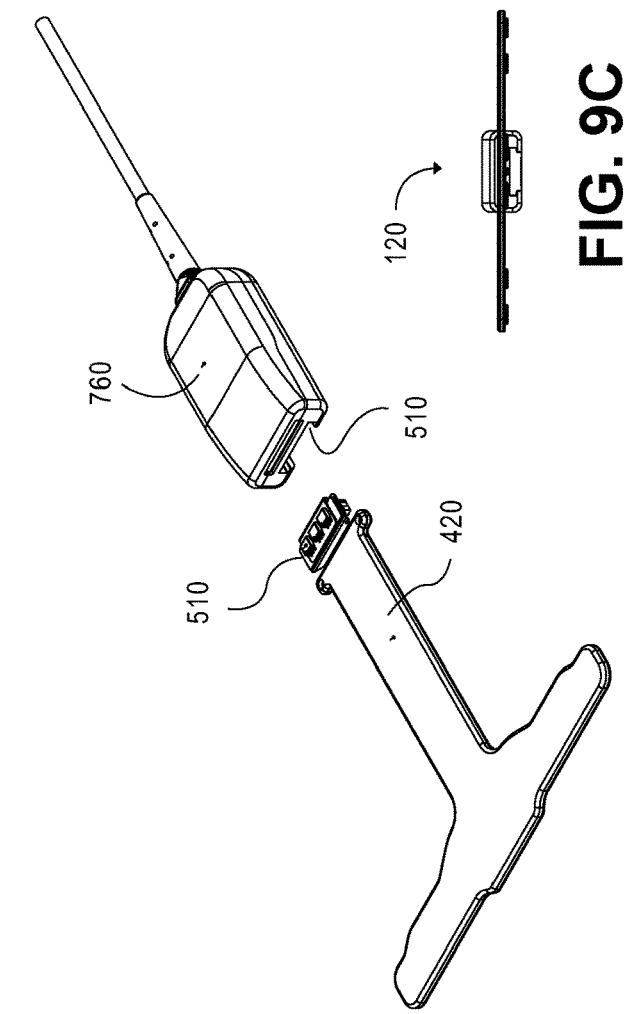

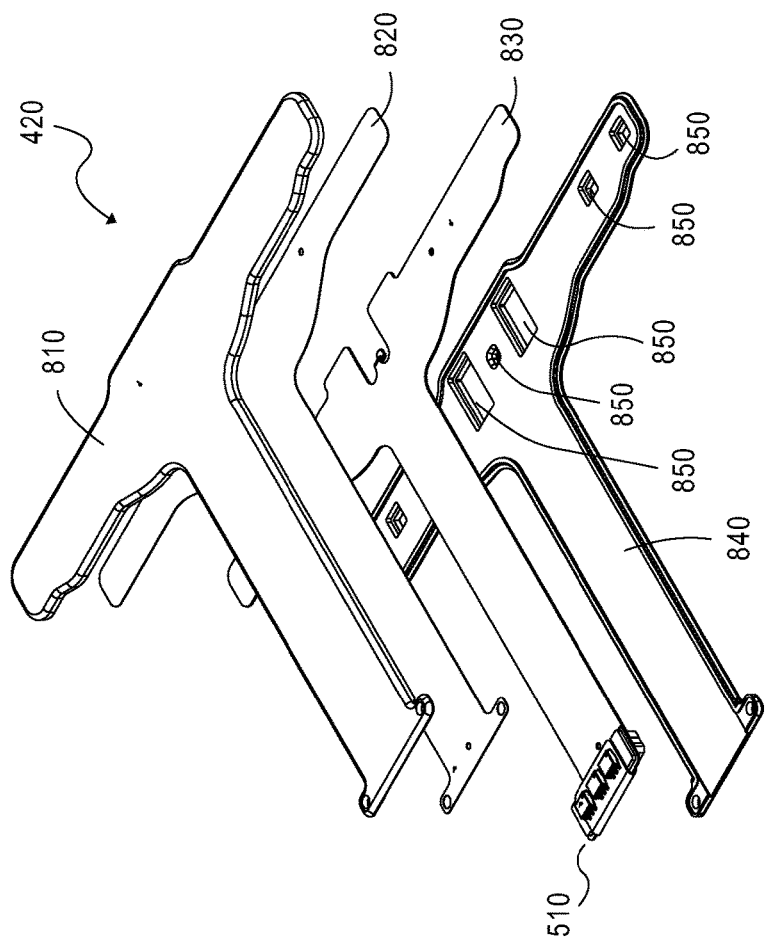
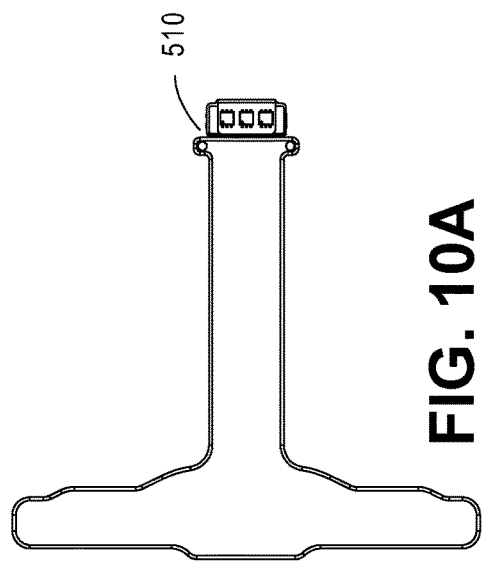
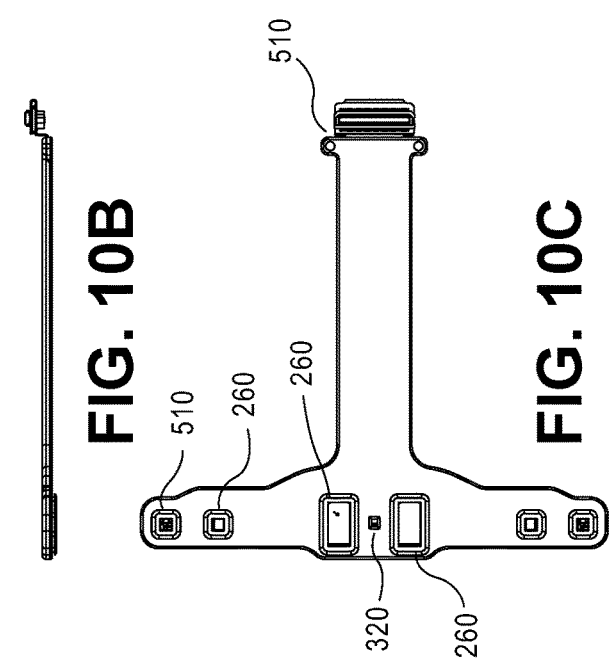

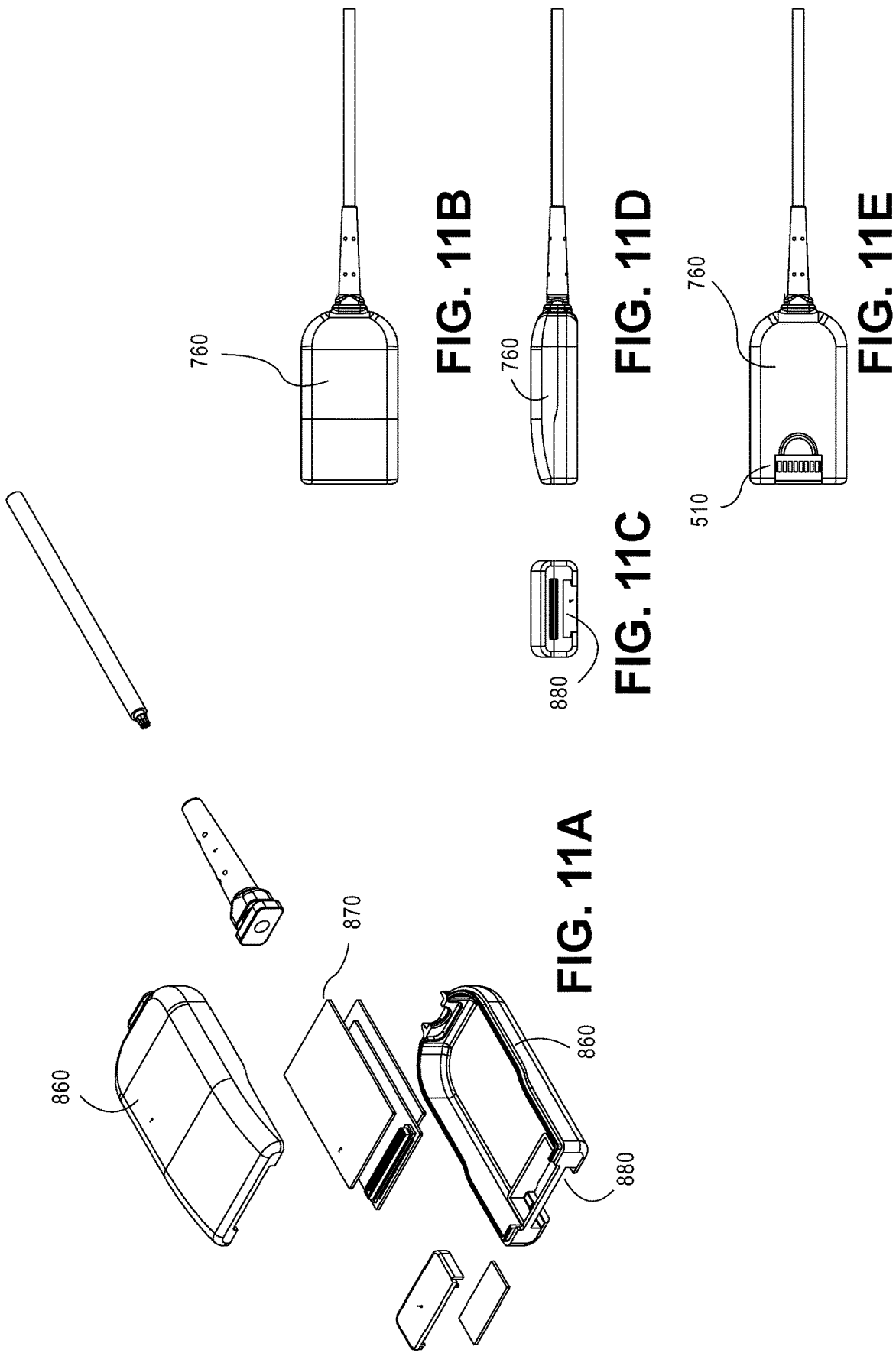

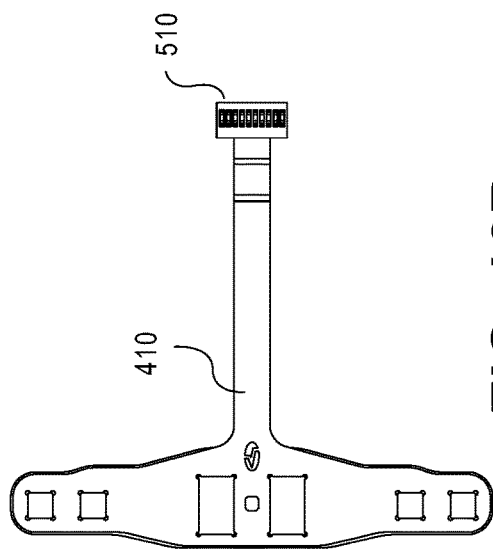
FIG. 12B
FIG. 12C
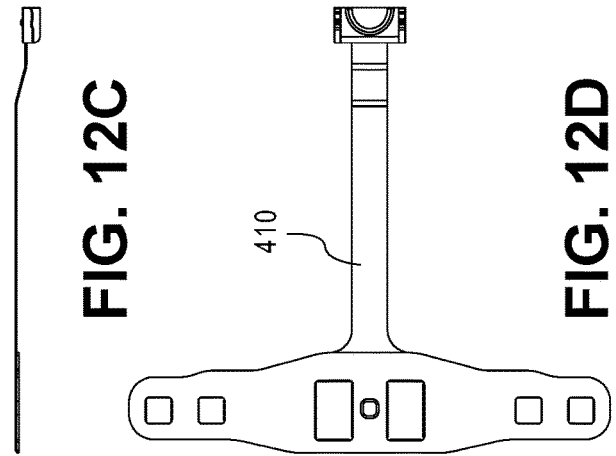
FIG. 12D
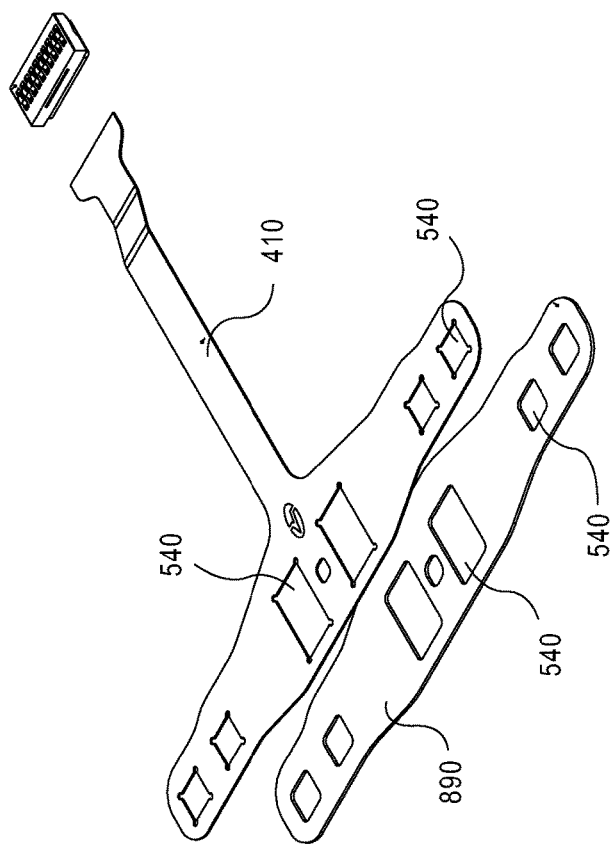
FIG. 12A

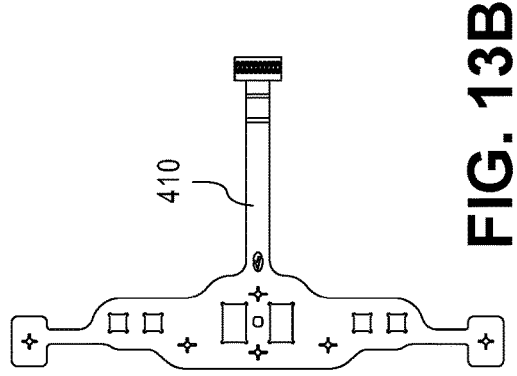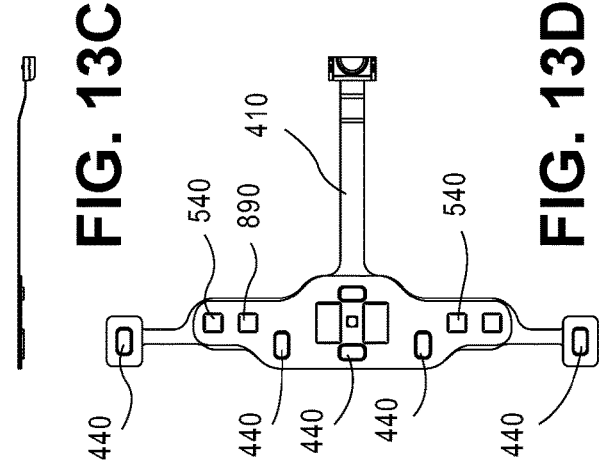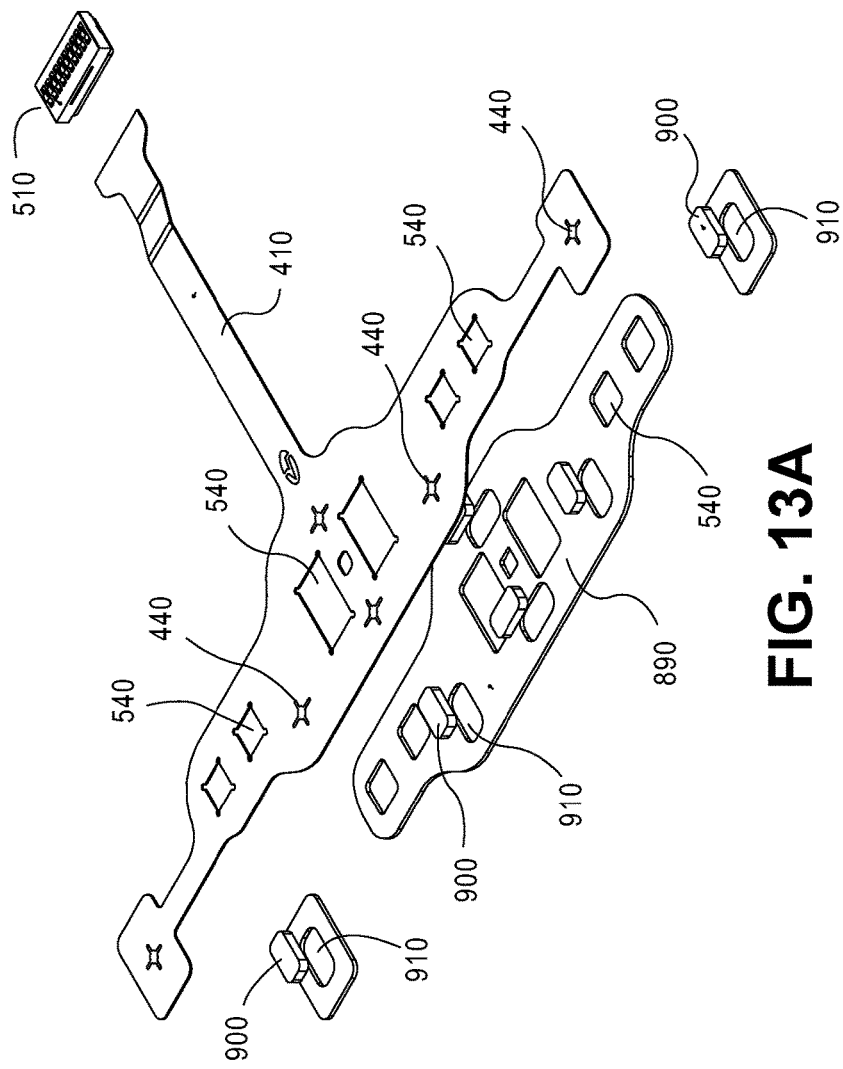

DEPTH OF CONSCIOUSNESS MONITOR INCLUDING OXIMETER

PRIORITY CLAIM

This application is a continuation of U.S. patent application Ser. No. 15/389,285, titled "Depth of Consciousness Monitor Including Oximeter," filed Dec. 22, 2016, which is a continuation of U.S. patent application Ser. No. 14/470,819, titled "Depth of Consciousness Monitor Including Oximeter," filed Aug. 27, 2014, now U.S. Pat. No. 9,538,949, which is a continuation of U.S. patent application Ser. No. 13/246,725, titled "Depth of Consciousness Monitor Including Oximeter," filed Sep. 27, 2011, now U.S. Pat. No. 8,821,397 which claims the benefit of priority under 35 U.S.C. § 119(e) of the following U.S. Provisional Patent Application No. 61/387,457, titled "Depth of Consciousness Monitor Including Oximeter," filed on Sep. 28, 2010, the disclosures of each of which are incorporated in their entirety by referenced herein.

REFERENCE TO RELATED APPLICATIONS

This application is related to U.S. Provisional Patent Application No. 61/387,426, titled "Magnetic Electrical Connector For Patient Monitors," filed on Sep. 28, 2010, and incorporates that application by reference herein in its entirety.

FIELD OF THE DISCLOSURE

The present disclosure relates to the field of oximetry. More specifically, the disclosure relates to oximetry technologies for depth of consciousness monitoring.

BACKGROUND OF THE DISCLOSURE

General anesthesia is often used to put patients to sleep and block pain and memory during medical or diagnostic procedures. While extremely useful to caregivers, general anesthesia is not risk free, and thus, caregivers seek to maintain a depth of consciousness consistent with the needs of a particular medical procedure. In short, there is a desire to avoid over and under dosing. However, as a patient's depth of consciousness may change from minute to minute, caregivers often employ a host of monitoring technologies to attempt to periodically, sporadically, or continually ascertain the wellness and consciousness of a patient. For example, caregivers may desire to monitor one or more of a patient's temperature, electroencephalogram or EEG, brain oxygen saturation, stimulus response, electromyography or EMG, respiration, body oxygen saturation or other blood analytes, pulse, hydration, blood pressure, perfusion, or other parameters or combinations of parameters. For many of the foregoing, monitoring technologies are individually readily available and widely used, such as, for example, pulse oximeters, vital signs monitors, and the like.

In their depth of consciousness monitoring, caregivers may also use recording devices to acquire EEG signals. For example, caregivers place electrodes on the skin of the forehead to detect electrical activity produced by the firing of neurons within the brain. From patterns in the electrical activity, caregivers attempt to determine, among other things, the state of consciousness of the brain. Caregivers may also use cerebral oximeters to determine the percentage of oxygenation of the hemoglobin in the cerebral cavity inside the skull. Cerebral oximetry is different from conventional pulse oximetry, which detects the oxygenation of blood in the body arteries. However, like pulse oximetry, caregivers place sensors on the body, in this case on the forehead, that emit radiation and detect the radiation after attenuation by body tissue. This attenuated signal includes information relating to the blood oxygenation of the brain. Directly measuring the blood oxygenation of the brain, or at least measuring physiological parameters indicative of the blood oxygenation of the brain, provides information about the state of brain function, such as, for example, brain oxygen consumption, not available by measurement parameters that determine only the oxygenation of the blood feeding the brain or by monitoring the brain's electrical activity.

Today, there are several approaches to implementing a cerebral oximeter. One approach includes placing emitters on the forehead and spacing detectors on the forehead at different distances from the emitters. The emitters emit radiation at two or four different wavelengths and the detectors output signals representing the detected attenuated radiation. An instrument compares a DC signal from the different detectors and uses the difference as a basis for measurement. The underlying assumption appears to be that the closer detector provides an indication of oxygen saturation of the tissue outside the cerebral cavity, while the further detector provides an indication of the oxygen saturation of the tissue outside and inside the cerebral cavity. Subtraction of the two is hoped to provide an indication of just cerebral oxygenation. In any event, caregivers use a rising or falling trend in this difference to make deductions about the cerebral oxygen status in the patient. In some cases, instruments employing four wavelength systems also seek an output value of oxygenation, as opposed to just a trend of the difference signal. The foregoing approaches appear to be consistent with commercially available instruments from Somanetics Corporation of Troy, Mich. and CAS Medical Systems, Inc. of Branford Conn. A significant drawback to each of these approaches includes the cost of the instrumentation and sensors is often prohibitively high.

Another approach to a cerebral oximeter includes deep tissue imaging. For example, this type of research exposes high frequency light to the forehead and attempts to measure time of arrival and scattering/absorption coefficients. While primarily still in a research phase, it appears that the instrumentation could be less expensive than that disclosed above, perhaps even half the cost. However, even at that savings, this type of cerebral oximeter is still primarily in the research and development phase and still relatively costly. For example, the multiple optical benches provided in a single instrument generally associated with this type of design could cost more than three thousand dollars each.

Complicating the foregoing discussion is the realization that there is limited space on a patient's head for each of the different sensors. Particularly, where the forehead is the optimal measurement site in which to position EEG and brain oximetry sensors, drawbacks occur. For example, given the forehead's relatively small size, the forehead provides space for placement of a few sensors at the same time.

SUMMARY OF THE DISCLOSURE

Based on at least the foregoing, the present disclosure seeks to overcome some or all of the drawbacks discussed above and provide additional advantages over any prior technologies. The present disclosure describes embodiments of noninvasive methods, devices, and systems for monitoring depth of consciousness through brain electrical activity and the oxygenation of the brain. Additional embodiments include monitoring of heartbeat, arterial oxygenation, venous oxygenation, temperature, and other physiological patient characteristics. For example, the present disclosure includes a combination forehead sensor having EEG and brain oximetry components. In an embodiment, the EEG components include electrical leads and the brain oximetry components include a plurality of light sources and detectors. Moreover, in an embodiment the forehead sensor includes a multisite forehead sensor configured to be positioned above the eyebrows of a patient with connecting devices and cables traveling over the head and conveniently away from the body. Such positioning provides an ergonomic sensor along with increased safety from potential inadvertent interference by the patient or caregiver.

In an embodiment, a light source system of the sensor includes low cost optical benches having self contained internal emission detectors, light integrators or prisms, mirrors and the like. For example, in an embodiment, a light source includes a cap configured to reflect light toward a splitting mirror focusing light to both an internal emission detector for evaluation of the intensity of the emitted light and an aperture for directing the light into the patient's tissue. The light source may also include opaque or other surfaces or walls configured to appropriately direct emitted light.

Further embodiments may transform a commercially available pulse oximeter into a brain oximetry unit. For example, a processing device may advantageously connect to a sensor or other data input connection of a pulse oximeter to, for example, acquire power and open communication between the devices. In an embodiment, the sensor would include components for measuring the attenuation thereof. In an embodiment, the sensor would output a signal that represents the attenuated light. This signal would be similar to the output of a conventional pulse oximeter sensor in that both attempt to be indicative of light attenuation.

The signal could then be transmitted to the pulse oximeter for processing, conditioning and displaying of the brain oxygenation on a monitor of the pulse oximeter. A conventional pulse oximeter would be readily adaptable to process and display information from a brain oximeter sensor because the signals output by sensors of both devices are similar in nature (as both are output from photodiode light detectors detecting light attenuated by tissue). Modifications to the oximeter may advantageously include the algorithms used to analyze the signal from the sensors as cerebral oximeters may advantageously use different wavelengths, frequencies, and different comparing and analysis techniques to determine oxygenation. However, one of ordinary skill will recognize from the disclosure herein that algorithm changes often are much more straightforward and price competitive than significant hardware changes. This is especially the case when updating an already-installed base of monitors.

In another embodiment, a forehead sensor for monitoring the depth of consciousness of a patient is disclosed comprising a brain oxygenation sensor that includes at least one light source and two detectors, an eeg sensor that includes electrical leads that make contact with the skin of the patient's forehead, a reusable portion that houses the light source and detectors of the brain oxygenation sensor and a disposable portion that houses a plurality of EEG electrodes and is removably connectable to the reusable portion. The connector of the forehead sensor may also connect to the disposable portion and the reusable portion and house the majority of the curicutiry and processing components for the EEG sensor and the brain oxygenation sensor. In embodiment, an interface between the connector and the disposable portion may allow the disposable portion to be removably attached to the connector. The light source or detector may also have a lip around their edge. In an embodiment, the reusable portion is directly connected to the disposable portion.

In an embodiment, a system for monitoring the depth of consciousness of a patient is disclosed comprising a forehead sensor that includes a brain oxygenation sensor and a conventional pulse oximeter loaded with software for displaying data related to the blood oxygenation level of the brain cavity data processed by the forehead sensor. In an embodiment, the conventional pulse oximeter may provide power to the sensor and be capable of communicating data with the sensor or provide the drive signal and process the signal from the detector of the brain oxygenation sensor. The forehead sensor may also contain all of the components for processing the sign from detectors of the brain oxygenation sensor.

In another embodiment, a light source for a brain oxygenation sensor is disclosed comprising a substrate, emitters attached to the substrate for emitting light with at least two different wavelengths, a detector for detecting emitted light before it is attenuated by tissue, a cap connected to the substrate, and an aperture for the emitted light to exit the light source and enter the tissue site. The emitters may be LED's. In an embodiment a light diffusing material may be placed between the emitters and tissue site to scatter light. The light diffusing material may also be between the emitters and the detector and be made from a glass or epoxy that fills in around the emitters and detector. In an embodiment, the cap may be reflective or non-reflective. In another embodiment, a splitting mirror may direct light either to the detector or the aperture. In a further embodiment, a temperature sensor may be connected to the substrate.

For purposes of summarizing the disclosure, certain aspects, advantages and novel features of the disclosure have been described herein. Of course, it is to be understood that not necessarily all such aspects, advantages or features will be embodied in any particular embodiment of the disclosure.

BRIEF DESCRIPTION OF THE DRAWINGS

The following drawings and the associated descriptions are provided to illustrate embodiments of the present disclosure and do not limit the scope of the claims.

FIG. 2A-2B illustrate block diagrams of embodiments of the brain oximetry unit of FIG. 1A.

FIGS. 3A, 3N, and 3O illustrate embodiments of the forehead a sensor including reusable and disposable portions mated together.

FIGS. 3D-3M illustrate embodiments of the disposable portion including EEG, temperature and other parameter measuring components.

FIG. 4A-D illustrate perspective and side views of a light source of the cerebral oximeter according to embodiments of the present disclosure.

FIG. 4O illustrates a side view of the light source with an angled substrate according to an embodiment of the present disclosure.

FIGS. 7A-7E illustrate various embodiments and views of the forehead sensor of FIG. 6.

FIG. 7A illustrates a perspective view of the sensor and connector with the disposable portion of the forehead sensor detached from the connector.

FIG. 7B illustrates a top view of the forehead sensor with the disposable and reusable portion of the sensor connected.

FIG. 7C illustrates a side view of the forehead sensor with both the disposable and reusable portion of the sensor connected.

FIG. 7D illustrates a front view of the forehead sensor with both the disposable and reusable portion of the sensor connected.

FIG. 7E illustrates a bottom view of the forehead sensor with the disposable and reusable portion connected.

FIGS. 8A-8D illustrate various embodiments and views of the forehead sensor that include an EEG sensor.

FIG. 8A illustrates a perspective view of the sensor and connector with the disposable portion of the forehead sensor detached from the connector.

FIG. 8B illustrates a top view of the forehead sensor with the disposable and reusable portion of the sensor connected.

FIG. 8C illustrates a side view of the forehead sensor with both the disposable and reusable portion of the sensor connected.

FIG. 8D illustrates a bottom view of the forehead sensor with the disposable and reusable portion connected.

FIGS. 9A-9E illustrate various embodiments and views of the reusable portion of the forehead sensor.

FIG. 9A illustrates a perspective view of the reusable portion and connector of the forehead sensor with the reusable portion detached from the connector.

FIG. 9B illustrates a top view of the reusable portion of the forehead sensor.

FIG. 9C illustrates a side view reusable portion of the forehead sensor.

FIG. 9D illustrates a front view of the reusable portion of the forehead sensor.

FIG. 9E illustrates a bottom view of the reusable portion of the forehead sensor.

FIGS. 10A-10D illustrate various embodiments and views of the reusable portion of the forehead sensor.

FIG. 10A illustrates a top view of the reusable portion of the forehead sensor.

FIG. 10B illustrates a side view reusable portion of the forehead sensor.

FIG. 10C illustrates a bottom view of the reusable portion of the forehead sensor.

FIG. 10D illustrates an exploded perspective view showing an embodiment of the various layers of the reusable portion of the forehead sensor.

FIGS. 11A-11E illustrate various embodiments and views of the connector of the forehead sensor.

FIG. 11A illustrates an exploded perspective view of the various components of the connector.

FIG. 11B illustrates a top view of the connector.

FIG. 11C illustrates a front view of the connector.

FIG. 11D illustrates a side view of the connector.

FIG. 11E illustrates a bottom view of the connector.

FIGS. 12A-12D illustrate various embodiments and views of the disposable portion of the forehead sensor.

FIG. 12A illustrates a perspective view of the disposable portion of the forehead sensor with a detached adhesive layer.

FIG. 12B illustrates a top view of the disposable portion of the forehead sensor.

FIG. 12C illustrates a side view of the disposable portion of the forehead sensor.

FIG. 12D illustrates a bottom view of the disposable portion of the forehead sensor that includes an attached adhesive layer.

FIGS. 13A-13D illustrate various embodiments and views of the disposable portion of the forehead sensor that include an EEG sensor.

FIG. 13A illustrates an exploded perspective view of the disposable portion of the forehead sensor with a detached adhesive layer.

FIG. 13B illustrates a top view of the disposable portion of the forehead sensor.

FIG. 13C illustrates a side view of the disposable portion of the forehead sensor.

FIG. 13D illustrates a bottom view of the disposable portion of the forehead sensor that includes an attached adhesive layer.

DETAILED DESCRIPTION

Figure 1A:
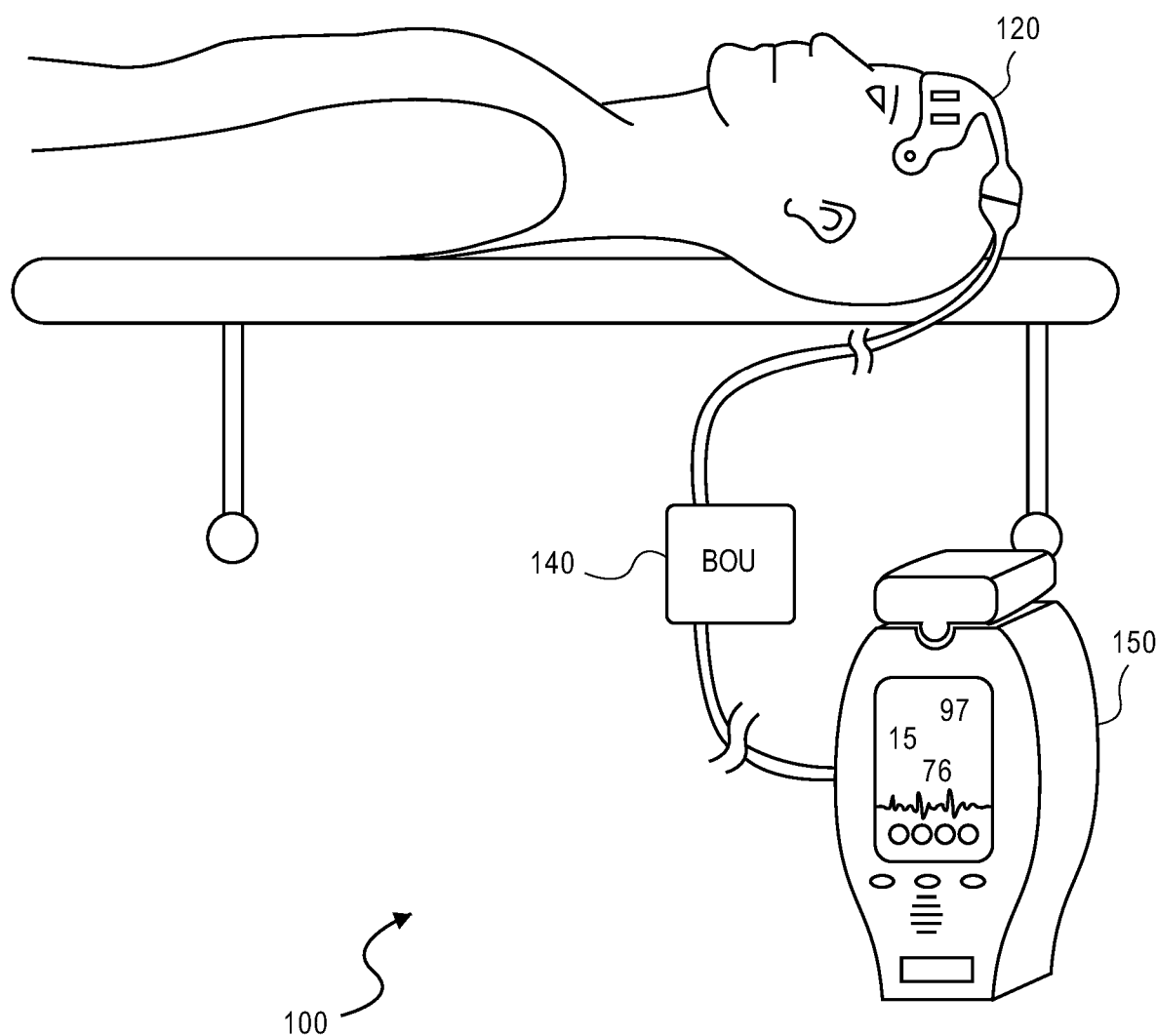
FIG. 1A illustrates an embodiment of a forehead sensor communicating with a brain oximetry unit, which in turn communicates with a pulse oximeter now configured to monitor a state of consciousness through brain oxygenation.

The present disclosure generally relates to patient monitoring devices. In order to provide a complete and accurate assessment of the state of a patient's various physiological systems, in an embodiment, a sensor may advantageously monitor one, multiple or combinations of EEG, cerebral oximetry, temperature, pulse oximetry, and other physiological parameters. In various embodiments, the sensor includes a disposable portion and reusable portion. For example, the disposable portion may advantageously include components near a measurement site surface (the patient's skin), including, for example, an EEG, a temperature sensor, tape, adhesive elements, positioning elements, or the like. On the other hand, the reusable portion may advantageously include more expensive or other components, circuitry or electronics, which, in some embodiments include for example time-of-use restrictions for quality control or the like. The reusable portion, can be used multiple times for a single patient, across different patients, or the like, often depending upon the effectiveness of sterilization procedures. The reusable components may include, for example, cerebral oximetry components, pulse oximetry components and other components to measure other various parameters.

In an embodiment, the disposable portion of the sensor may include an inductance connection or other electrical connection to the reusable portion of the sensor, and the signal from both sensors could thereby be transmitted through a common cable to a brain oximetry unit. In an embodiment, the brain oximetry unit may include an analog to digital converter, various electrical filters, and a microcontroller for processing and controlling the various sensor components.

In an embodiment, a brain oximetery unit or additional signal processing unit could communicate with the forehead sensor disclosed herein and one or more host display and patient monitoring stations. In an embodiment, the patient monitoring station may be a pulse oximeter. In an embodiment, the pulse oximeter may perform integrated display, data monitoring and processing of patient parameters including a connection for power and data communication. In an embodiment, some or all communication may be through wired, wireless, or other electrical connections. In an embodiment, the brain oximetry unit may advantageously be housed in a portable housing. In such embodiments, the unit may advantageously be physically associated with a monitored patient, such as, for example, attached in an arm band, a patient bed pouch, a hood or hat, a pocket of a shirt, gown, or other clothing, or the like. In other embodiments, the unit may be entirely or partially housed in a cable connector. In an embodiment, the signal processing and condition unit could also monitor patient parameters through other sensors including, for example, ECG, Sp02 from the earlobe, finger, forehead or other locations, blood pressure, respiration through acoustic or other monitoring technologies, or other clinically relevant physiological parameters.

In an embodiment, the pulse oximeter communicates with a sensor, such as a forehead sensor including one or more light sources configured to emit light at a patient's forehead. In an embodiment, the light source may include one or more emitters or emitter systems, such emitters or emitter systems may be embedded into a substrate. In various embodiments, the emitters could be either light emitting diodes ("LEDs"), lasers, superluminescent LEDs or some other light emitting components. These components could be arranged in any pattern on the substrate and could be either a single light emitting source or several light emitting sources. In an embodiment, the emitting components could emit light that deflects off of reflective surfaces associated with a cap of the substrate. The reflective cover could be any number of shapes or sizes and could be constructed to direct light to specific points or a point on the cap or substrate.

In an embodiment, a multi-faceted splitting mirror could reflect light to an opening in the substrate that would allow the light to escape and be emitted to an emission detector in an embodiment also housed in the light source substrate. The emission detector may advantageously sample the light providing feedback usable to create an optical bench or at least optical bench properties of the light source, including, for example, determinations of intensity, wavelength, or the like. In an embodiment, the light source may include a polarized filter for adjusting the emitter light, in some embodiments before exiting an opening in the emitter or being detected by the emission detector.

In an embodiment, a caregiver could analyze physiological information collected from the various sensors including a patient's temperature, EEG, brain oxygen saturation, stimulus response, electromyography or EMG, respiration monitor using acoustic sensor applied to the through, body oxygen saturation, glucose concentration, or other blood analytes, pulse, hydration, blood pressure, perfusion, or other parameters or combinations of parameters to determine relevant information about the state of a patient's well being. In another embodiment, a caregiver may advantageously analyze information collected from the various sensors to more completely assess the overall depth of a patient's sedation and obtain an assessment superior to an assessment derived from monitoring a single or a few of the parameters mentioned above.

Reference will now be made to the Figures to discuss embodiments of the present disclosure.

Figure 1B:
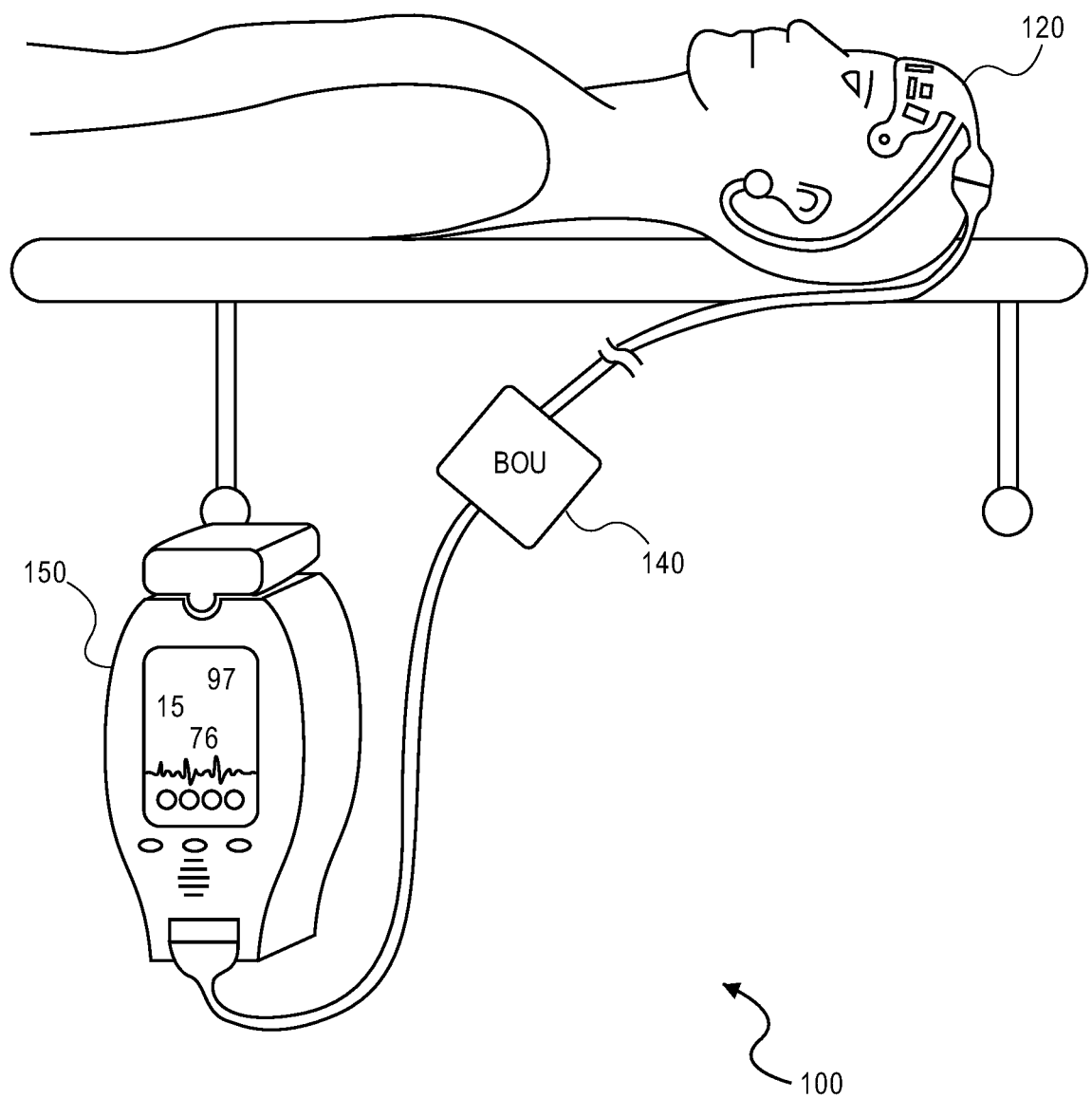
FIG. 1B illustrates an embodiment of the forehead sensor of FIG. 1A including an ear pulse oximetry sensor.

FIGS. 1A and 1B illustrate examples of a patient monitoring system 100. In certain embodiments, the patient monitoring system 100 measures several physiological parameters including cerebral electrical activity, temperature, cerebral oxygenation, including venous and arterial oxygenation, arterial oxygenation at various other points on the body, various other blood analytes including total hemoglobin, glucose, lipids, stimulus response, electromyography or EMG, respiration, pulse, hydration, blood pressure, perfusion, or other parameters or combination of other physiologically relevant patient characteristics. The information from these physiological parameters can be evaluated using trend analysis, absolute and relative measures of certain parameters, combined or alone to evaluate the total wellness and current state of a patient at any point in time.

The patient monitoring system can include multiple or a single sensor 120, a brain oximetry unit 140, and a pulse oximeter 150. The sensor 120 can be any variety of shapes and sizes, and could be applied to a variety of measurement sites on a patient's skin including any location on the forehead and temples or other location of the head. Also, electrodes designed to be placed at a measurement site covered with a patient's hair may advantageously be implemented in order to apply the sensor to any part of a patient's head that is covered with hair. A caregiver or patient may fasten the sensor to the patient's head with a variety of mechanism including adhesive, straps, caps, combinations of the same, or other devices for fastening sensors to a patient's body or skin known in the art.

In an embodiment, the patient monitoring system 100 advantageously utilizes wireless communication to provide a portable unit to accommodate an ambulatory patient, or other patient in transit. For example, in one embodiment, the brain oximetry unit 140 may be attached to an arm band or included in an arm band or other device that is wearable by the patient, including in a cap, a hood, a sling or a pocket of a garment. In an embodiment, the sensor would communicate with the arm band brain oximetry unit 140 with a hard wired connection or a wireless connection for convenience and flexibility of the patient obtained by eliminating excess wires.

In an embodiment, the portable brain oximetry unit 140, such as an armband brain oximetry unit 140, could also communicate wirelessly with the pulse oximeter 150. This would allow the brain oximetry unit 140 to be transported between various caregiving facilities, each with their own stationary pulse oximeters 150 without unhooking and reinserting hardwired electrical connections. Instead, a brain oximetry unit 140 could establish a wireless communication link with a stationary pulse oximeter 150 as the brain oximetry unit 140 is brought into proximity of the pulse oximeter 150. In an embodiment, the devices could establish the connection automatically and patient data may be automatically sent from the brain oximetry unit 140 to the pulse oximeter 150 or the connection may require input from a caregiver in the user interface of either of the devices. This will advantageously facilitate portability and seamless monitoring of a patient while being transported, for example, from an ambulance to a hospital room or from room to room in a hospital.

In an embodiment, the pulse oximeter 150 may be a multi-parameter patient monitoring station or other host device capable of monitoring a wide variety of vital signs and blood constituents and other parameters or combinations of parameters such as those monitors commercially available from Masimo Corporation of Irvine, Calif., and disclosed herein with reference to U.S. Pat. Nos. 6,584,336, 6,661,161, 6,850,788, and 7,415,297, among others assigned to Masimo Corporation, and U.S. Patent Publication No. 2006/0211924, 2010/0030040, among others assigned to Masimo Corporation or Masimo Laboratories, Inc. of Irvine Calif.

FIG. 1B illustrates an embodiment of the patient monitoring system 100 with a pulse oximeter 150 attached to a sensor 120 or through some physical electrical conduction connection, wireless, or other suitable electrical connection to the pulse oximeter 150. This will advantageously provide additional information about the state of the arterial oxygenation of the blood being transported to the head. In an embodiment, the pulse oximeter 150 branches off the wiring from the sensor 120.

In an embodiment, a caregiver or the patient may attach the brain oximetry unit 140 directly to the patient's arm or other part or clothing of the patient through an armband with straps or some other means known in the art to connect a portable monitoring unit to a patient. In an embodiment, a brain oximetry unit 140 may be integrated into a hat or other headgear wearable by the patient or some other structure near the patient. In an embodiment, brain oximetry unit 140 can rest on a table or other surface near the patient.

In some embodiments, a brain oximetry unit 140 can be integrated with the pulse oximeter 150. Alternatively, the brain oximetry unit 140 could be a module that is docked or somehow associated with a multi-parameter patient monitoring station.

Figure 2B:
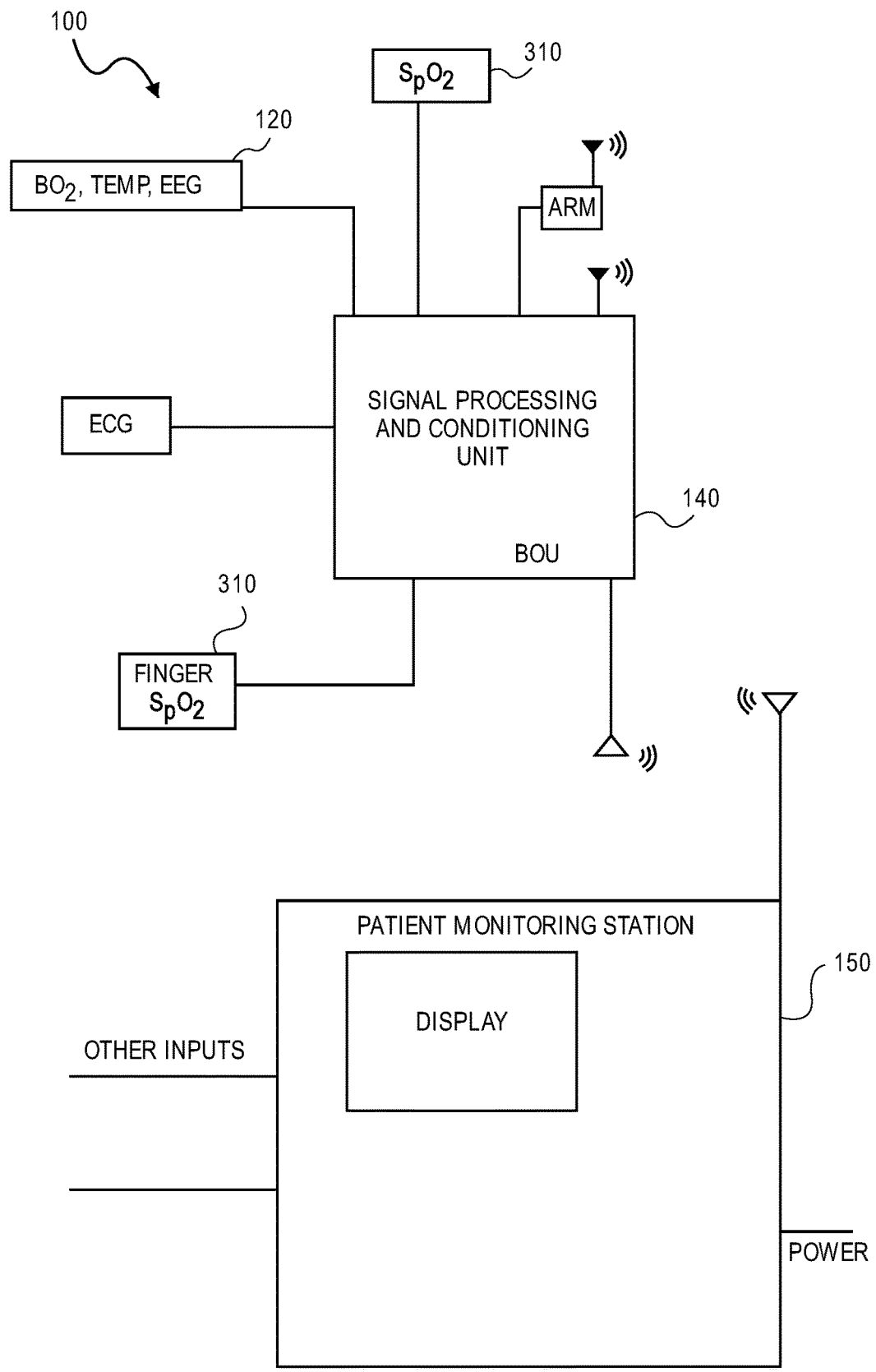

FIGS. 2A and 2B show block diagrams of various embodiments of the brain oximetry unit 140, sensors 120, and pulse oximeter 150. In an embodiment, the brain oximetry unit 140 may utilize a processor 220 which may be a micro-controller or other processor, which may control or coordinate some or all of the functions of the various emitters 230 and detectors 260 and other sensors 120 and in an embodiment, may coordinate, process or condition, or manipulate the electronic data in some other manner, before communicating the data to the pulse oximeter 150. Also, the processor 220 may receive instructions or data control messages from the pulse oximeter 150 to provide the appropriate conditioning and controlling of the various front end components of the various sensors 120 associated the pulse oximeter 150. In an embodiment, data transmitted between the brain oximetry unit 140, the pulse oximeter 150, the sensors 120 and any other associated components of a patient monitoring system 100 may be communicated by the devices using electrical wires, wireless communication, optical communication, RFID, LAN networks, or other electronic devices for communicating data known in the art.

The brain oximetry unit 140 may also include various front end components for the various sensors 120 that may be associated with the brain oximetry unit 140. In an embodiment, front end components may translate and transmit instructions and control signals for driving the various sensors. In an embodiment, the front end components may translate, process, or transmit instructions and control signals to the emitting or light producing components of the sensor. The front end components may also receive and transmit data acquired by the detectors of the sensors to the microcontroller 220 or other processor 220.

These front end components could include front end components for a variety of sensors 120 including for sensors that detect blood oxygenation, EEG, ECG, temperature, acoustic respiration monitoring ("ARM") sensors, such as those available from Masimo Corporation of Irvine, Calif., acoustic throat respiratory sensor, and brain oxygenation. In an embodiment, a caregiver could advantageously utilize a device with the ability to monitor the plurality of above mentioned parameters to more accurately determine a depth of a patient's sedation. In an embodiment, a front end component that would be associated with a sensor 120 that detects brain oxygenation may have a sub component dedicated to driving emitters 230 associated with a light source of the brain oxygenation sensor and a sub-component associated with the detector 230 or detectors 230 of the brain oxygenation sensor 300 for receiving and transmitting the detected signals that pass through various body tissues.

In an embodiment, one of the various sensors associated with the front end components of the brain oximetry unit could be, for example, a blood oxygenation sensor 310 which may be placed at various measurement sites on a patient's skin, including the earlobe, finger, forehead or other places known in the art suitable for detecting blood oxygenation. Many suitable pulse oximeter sensors 310 are known in the art such as those blood oxygenation sensors 310 commercially available from Masimo Corporation of Irvine, Calif., and disclosed herein with reference to U.S. Pat. Nos. 5,638,818, 6,285,896, 6,377,829, 6,580,086, 6,985,764, 7,341,559, or others.

In an embodiment, another sensor 120 that may be associated with a front end component of the brain oximetry unit 140 could be a temperature sensor 320. The temperature sensor 320 could detect the temperature of the skin, the temperature inside the ear, the temperature under the tongue, or any other temperature measurement method known in the art. In an embodiment, the temperature sensor 320 could be any suitable thermistor, or any other temperature sensor 320 known in the art capable of detecting a surface temperature of a patient's skin. Additional temperature sensor may advantageously provide feedback to the unit 140 regarding the performance or temperature of one, combinations of, or all of the emitters 230.

An EEG sensor 330 may also be associated with the front end components of the cerebral oximeter 140. In an embodiment, the EEG sensor 330 may be any of a variety of EEG sensors 330 known in the art. An EEG sensor 330 could be applied to a patient at any of a multitude of locations and measurement sites on the skin of the head of a patient. In an embodiment, the EEG sensor 330 may include electrode leads that may be placed on a measurement site in contact with the skin of the patient. In an embodiment, the EEG 330 may monitor the electrical activity of a patient's brain through any number of electrodes, electrode leads, and channels or other systems known in the art.

In an embodiment, the EEG sensor 330 may monitor and collect data from a patient's brain using 4 channels and 6 electrodes. In another embodiment, the EEG 330 may use 3 channels and 5 electrodes. In another embodiment, any variety or combination of sensors maybe be used that are suitable for obtaining an EEG signal, for example, such a system is disclosed in U.S. Ser. No. 60/164,444, 6,654,626, 6,128,521, or the like.

A brain oxygenation sensor 300 may also be associated with the front end components of the brain oximetry unit 140. In an embodiment, the brain oxygenation sensor 300 includes a light source 230, and a detector 260. The light source 230 of the brain oxygenation sensor 300 includes emitter(s) that would emit light, sonic or other radiation into the forehead at one, two or other plurality of measurement sites located on the skin of the patient at a plurality of predetermined wavelengths. In an embodiment, the brain oxygenation sensor 300 would include a detector 260 with photodiodes or other radiation detection devices to detect the radiation emitting from the patient at a one or two or a plurality of measurement sites on the skin of the head of a patient. Many suitable brain oxygenation sensors 300 and cerebral oximeters are known in the art including those disclosed in U.S. Pat. Nos. 7,072,701, 7,047,054, or similar sensors.

In an embodiment, the light source 230 of the brain oxygenation sensor 300 may include an emission detector 260. In an embodiment, the emission detector 260 would detect the light emitted from the light source 230 before passing through or contacting the measurement site of the patient. In an embodiment, an output from the emission detector 230 would be communicated to the micro-controller 220 in the brain oximetry unit 140, the processing unit in the cerebral oximeter 140 or, some other processing component associated with the patient monitoring system 100 in order to calculate an approximate output intensity of the light emitted by the emitter(s) 230. The micro-controller 220 or other processor 220 could calculate the output intensity based on the output of the emission detector 260 by comparing the data to calibration data. In an embodiment, the calibration data could include measurement of intensity of light emitted from the emitter(s) 230 and corresponding measurements of output from the emission detector 260. This data could then be correlated to real time output from the emission detector 260 while the oxygenation sensor 230 is in use to determine an actual or approximate intensity of light or radiation being emitted by the emitter(s) 230 utilizing a calibration curve or other suitable calculation or processing method. In an embodiment, the calibration data may be stored in an EPROM or other memory module in the brain oximetry unit 140, the pulse oximeter 150, or other patient processing module associated with the patient monitoring system 100.

In an embodiment, the detector 260 will detect light or other radiation emitted from the light source 230 after, in an embodiment, some of the light has entered the measurement site on the patient and has been attenuated by a patient's tissue. In an embodiment, the detector 260 could be any number of detectors known in the art for detecting light or other radiation including photodiodes or other types of light or radiation detectors. In one embodiment, the detector 260 may convert detected light or other radiation into a signal, for example, an electrical output signal, which may represent the intensity or other attributes of the radiation. In an embodiment, the signal from the detector 260 may be sent to a brain oxygenation detector 260 front end located in the brain oximetry unit 140 for processing, conditioning or transmitting to the pulse oximeter 150 or other patient monitoring processor. In one embodiment, the signal may be converted into a digital format by an analog to digital converted located in either the brain oximetry unit 140 or the pulse oximeter 150. In an embodiment, the data from the detector 260 of the brain oxygenation sensor 300 may be processed to determine the cerebral oxygenation of a patient's brain tissue. In an embodiment, the processing of the data may include determining the changes of intensity between various wavelengths of emitted and detected light of the cerebral oxygenation sensor 300.

In an embodiment, the cerebral oximeter 150 or multi-parameter patient monitor acquires data from the brain oximetry unit 140 or sensor 120 derived from physiologically relevant parameters. In an embodiment, the pulse oximeter 150 could give visual quantitative or qualitative assessments of the patient's well being based on one or more of the various parameters or physiological attributes measured.

In an embodiment, a caregiver may utilize various physiological parameters to make a quantitative assessment of the patient's depth of sedation as indicated by an index based on for example, a patient's temperature, electroencephalogram or EEG, brain oxygen saturation, stimulus response, electromyography or EMG, respiration based on acoustic through sensors, body oxygen saturation or other blood analytes, pulse, hydration, blood pressure, perfusion, or other parameters or combinations of parameters. In another embodiment, various aspects of sedation could be assessed quantitatively or qualitatively based on a visual representation of the patient's sedation in the aspects including hypnosis, responsiveness, muscle relaxation or other clinically relevant facets of depth of anesthesia.

In an embodiment, the pulse oximeter 150 may supply power to brain oximetry unit 140 over a single line and data would be transferred back and forth between the brain oximetry unit 140 and pulse oximeter 150 over a separate line or lines. In another embodiment, both power and data could be transmitted over the same line or the same wire with multiple lines in the wire. In another embodiment, data and power could be transmitted wirelessly or through an inductance connection between the patient monitoring station and the signal processing unit or any other suitable connections or transmission techniques known in the art. Induction or magnetic connections are also disclosed in U.S. patent application Ser. No. 13/246,768, titled "Magnetic Electrical Connector for Patient Monitors," filed herewith on Sep. 27, 2011.

In an embodiment, the functionality of the brain oximetry unit 140 could be optionally controlled by the pulse oximeter 150. In an embodiment, the data and qualitative and quantitative assessments of a patient's wellness being could be displayed on either or both the brain oximetry unit 140 and pulse oximeter 150. Also, audible alarms and other indicators could be displayed on either or both the brain oximetry unit 140 and pulse oximeter 150 in response to various threshold breaches based on the assessment of the patient's wellness determined from the various monitored parameters.

Figure 3A:
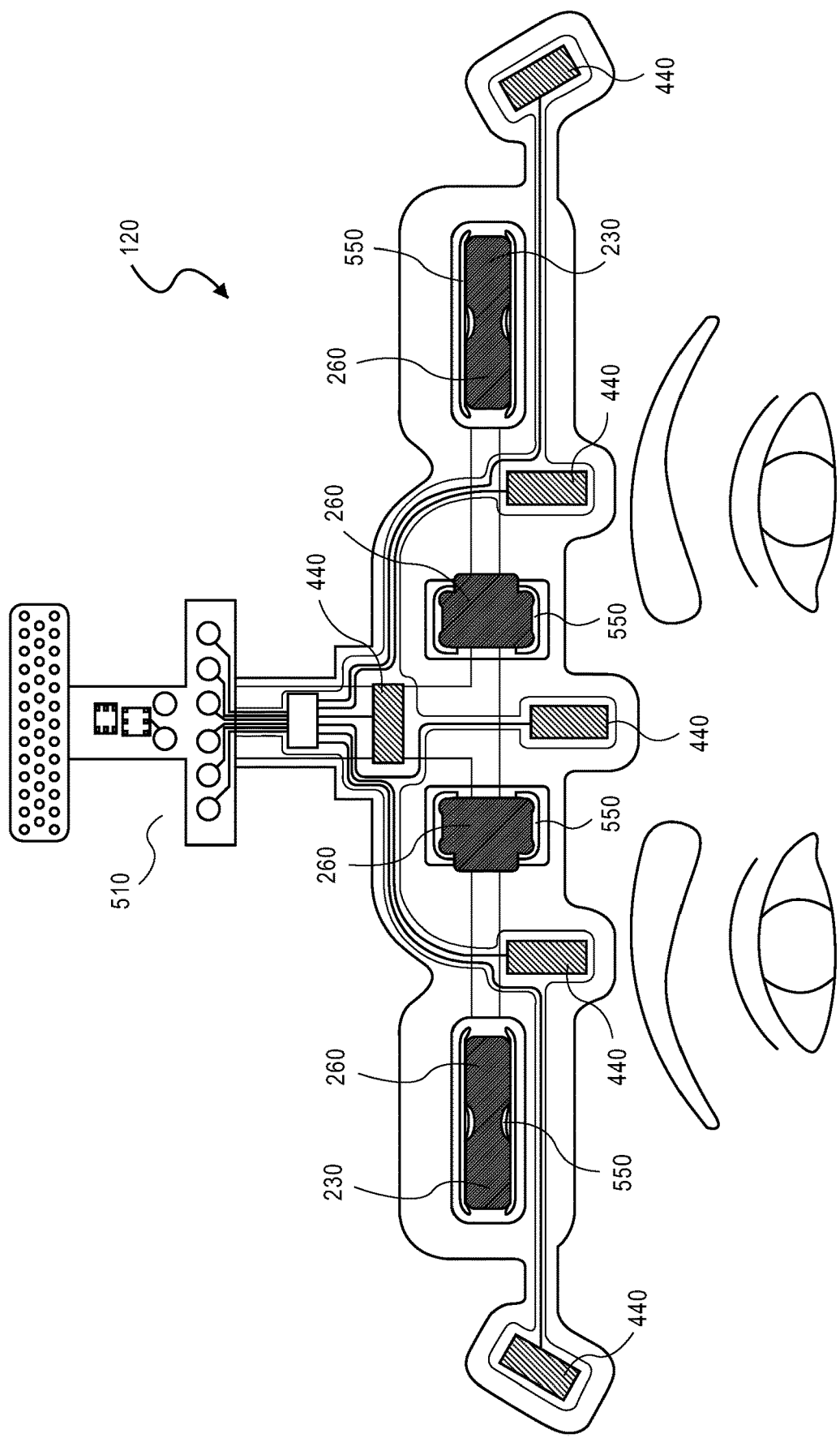
FIGS. 3A-3O illustrate various embodiments of the forehead sensor of FIG. 1A.

FIGS. 3A-3F illustrate several embodiments of the sensor 120. FIG. 3A shows an embodiment of the sensor 120 wherein disposable 410 and reusable portions 420 of the sensor 120 are connected and overlayed on top of one another. FIG. 3A shows six EEG electrodes 440 with two reference electrodes and four active channel electrodes. FIG. 3A also shows the light source 230 and detector 260 components of the brain oxygenation sensor 300. Any number of suitable light sources 230 and detectors 260 may be incorporated into the forehead sensor 120. All or some of the above mentioned sensor components including the EEG leads 440 and the brain oxygenation emitter 230 and detector 260 components may be linked to a single chip for transmission of acquired signals and drive signals or each component may be linked to its own individual chip through wires, or printed circuits, or other suitable electrical connections.

In one embodiment, the light source 230 may include one or more emitters. In one embodiment, the emitter could be a laser, or any suitable apparatus for emitting near-infrared or other spectrum of light including LEDS, super luminescent LEDs, or some other light emitting components. In one embodiment, the light source 230 may be incorporated with the brain oximetry unit 140 and the light or other radiation could be emitted from the light source 230 onto a fiber optic cable which would transmit the light from the light source 230 to the measurement site. In another embodiment, the emitter(s), including, for example, a laser or LED emitter(s), is embedded in the emitter 230 directly in the forehead sensor. Other fiber optics may be used after emission of the light from the light source to equalize the intensity and distribution of the radiation over a cross sectional area of a beam of emitted light after it exits the emitter and before it enters the measurement site of the patient.

The detector 260 of the brain oxygenation sensor 300 may be any suitable device for detecting radiation including any combination of various photodiodes including InGas and Si photodiodes. In an embodiment, the detector 260 is a photodiode connected directly to the forehead sensor 120. In another embodiment, the forehead sensor 120 collects light that has passed through patient tissue with a fiber optic cable or other similar apparatus that is positioned at an appropriate measurement site, for example on the patient's forehead. In an embodiment, the fiber optic cable could then transmit the collected light to the detector 260 of the brain oxygenation sensor 300.

The EEG electrodes 440 may be any suitable electrodes for detecting the electro-potentials on the surface of the skin of a patient's head. In one embodiment, EEG electrodes 440 comprise a metal or other suitable conductor and utilize leads contacting the surface of the skin. In another embodiment, the electrodes 440 are gelled electrodes that make contact through the skin via gel and have metal leads that come into contact with the gel. In still yet another embodiment, the EEG electrodes 440 may be glued to the forehead with any suitable patient dermal adhesive for connecting the EEG electrodes 440 and may have electrical conductivity. In an embodiment, potentials from the EEG electrodes 440 are transmitted to the brain oximetry unit 140 for further conditioning, transmitting or processing.

Figure 3B:
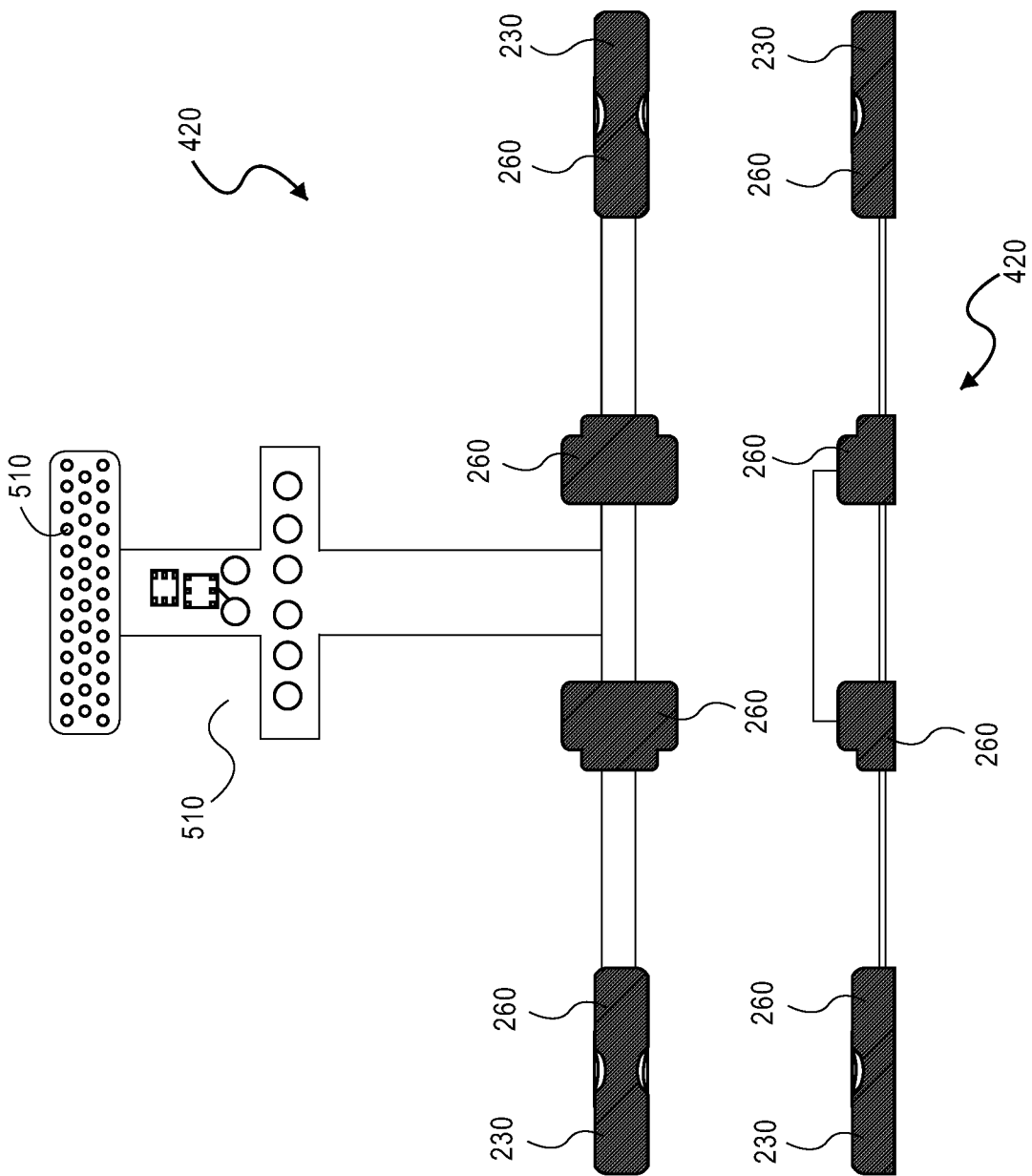
FIGS. 3B-3C illustrate embodiments of the reusable portion including various cerebral oximetry sensor components.
Figure 3C:
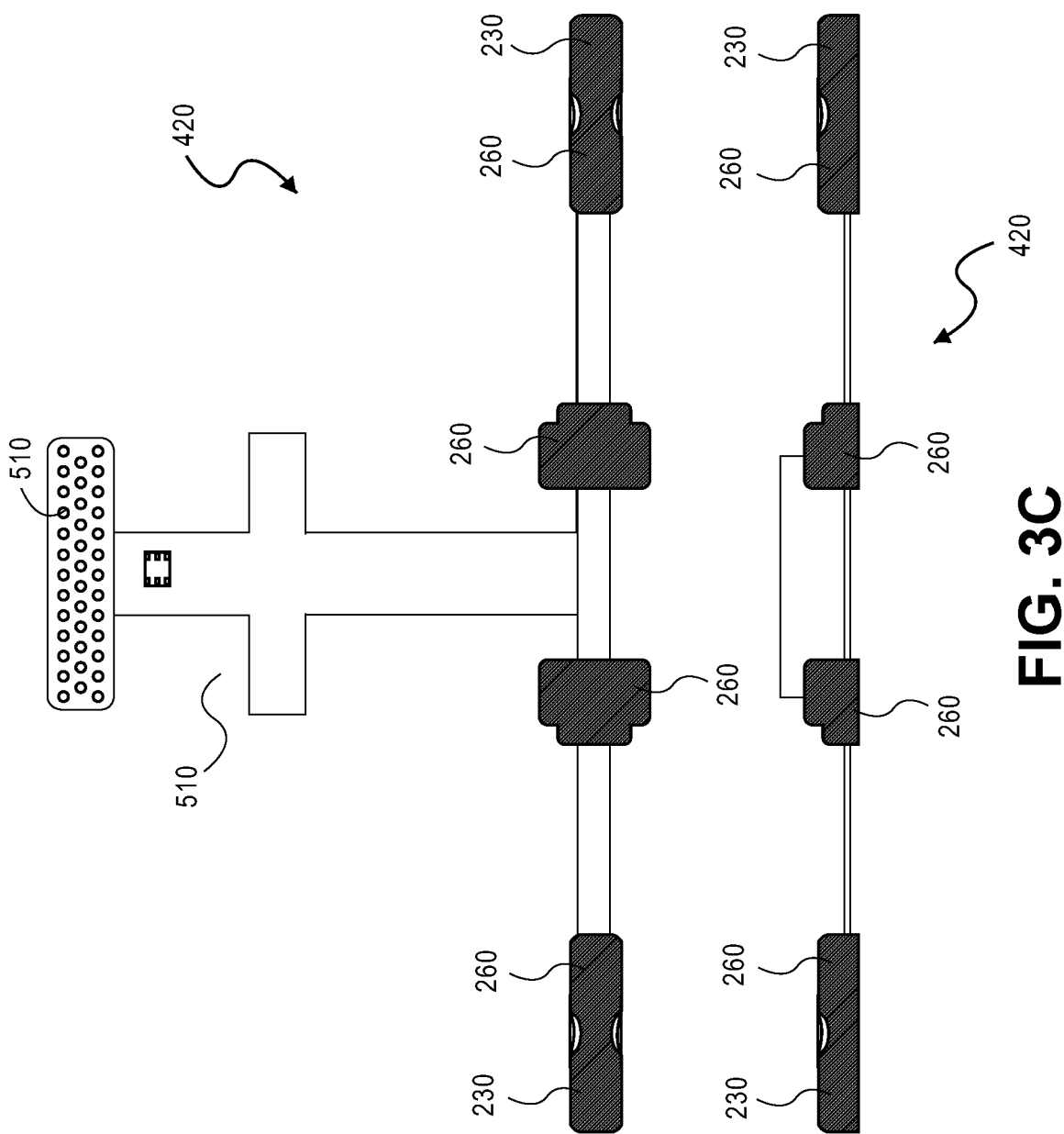

FIGS. 3B and 3C show embodiments of a reusable portion 420 of the sensor 120. In an embodiment, the reusable portion 420 includes the potentially more expensive components, including, for example, the sensor light source(s) 230 and detector(s) 260. The reusable portion 420 may also include the temperature sensor 320. The temperature sensor 320 may be any suitable sensor that can detect the temperature of the surface of the skin or other patient temperatures. In an embodiment, the temperature sensor 320 may include a thermistor associated with the reusable portion 420 of the sensor 120.

In an embodiment, the reusable portion 420 includes an interface 510 that couples the reusable portion 420 of the sensor to the brain oximetry unit 140. The interface 510 may be any suitable electrical or data connection or communication port or device including, for example, a pin connector and receiver. Various other communication or electrical connections known in the art may be utilized. In an embodiment, the interface 510 is an inductance connection utilizing transformers to couple a data and electrical connection across an insulator. In another embodiment, the interface 510 provides a data or electronic coupling between the reusable portion 420 and the disposable portion 410 of the sensor.

Figure 3D:
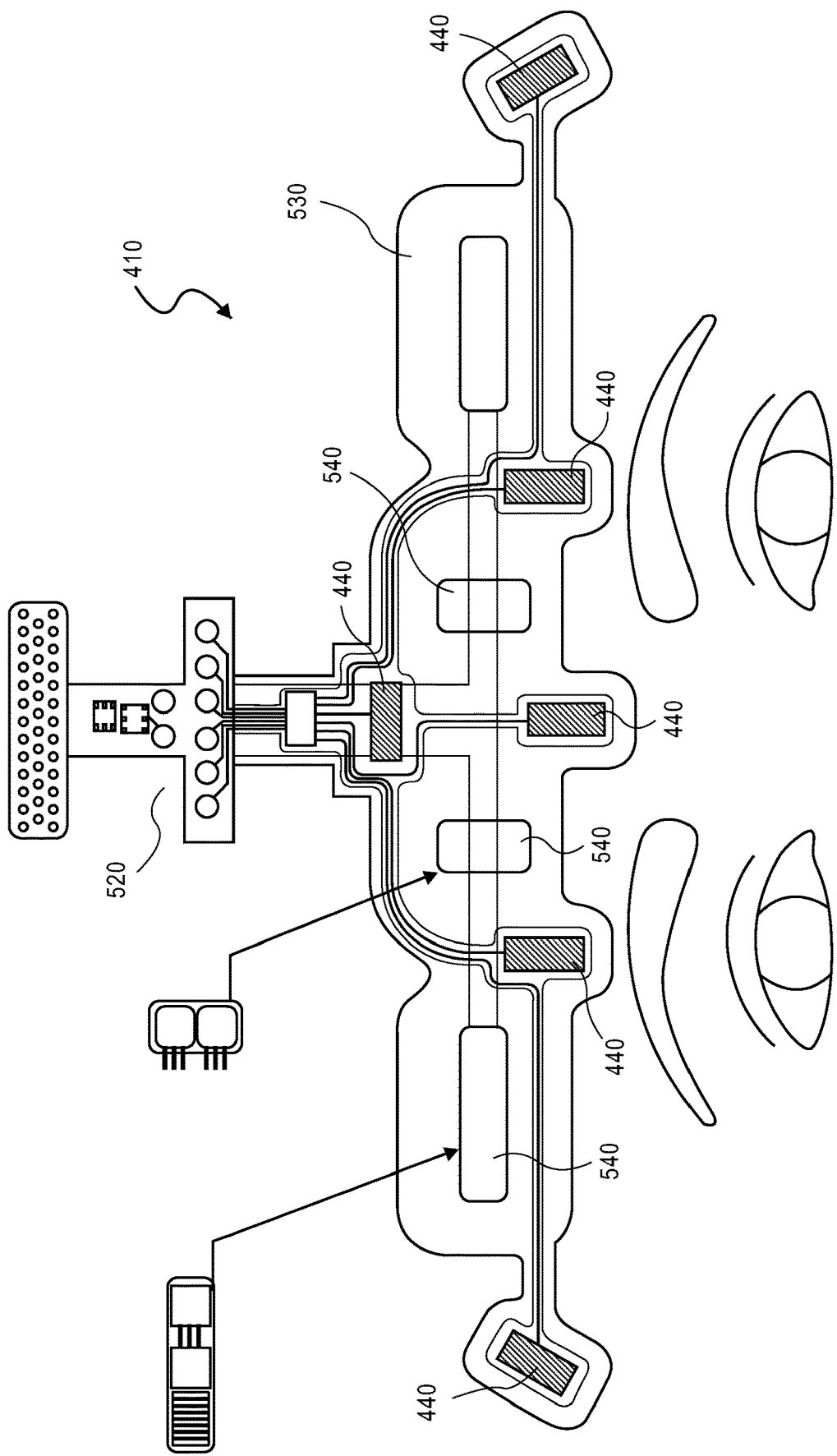
Figure 3E:
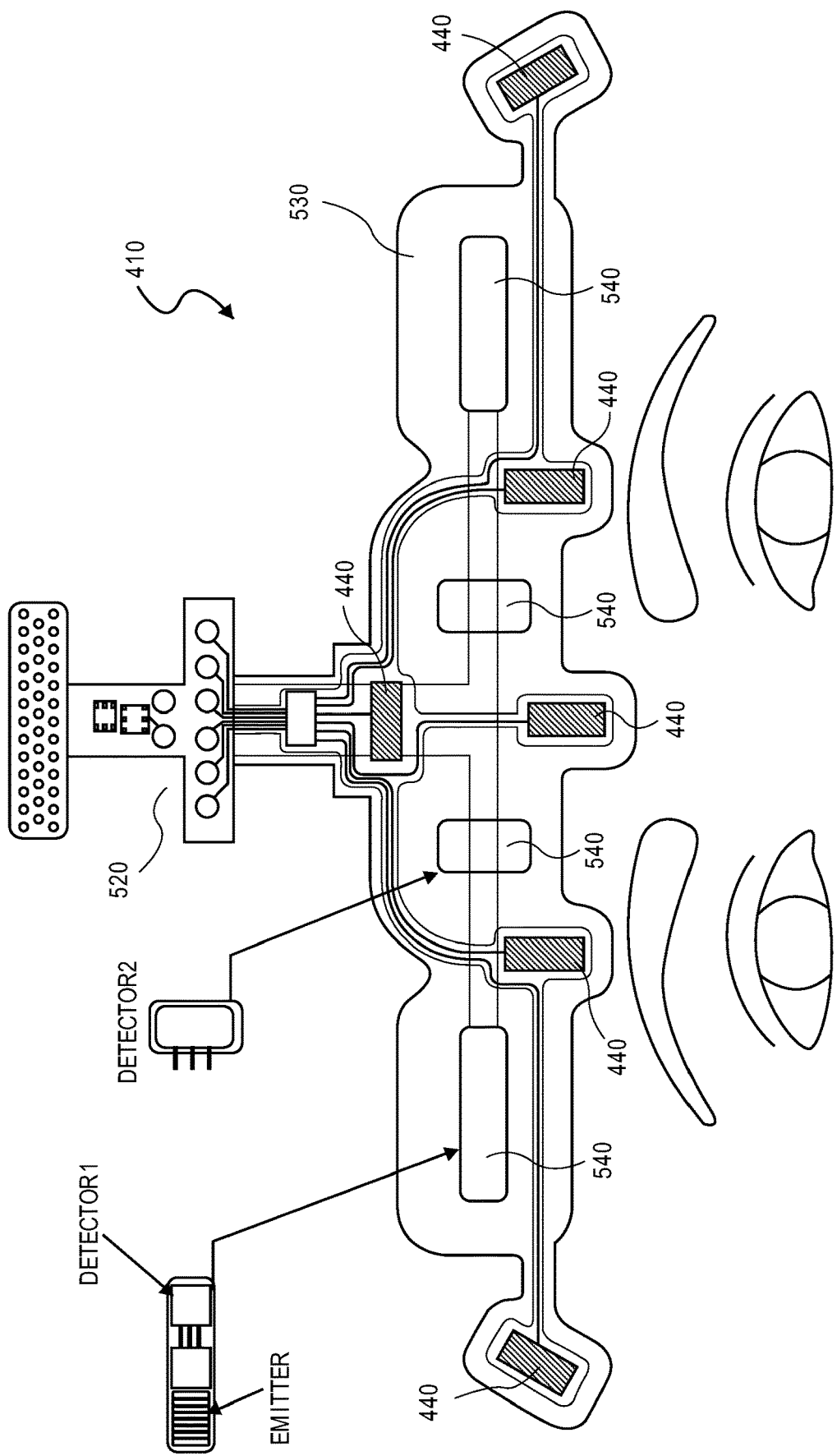
Figure 3F:
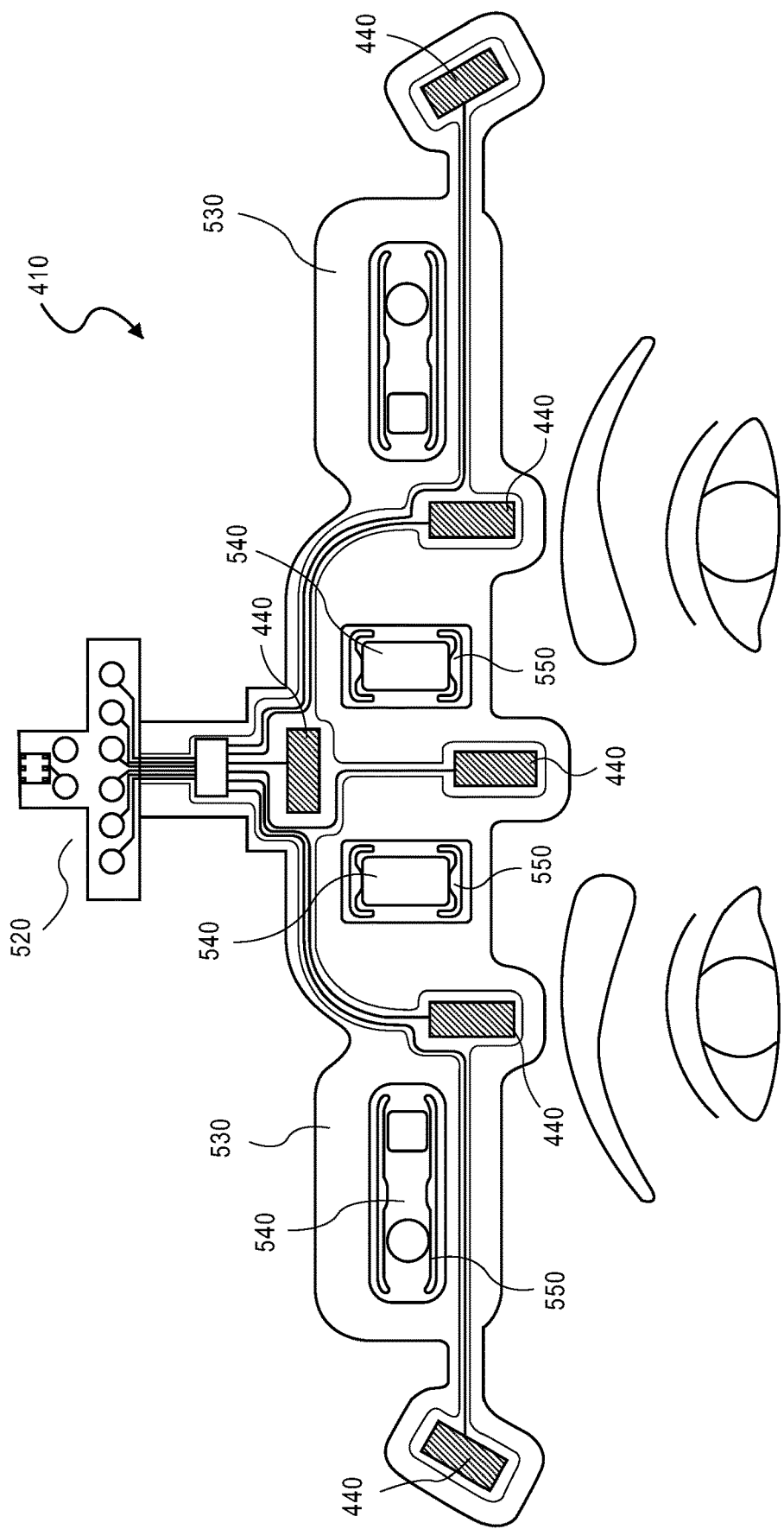

FIGS. 3D-3O illustrate various embodiments of a disposable portion 410 of a forehead sensor 120 that, in an embodiment, attaches to a measurement site of a patient's head and provides a base 520 to which the reusable portion 420 may be docked, mated or connected. FIGS. 3D-3E illustrate an embodiment of a single chip disposable portion 410 of the sensor 120. The disposable portion 410 houses the components of the sensor 120 that may be less expensive than at least some of the components contained in the reusable portion 420 of the sensor 120 and therefore may be disposed after a single or multiple uses, either on the same patient or different patients. The disposable portion 410 of the sensor 120 includes a tape substrate 530 that provides a base or substrate to which at least some of the components of the disposable portion 410 may adhere or be integrated. In an embodiment, the tape 530 can be constructed from any suitable disposable material that will effectively hold the components includes in the disposable portion 410 to a patient's forehead or other measurement site. In an embodiment, the tape 530 includes a suitable dermal adhesive on a patient side of the disposable portion 410 for temporary adhesion of the sensor 120 to a patient's skin.

In an embodiment, the disposable portion 410 of the sensor 120 may incorporate various disposable components which may include, EEG electrodes 440. In one embodiment, the EEG electrodes 440 may be fastened to the tape 530 of the disposable portion 410. In an embodiment, the EEG electrodes 440 could be embedded in the tape 530 by any known adhesive in the sensor arts or any other suitable means for connecting the EEG electrodes 440 that would allow the EEG electrode 440 leads to be exposed on a patient side of tape 530 in an appropriate position to come in close proximity to a measurement site of a patient's skin. In an embodiment, EEG electrodes 440 may be gelled so that the gel contacts the electrodes and a measurement site of a patient's skin to provide an electrical path between the measurement site of the patient's skin and the EEG electrodes 440. In an embodiment, the leads of the EEG electrodes 440 are connected to a single chip by wires or other suitable electrical connections, such a as a printed circuit.

Figure 3G:
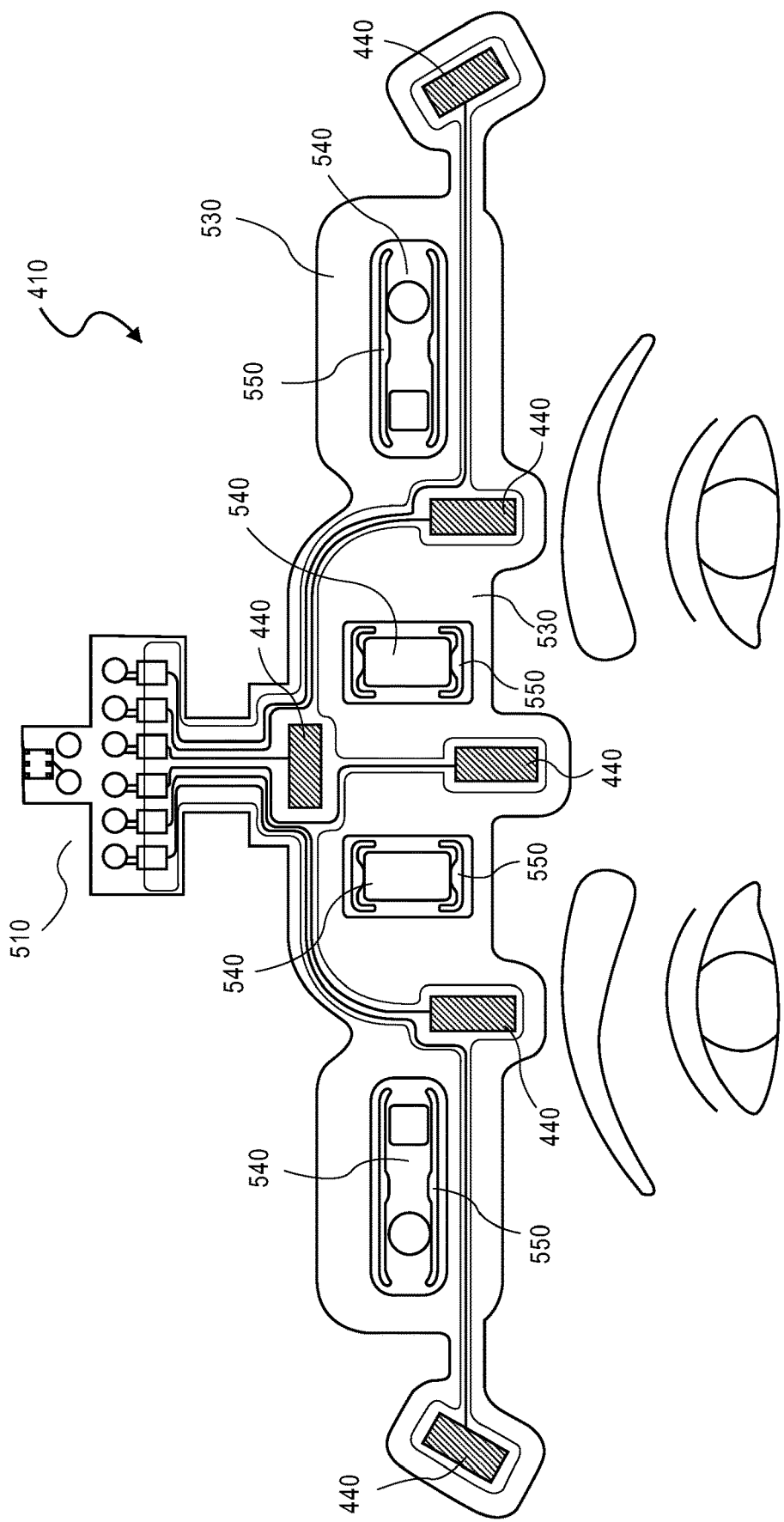
Figure 3H:
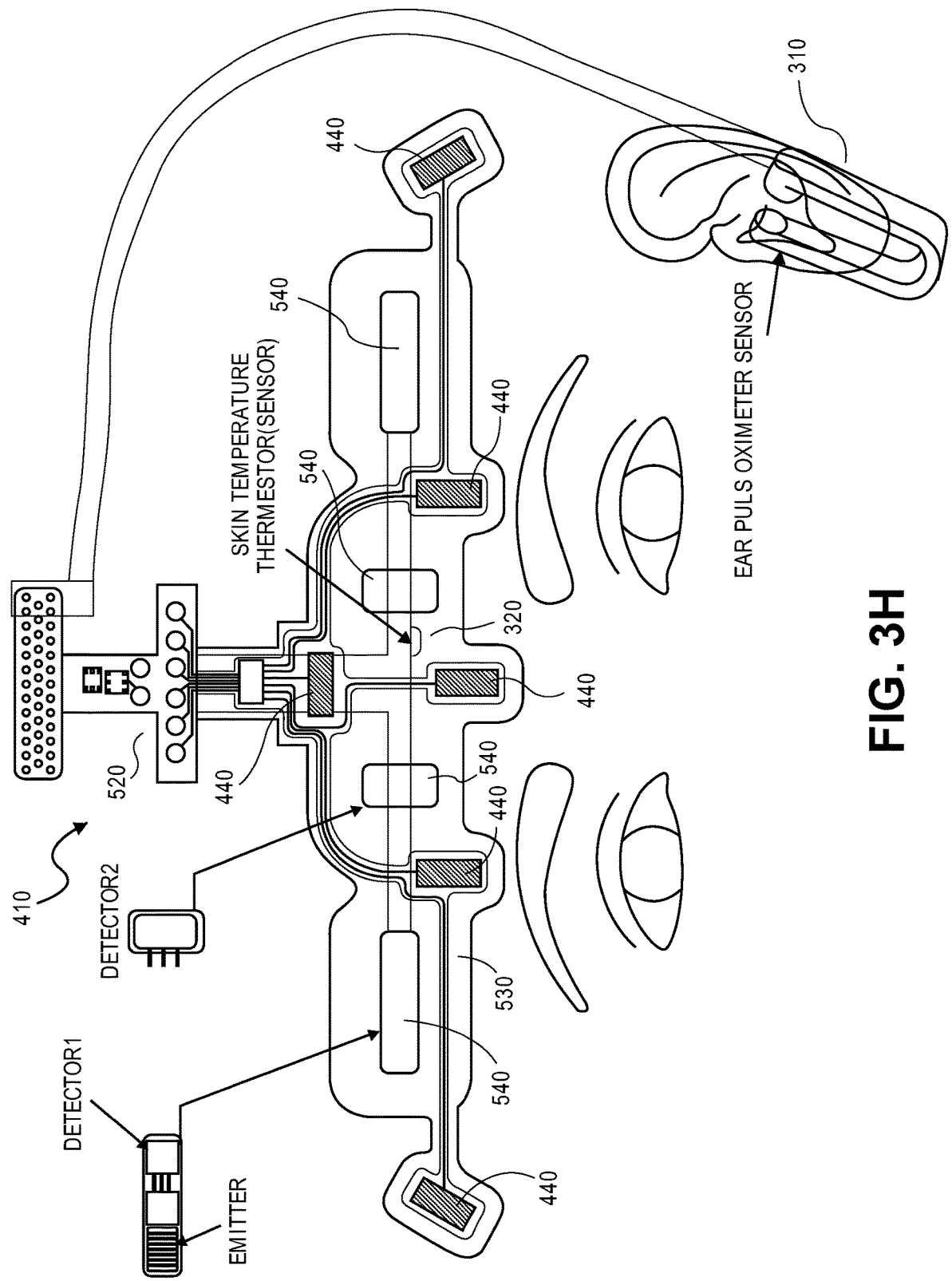
Figure 3I:
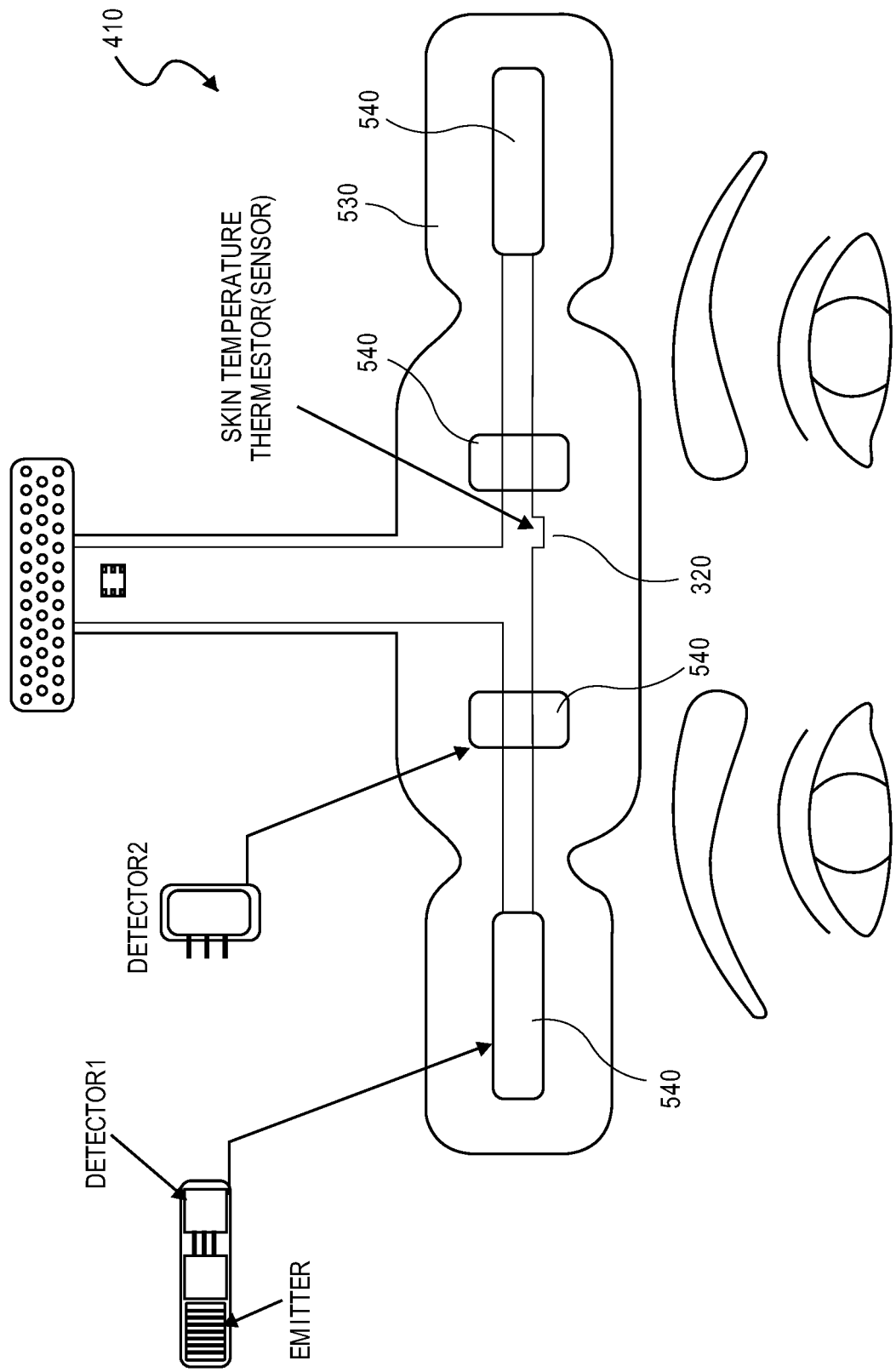
Figure 3K:
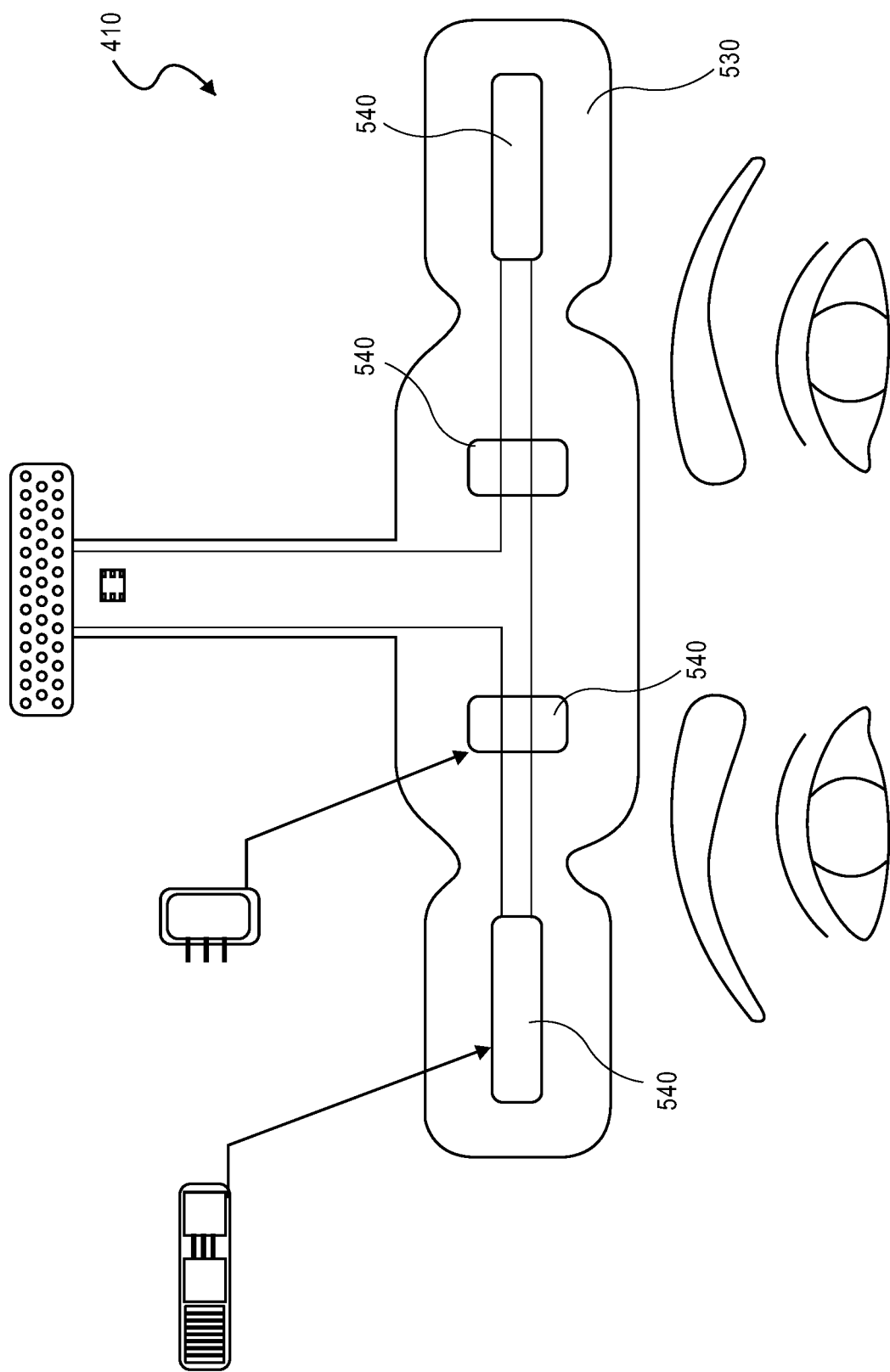
Figure 3L:
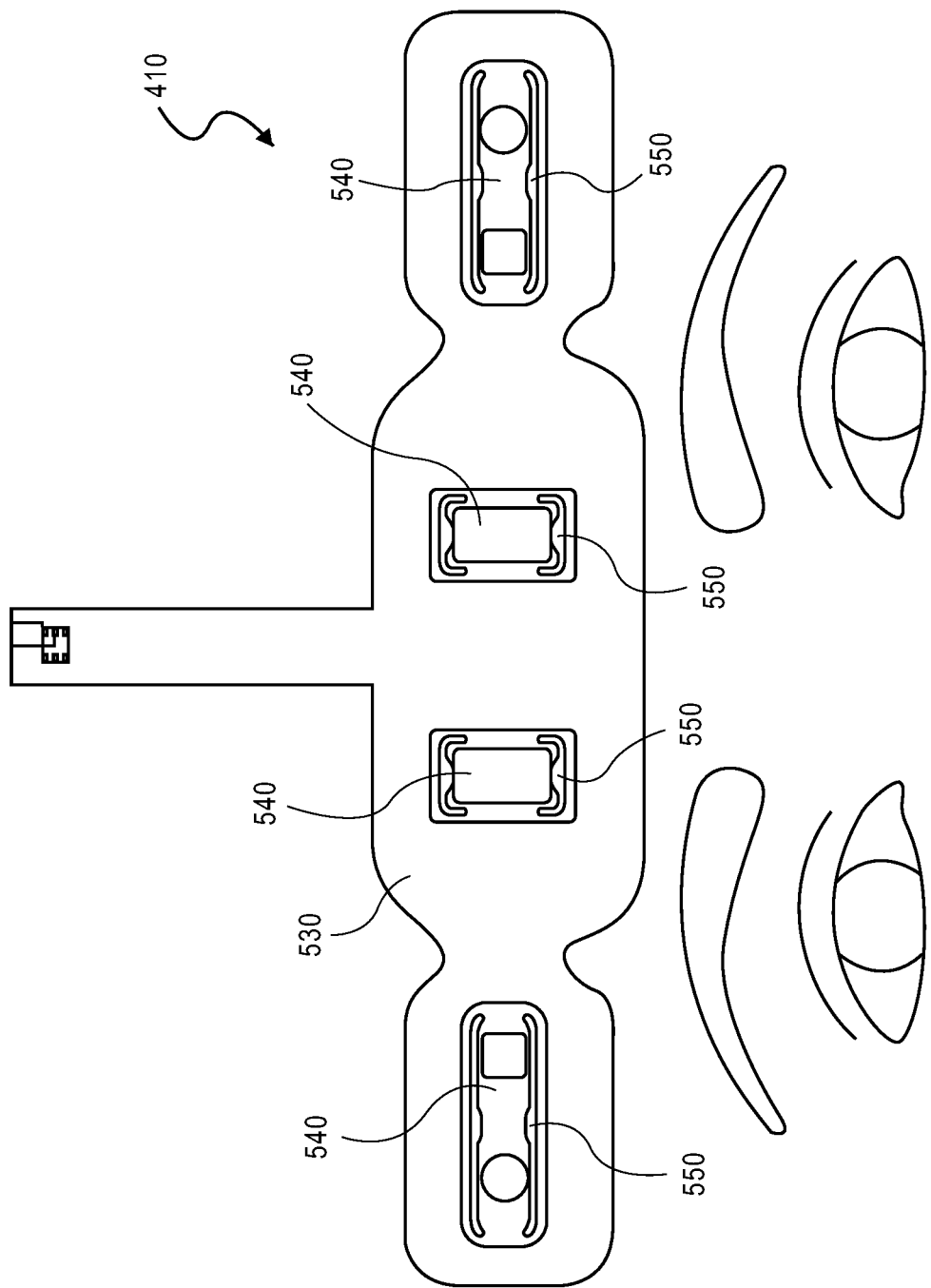
Figure 3M:
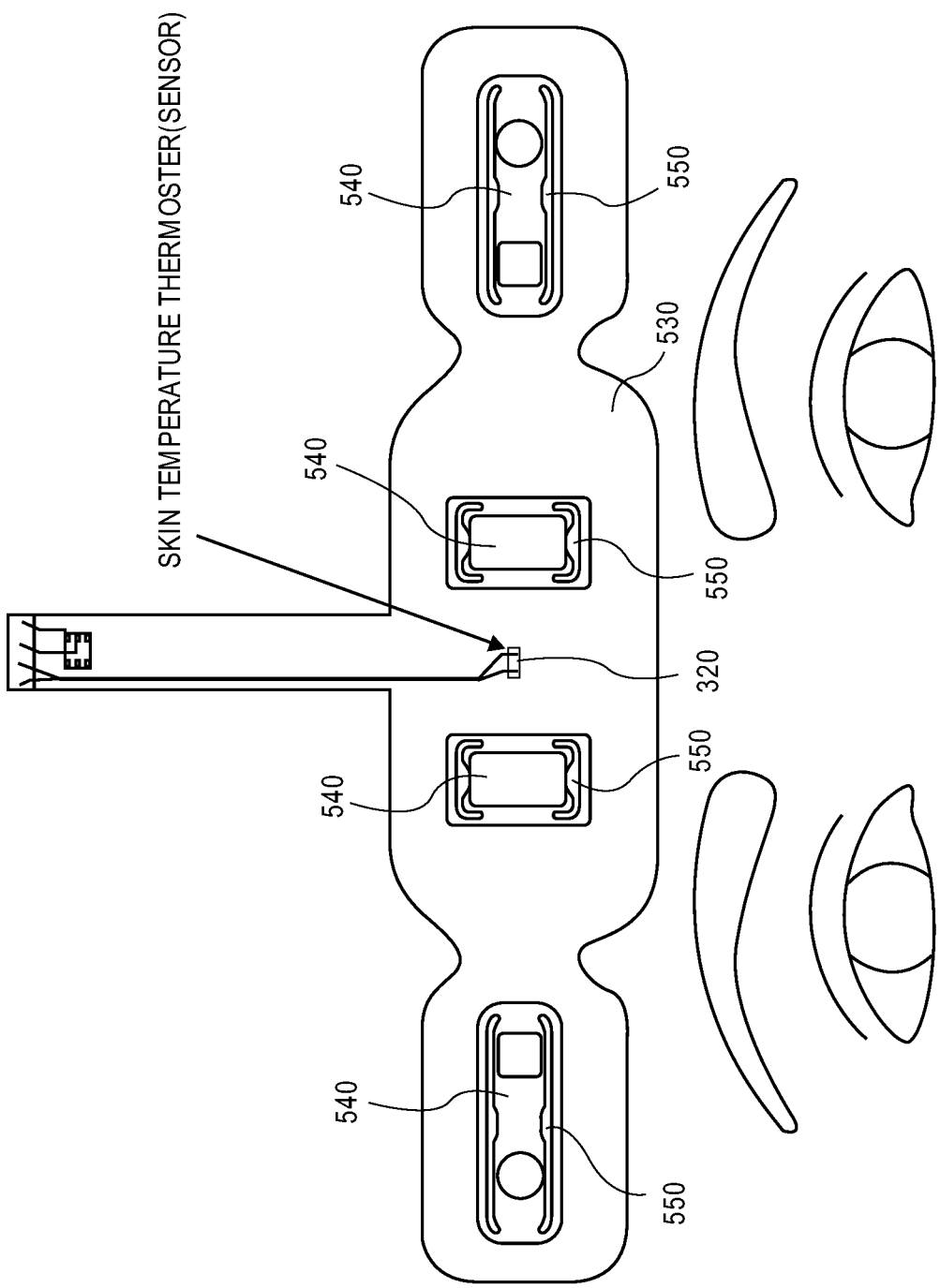

FIGS. 3H, 3I, and 3M, illustrate a temperature sensor 320 associated with the tape of the disposable portion 410 of the sensor 120. In an embodiment, the temperature sensor 320 is a thermistor with the thermistor leads exposed on a patient contacting side of the tape 530, in order to facilitate the contacting of the leads of temperature sensor 320 to a measurement site of a patient's skin. In an embodiment, the temperature sensor 320 is connected to single chip through wires or other suitable electrical connections such as a flexible printed circuit. In an embodiment, the temperature sensor 320 may be located anywhere on the tape 530, the disposable portion 410, or the reusable portion 420 of the sensor. In an embodiment, the leads for the temperature sensor 320 may be near the center of tape 530 or anywhere on the periphery of tape 530.

In an embodiment, the disposable portion 410 of sensor 120 may mate and connect to or overlay the reusable portion 420 of the sensor 120. In an embodiment, the non-patient side of the tape 530 could mate or connect to the reusable portion 420 of the sensor 120 through some suitable adhesive on the tape 530 or some physical connection or mating means. In an embodiment, the disposable portion 410 of the sensor 120 may also contain one or several sensory compartments 540. The sensory compartments 540 may contain a transparent window or a space for the light source 230 or the detectors 260 of the reusable portion 420 of the sensor 120 to emit and detect emitted light through the space or transparent window.

In one embodiment, the light source(s) 230 and detector(s) 260 of the reusable portion 420 may align with the sensory compartments 540 while the reusable 420 and disposable 410 portions physically connect at places other than the sensory compartments 540 and light sources 230 and detectors 260. In an embodiment, the light sources 230 and detectors 260 of the reusable portion 420 of the sensor 120 may physically snap into or somehow removably mate with the sensory compartments 540 of the disposable portion 410 of the sensor 120. In one embodiment, the windows of the sensory compartments 540 may contain certain filters to optimize the wavelengths intensity, or other characteristics of the light that passes through the windows in the sensory compartments 540.

In still other embodiments, care may be taken to ensure sterilization of the reusable components is more straightforward, such as, for example, implementing matable electrical connections through magnetic, optical or other coupling mechanisms that can be mostly or entirely housed in separate housings that are easily sterilized and mostly void of cavities or the like that can trap contamination.

Figure 3N:
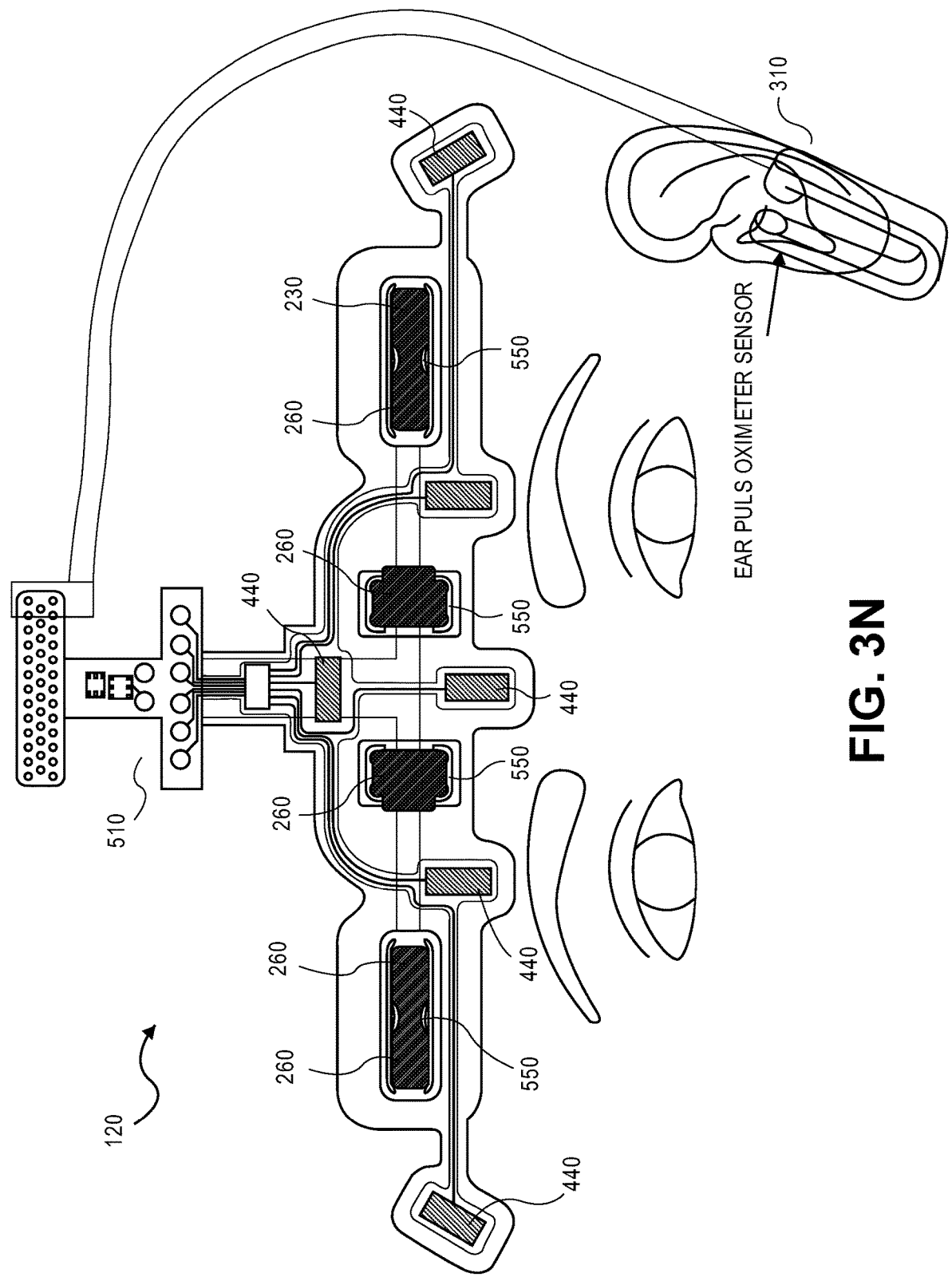

FIGS. 3A, and 3N show an embodiment with the disposable portion 410 of the sensor electrically connected directly to the reusable portion 420 of the sensor 120 through an interface 510. In an embodiment, the interface 510 may be any suitable electrical connection such as a pin connector, a snap in lead connector, an optical connection or an inductance connection.

FIGS. 3H and 3N show an embodiment of the sensor 120 with a pulse oximeter sensor 310 associated with the sensor 120. The pulse oximeter sensor 310 shown in FIGS. 3H and 3N is an ear pulse oximeter sensor 310 that emits and detects radiation to determine the oxygenation of the blood travelling through the arteries of the ear. Many suitable ear pulse oximeter sensors 310 are known in the art such as those sensors commercially available from Masimo Corporation and disclosed herein with reference to U.S. Pat. No. 7,341,599. In another embodiment, the pulse oximeter sensor 310 may be a forehead pulse oximeter sensor 310 or any other suitable pulse oximeter known in the art or disclosed herein. The pulse oximeter sensor 310 may be connected to the sensor through electrical wires, wirelessly or other suitable electrical or data connection. Data collected from the pulse oximeter sensor 310 may be transmitted to the brain oximetry unit 140 or pulse oximeter 150 or both for conditioning, or processing.

FIG. 3G illustrates a multi chip embodiment of the disposable portion 410 of the sensor. In an embodiment, the various EEG electrodes 440 each connect to a separate chip that transmits the detected signal to the interface 510. In an embodiment, the chip transmits the signal to various inductors integrated into interface 510 which transmit the signal to inductors integrated into the reusable portion of the interface 510.

Figure 3O:
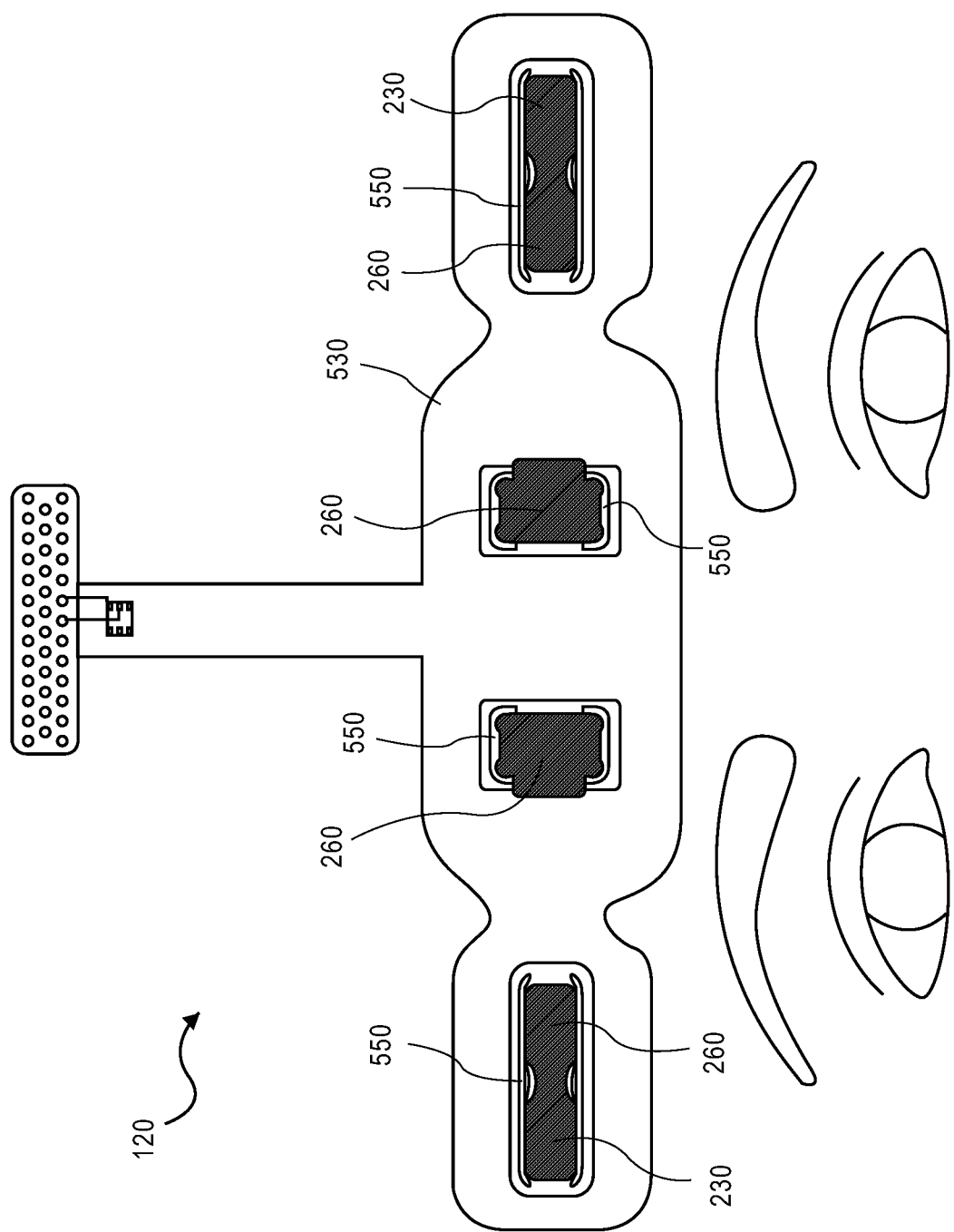

FIGS. 3A, and 3N-3O show the reusable portion 420 of the sensor 120 associated with or physically mated with the disposable portion 410 of the sensor 120. In an embodiment, the reusable 420 and disposable portions 410 of the sensor 120 physically mate at mating sections on the disposable 410 and reusable 420 portions. In one embodiment, the mating sections are located near the light source 230 and detectors 260 on the reusable portion 420 and the sensory compartments 540 on the disposable portion 410. In an embodiment, the mating sections have rims 550 into which cerebral oximeter 300 emitters 230 and detectors 260 may be placed, snapped into or mated. Rims 550 may be any suitable plastic or other flexible material, including metal that would allow the emitter 230 and detector 260 to press or squeeze fit into place. This would allow the rims to physically hold the emitters 230 and detectors 260 in the proper orientation.

Figure 4A:
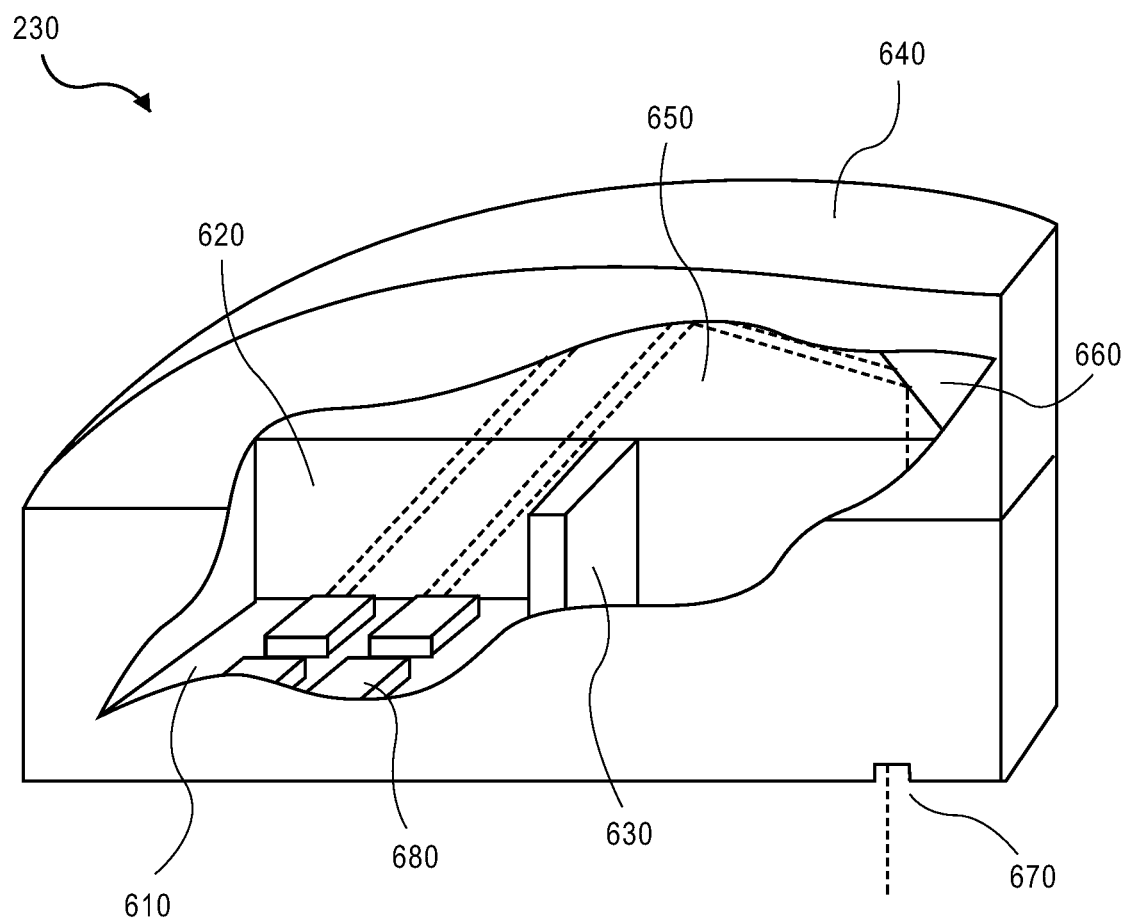
FIGS. 4A-4O illustrate various embodiments and views of light sources of the forehead sensor of FIG. 1A.
Figure 4B:
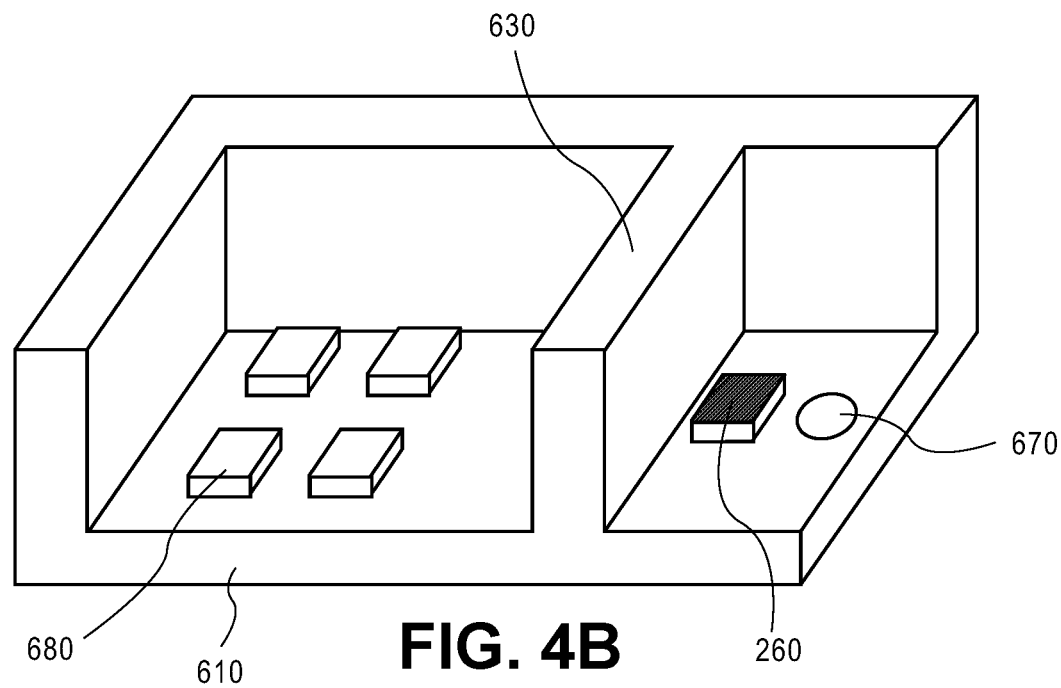
Figure 4C:
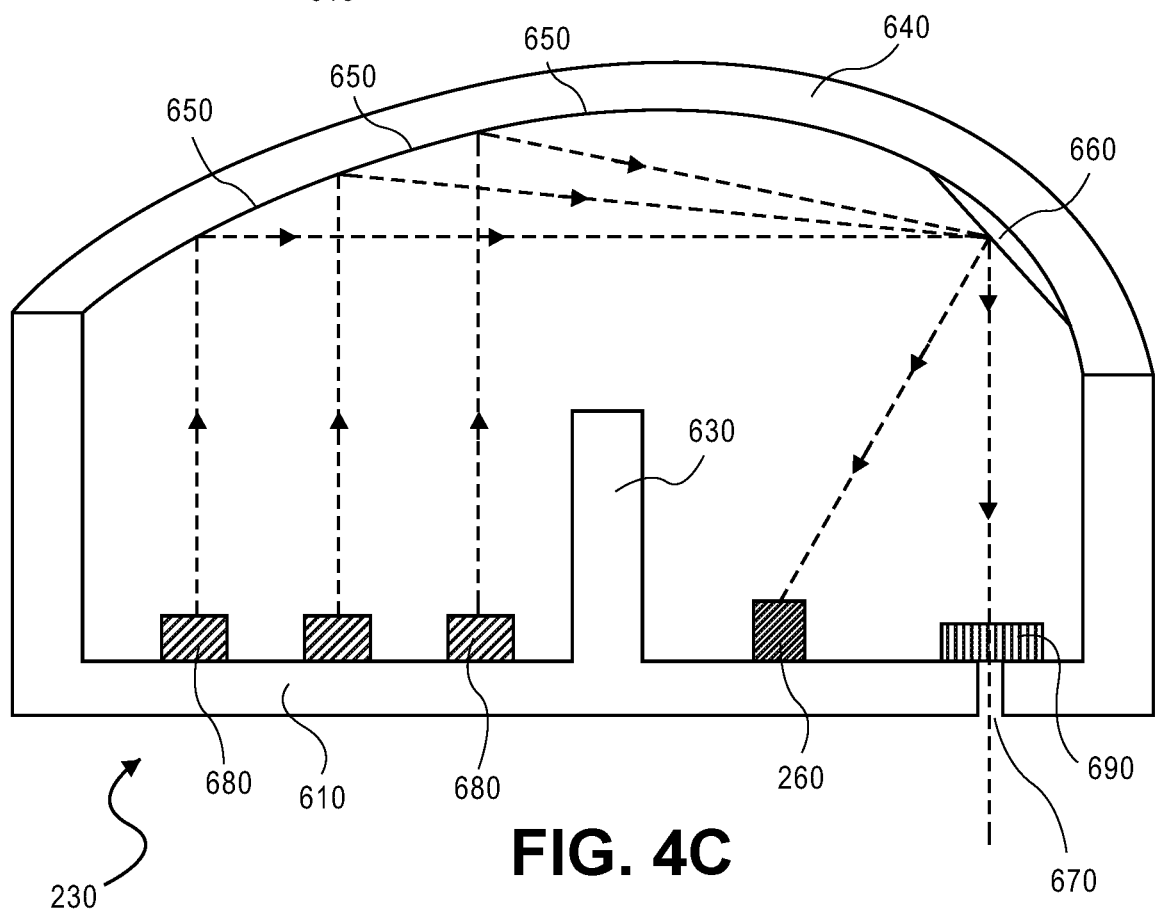
Figure 4D:
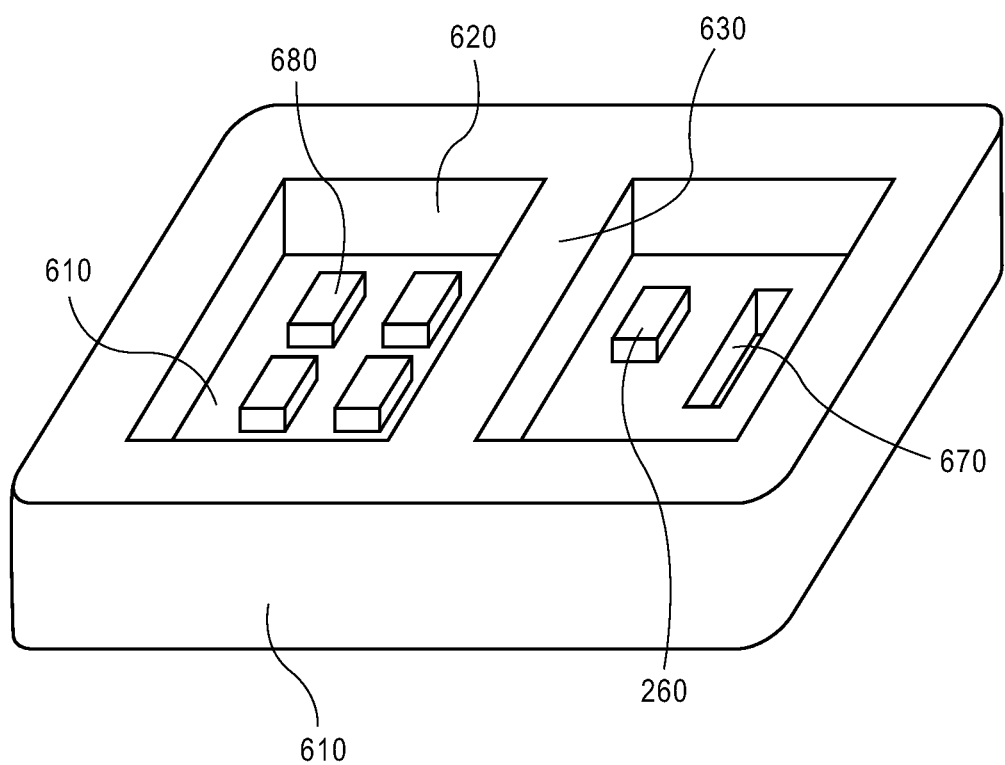
Figure 4E:
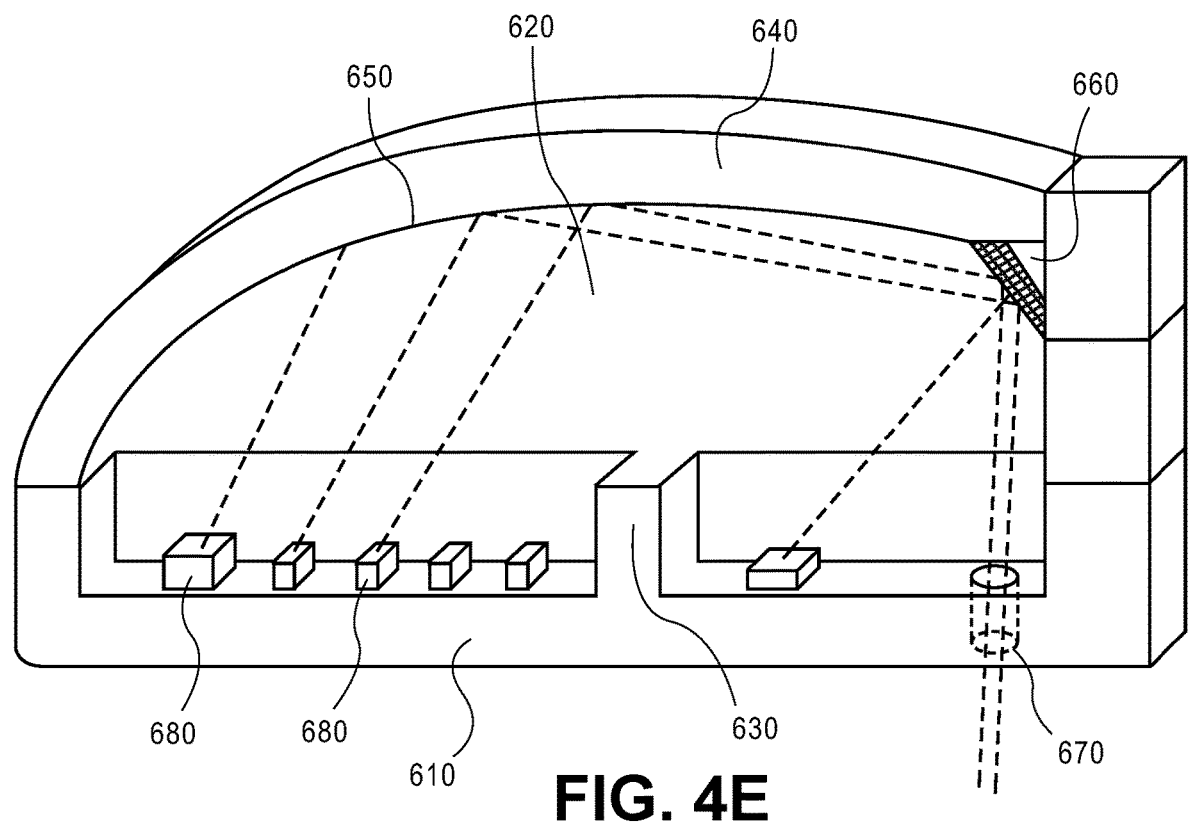
FIG. 4E illustrates a perspective view of the light source including light paths of a multi-faceted directing mirror according to an embodiment of the present disclosure.
Figure 4F:
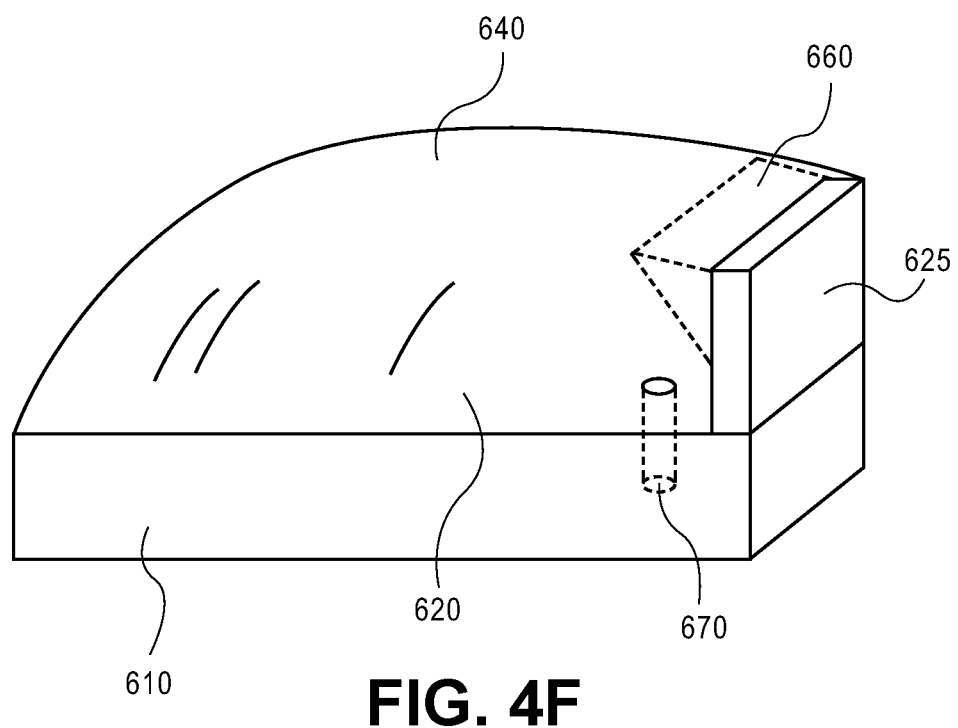
FIG. 4F-G illustrate more perspective views of the light source.
Figure 4G:
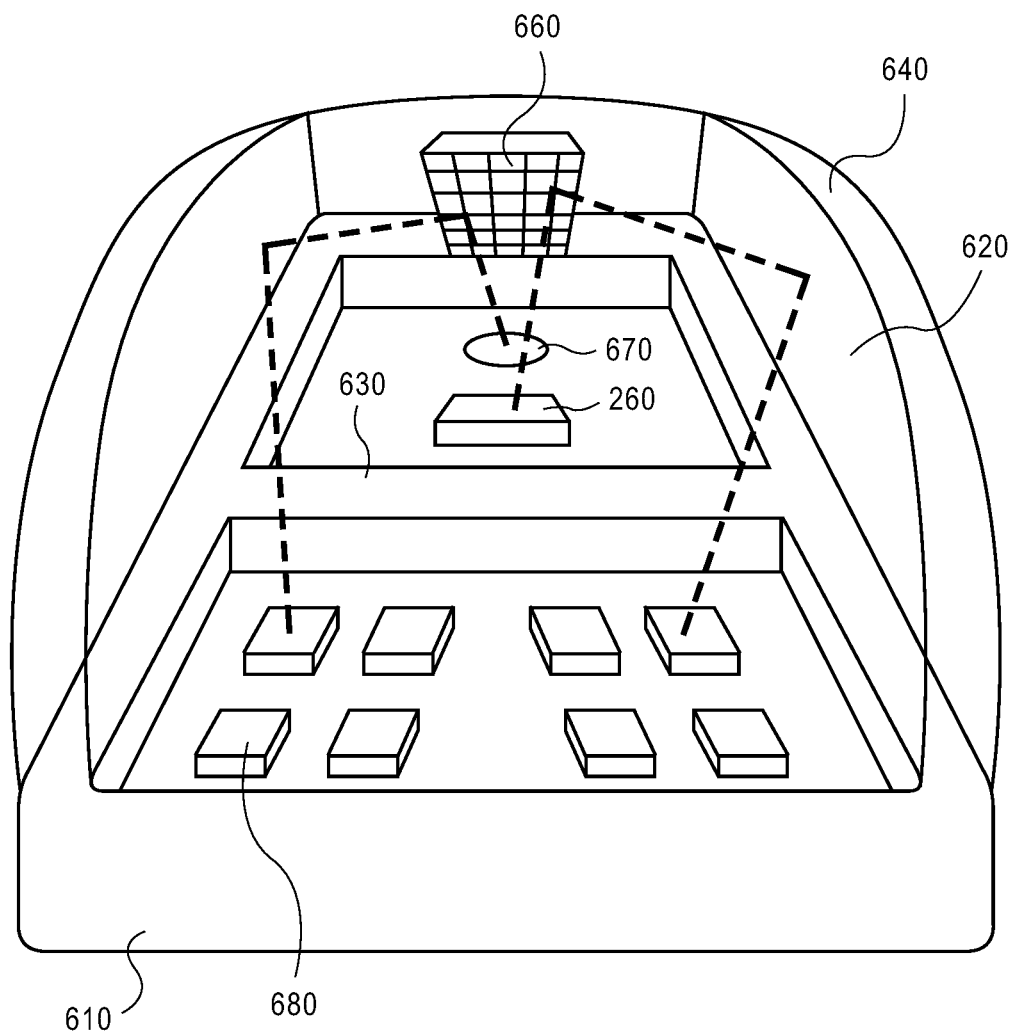
Figure 4H:
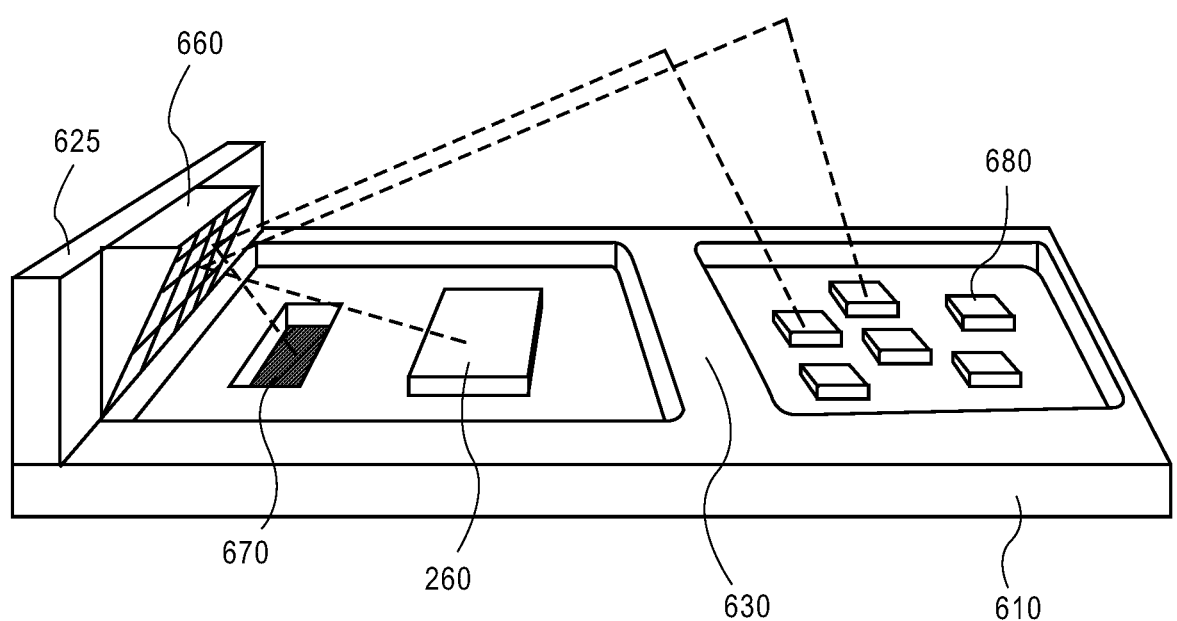
FIG. 4H illustrates a further perspective view of the light source without a cap according to an embodiment of the present disclosure.
Figure 4I:
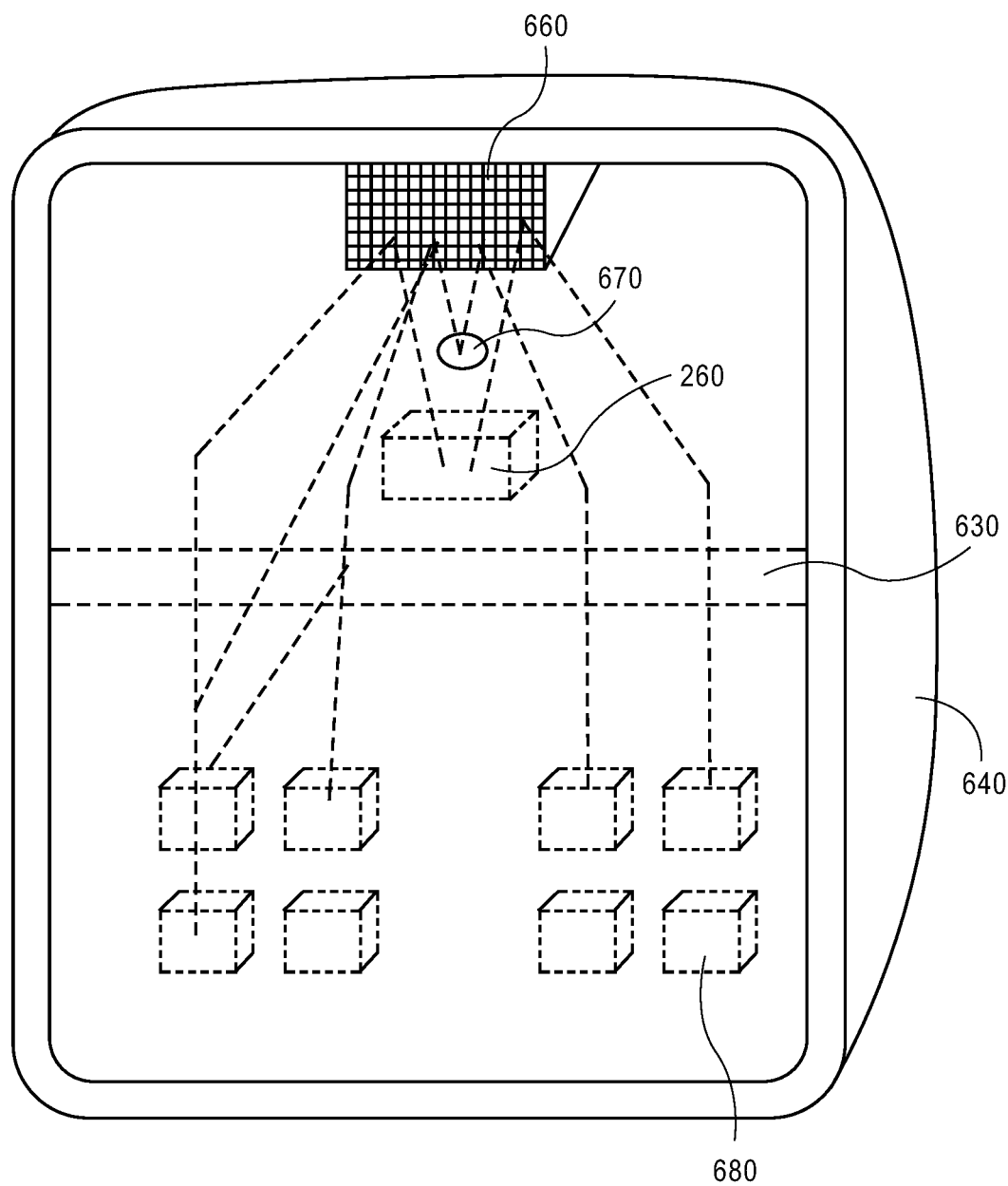
FIG. 4I illustrates a bottom view of the light source towards the top reflective covering according to an embodiment of the present disclosure.
Figure 4J:
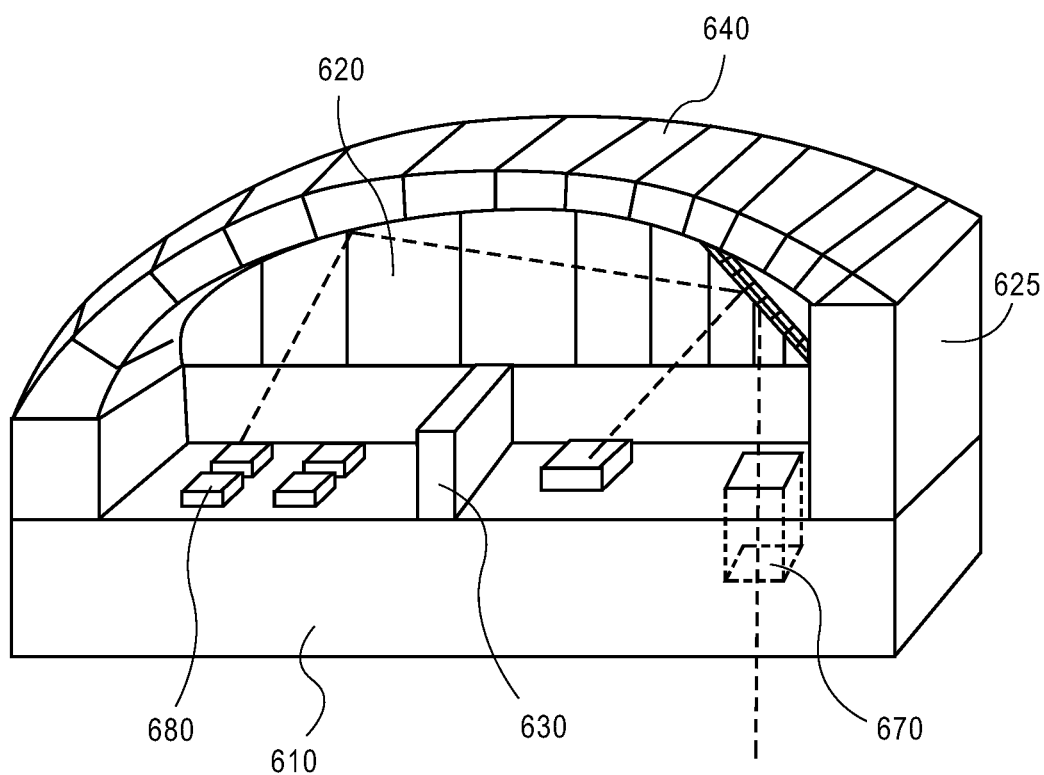
FIG. 4J illustrates a perspective view of the light source with the reflective cover being composed of many portions according to an embodiment of the present disclosure.
Figure 4K:
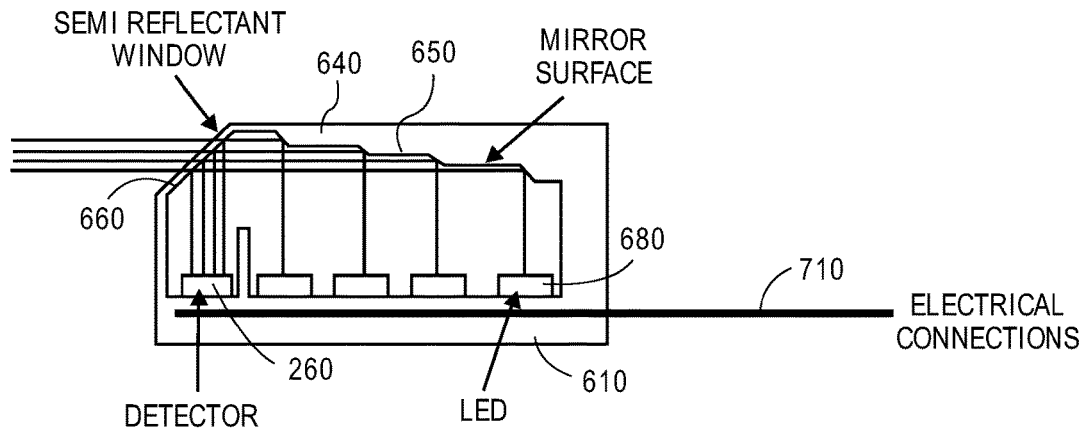
FIGS. 4K-4M illustrate side views of the light source including a semi-reflectant mirror according to an embodiment of the present disclosure.
Figure 4L:
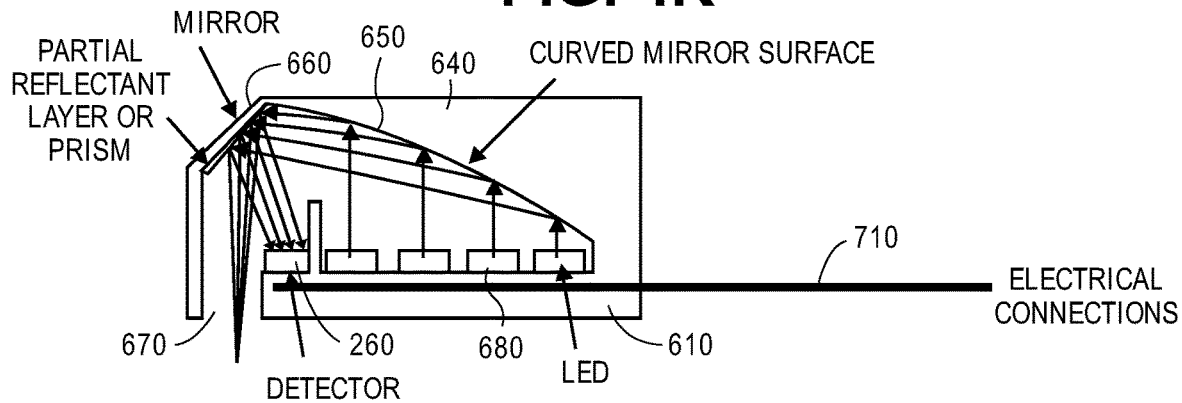
Figure 4M:
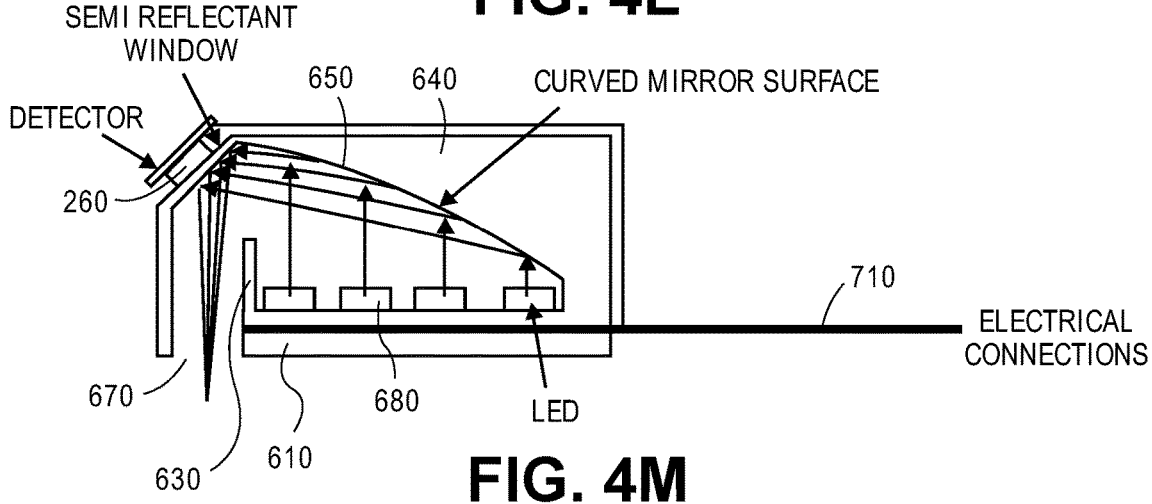
Figure 4N:
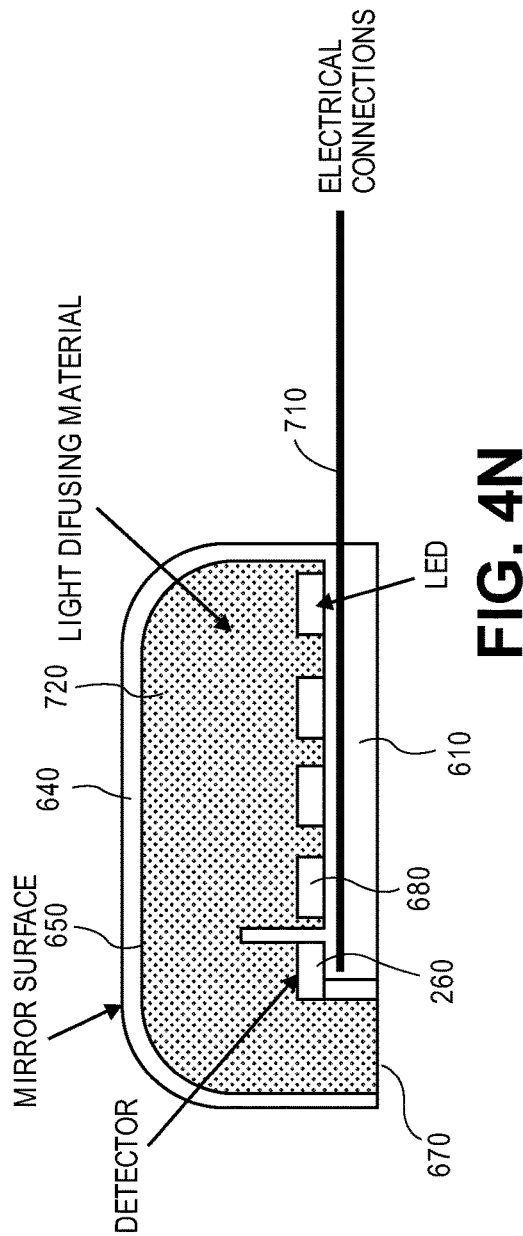
FIG. 4N illustrates a side view of the light source including a light diffusing material filling inside a cap according to an embodiment of the present disclosure.
Figure 4O:
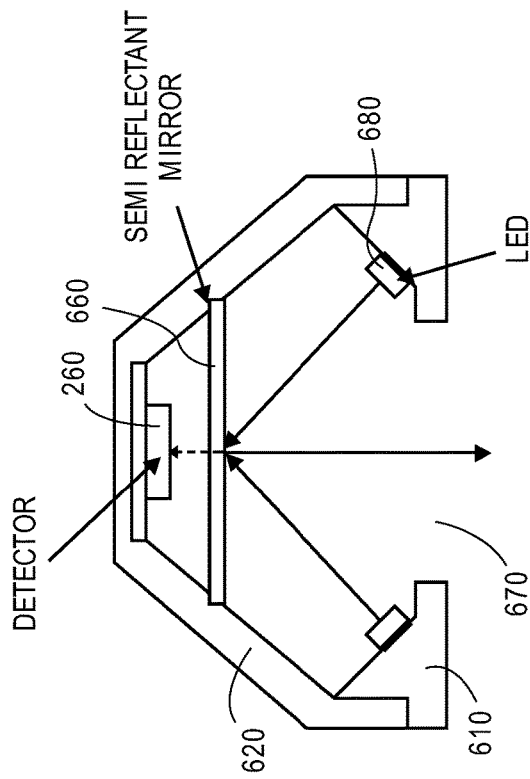

FIGS. 4A-4O illustrate various embodiments of a light source 230 that may be utilized in a cerebral oximeter sensor 300. FIG. 4A shows an embodiment of the light source 230 which includes a substrate 610, guide walls 620, a dividing wall(s) 630, a cap 640, reflective portions 650 on the cap, a splitting mirror 660, and an aperture 670. In an embodiment, the light source 230 includes a substrate 610 to provide a base to associate or attach the remaining components. In an embodiment, the light source 230 includes at least one or a plurality of emitters 680, guide walls 620 attached to the substrate 610, and a dividing wall 630 rising from the substrate 610.

FIG. 4B shows a perspective view of the light source 230 substrate 610 without the cap 640 and one of the guide walls 620, a dividing wall 630, four emitters 680, an emission detector 260 and an aperture 670. In an embodiment, the dividing wall 630 prevents light emitted from the emitters 680 from directly contacting the emission detector 260 or directly exiting through the aperture 670. In an embodiment, the aperture 670 and emission detector 260 may be located anywhere on the side of the dividing wall 630 opposite the side associated with the emitters 680. In one embodiment, the detector 260 is close to the dividing wall 630 and the aperture 670 is spaced further from the dividing wall 630 than emission detector 260. The aperture 670 can be any suitable opening, slot, space, or gap in the substrate 610 of the light source 230, in order to allow at least some of the light reflected from the cap 640 or guide walls 620 to pass through the substrate 610 and exit the light source 230. In an embodiment, the aperture 670 may be a transparent section filled with material that may have optical properties, including a filter or the like.

FIGS. 4C and 4E illustrate an embodiment of the light source 230 with the substrate 610, emitters 680, cap 640, the splitting mirror 660, the dividing wall 630, the emission detector 260, the aperture 670 and the polarizer 690 in light path of the light exiting aperture 670. FIGS. 4C and 4E illustrate an example of one possible embodiment of the variety of potential light paths taken by light emitted from the emitters 680. First, the light is emitted from the emitters 680 and subsequently may be reflected or deflected by the cap 640 towards the splitting mirror 660. Next, as the splitting mirror 660 includes many smaller reflective components that are angled in different directions, a light beam hitting the splitting mirror 660, depending on its cross sectional area, may be broken into multiple beams. The reflective components will be angled either to direct some of the light taking a certain path toward the emission detector 260 and some of the light taking a path leading to the aperture 670 and out of the light source 230. In an embodiment, these smaller reflective components of the splitting mirror 660 may be randomly spaced on the angled mirror to provide an even distribution or sampling of emitted light from the various emitters 680 to both the emission detector 260 and the aperture 670. The cap 640 may have a reflective coating or be made of a reflective material in order to reflect light the emitters toward the splitting mirror 660.

In an embodiment, the cap 640 may have a curvature similar to the curvature illustrated in FIGS. 4A, 4C, 4E-4G, and 4M and also a similar substrate 610, guide walls 620, splitting mirror 660, aperture 670, and emission detector 260 geometry to direct light emitted from the emitters 680 to the emission detector 260 and the aperture 670. This is accomplished by calculating the various angles and light paths of the curvature of the cap, the various angles of the splitting mirror 660, and the reflective components and the various distances between the various components to maintain optimal light paths as described herein.

FIG. 4D shows an embodiment of the substrate 620 without the cap 640. In an embodiment, the substrate 610 can be manufactured by etching out depressions in a block of material to create the guide walls 620, the dividing wall 630, and the depressions for the emitter(s) 230, emission detector 260, and aperture 670. The substrate 610 may be made of any suitable material. In one embodiment, the substrate 610 is made from a material that provides an even distribution of temperature such as a ceramic material. FIG. 4F shows an outside view of the light source 230 with dotted lines representing the splitting mirror 660 and the aperture 670 associated with the substrate 610 of the light source 230. In an embodiment, the cap 640 includes back guide wall 625 attached to the cap 640, the substrate 610, and the splitting mirror 660.

FIGS. 4G and 4H, and 4I show embodiments of the light source 230 from different perspectives. In an embodiment, the cap 640 is supported at least in part by the guide walls 620 that extend down from the cap 640 to the substrate 610. In an embodiment, the cap 640 is dome shaped. FIG. 4I illustrates a light source 260 with eight emitters 680. Also shown is an embodiment of the splitting mirror 660 with several different directing reflecting surfaces positioned in different orientations to angle the light rays either toward the aperture 670 or the emission detector 260. FIG. 4H shows the splitting mirror 660 as viewed from below the substrate 610. The dotted lines represent the outline of the cap 640, the aperture 670, and the emission detector 260.

FIGS. 4J and 4K illustrate an embodiment of the cap 640 that is divided into different sections, with each section tilted at a predetermined angle to facilitate directing of the light paths from light emitted from the emitter(s) 680 to be directed toward the splitting mirror 660 which would then direct the light to the emission detector 260 or the aperture 670. In an embodiment, the sections of the cap 640 may be arced to form the guide walls 620. Also, the cap 640 may include straight segments that are attached to the guide walls 620. In an embodiment, the splitting mirror 660 may be formed in the cap 640, be the material of the cap 640, be fastened to the cap 640, partially to the cap 640, to the guide walls 620 or to the substrate 610 or any combination thereof.

FIG. 4K illustrates the aperture 670 in the form of a semi-reflectant splitting mirror 660 that allows some of the light to pass through the mirror 660 and reflects the rest of the light to emission detector 260. In this embodiment, the aperture is behind the splitting mirror 660.

FIG. 4L illustrates an embodiment of the light source 230 with a splitting mirror 660 that includes both a semi-reflectant component and a completely or more strongly reflective component. In one embodiment, the splitting mirror 660 includes a first semi-reflectant mirror positioned at a first angle that reflects a portion of the emitted light to the emission detector 260 or the aperture 670. The second reflective surface reflects the remaining light toward the aperture 670 or the emission detector 260, and in an embodiment, to the opposite of the two components that the first reflective surface direct the light.

FIGS. 4K-4M also illustrate electrical connections 710 that power the emitters 680 and receive data from the emission detector 260 and are associated with or printed on the side of the substrate 610 or other components of the light source 260. These electrical connections 710 can be any suitable electrical connection and may be printed on any component of the light source 230 including the inside or outside of the cap 640.

FIG. 4M illustrates an embodiment with light source 230 that includes a semi-reflectant mirror 660 with the emission detector 260 located behind the semi-reflectant mirror 660. In this embodiment, the emission detector 260 samples light that passes through the semi-reflectant mirror 660 and the aperture 670 emits light that is reflected from the semi-reflectant mirror 660.

FIG. 4N illustrates an embodiment of the light source 230 where at least a part of the space defined by the cap 640, the substrate 610 and the guide walls 620 are filled with light diffusing material 720. The light diffusing material 720 could be any suitable light diffusing material 720 known in the art including an epoxy or other plastic material, fiber optics, any epoxy mixed with beads or other materials. In an embodiment, the light diffusing material 720 may cause the light emitted from the emitters 680 to become increasingly evenly distributed in the domains of at least range and intensity, as the path length of the light emitted from the emitter(s) 680 increases. In an embodiment, the light diffusing material 720 will more evenly distribute the intensity and range of the light that is incident on the emission detector 260 and the light exiting the light source through the aperture 670.

FIG. 4O illustrates another embodiment of the light source 230 with emitters 680 on far sides of the substrate 610 and angled towards a semi reflectant mirror 660 attached to the cap 640 or guide walls 620. In this embodiment, when the light is emitted onto the semi-reflectant mirror 660, some of the rays will pass directly through the semi-reflectant mirror 660 and be detected by the emission detector 260. The other rays that do not pass directly through semi-reflectant mirror 660 will be reflected. A portion of the reflected rays that have the appropriate incident angle on the semi-reflectant mirror 660 will exit the light source 230 through the aperture 670 after reflecting off the semi-reflectant mirror 660.

Figure 4P:
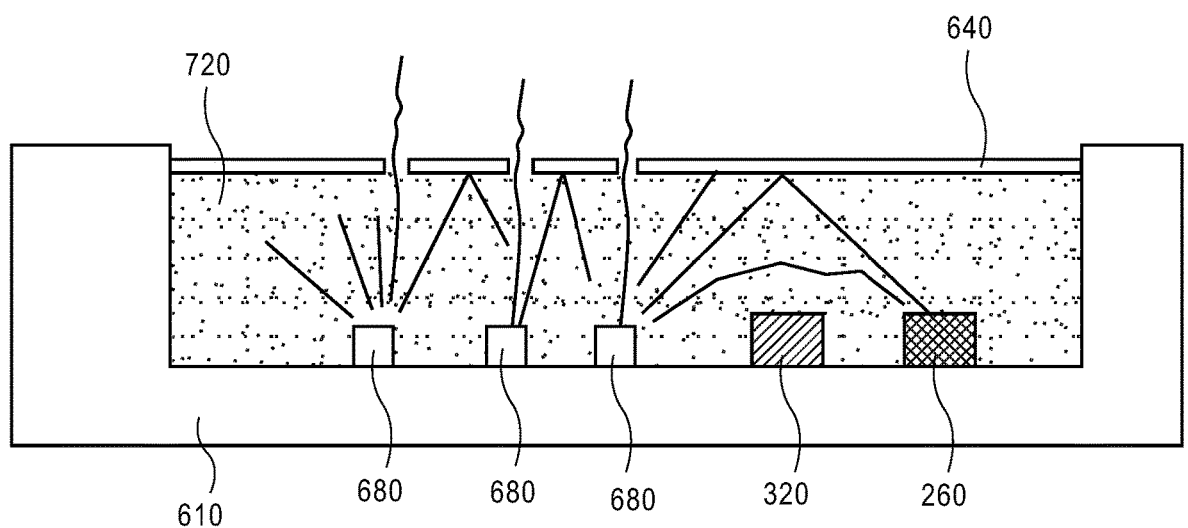
FIG. 4P illustrates a side view of the light source with a relatively flat cap.

FIG. 4P illustrates another embodiment of the light source 230 that may not require splitting mirror 660. In this embodiment, light rays are instead directed to the detector 260 and the apertures 670 by the diffusion and scattering of the light through light diffusing material 720. The light diffusing material 720 may be any suitable diffuser for dispersing light throughout the inside of the light source 230 including glass, epoxy fill, glass beads, plastic, and any other diffuser, scatterer, mixer or combination known in the art. The light diffusing material 720 may be filled in around emitters 680 or may be a component in front of or around the emitters 680.

Additionally the cap 640 may reflect light diffused throughout the cavity back towards detector 260. The cap 640 may be reflective or non-reflective. In an embodiment, the cap 640 absorbs light so that the detector 260 senses light that has passed through the diffuser and has not reflected off the cap 260, so that it will be similar in quality, for example, intensity, to the light emitted through the apertures 670. The cap 640 may be made of a suitable metal including, for example, copper and/or gold. In an embodiment, the cap 640 is relatively straight and does not have a rounded profile in order to reduce the cost and complexity of manufacturing and reduce the bulkiness of the light source 230. This is advantageous as a bulkier, larger sensor will add weight and make the sensor 120 more cumbersome on a patient's forehead.

In this embodiment, the apertures 670 may be directly above the emitters 680 or to the left and right of the emitters 680 so that the emitters will emit light directly outside the aperture 670 and most of the light will not have been reflected off of the cap 640 or other inside surfaces of the light source 230 before exiting the light source 230. This will provide for simpler construction of the light source 230 and other advantages.

The emitters 680 in an embodiment, may be LEDs, or any other suitable light emitting device known in the art. Also, in an embodiment, the temperature sensor 320 will provide feedback for regulating the intensity of the emitters 680 in addition to the information obtained from the detector 260 inside light source 230. The operator, therefore, will be able to maintain and determine an accurate intensity for the emitters 680, leading to more accurate results when processing the signals detected by the detectors 260 of the brain oxygenation sensor 300. In an embodiment, the embodiments disclosed with reference to FIG. 4 comprise an optical bench whose manufacturing costs are significantly lower than those available to design manufacturers today. Diffusing, scattering, reflecting or mixing material, or combinations thereof, may advantageously be used to integrate emitted light, thereby providing an optical bench from comparatively low cost manufacturing materials.

Figure 5:
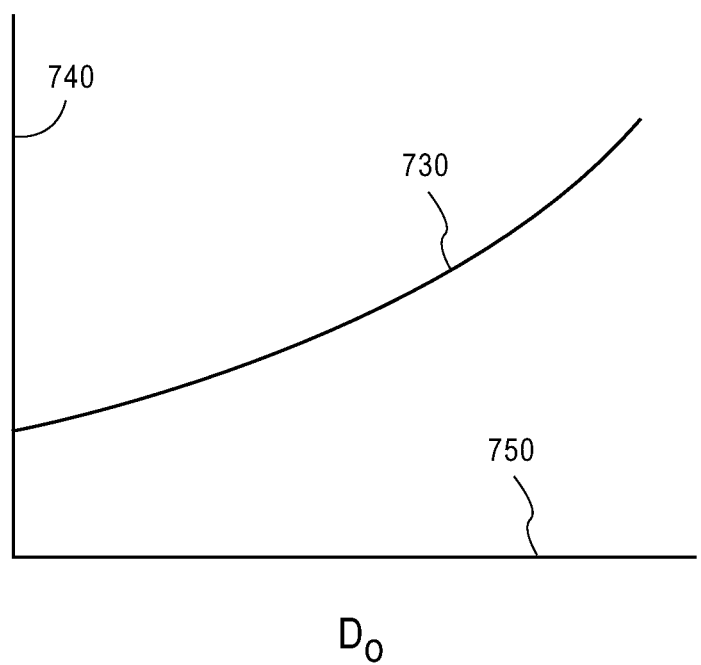
FIG. 5 illustrates an exemplary graph showing the calibrated relationship of the emission detector output to the calibrated intensity of the emitter output according to an embodiment of the present disclosure.

FIG. 5 illustrates an embodiment of the calibration curve 730 used to determine the intensity of the light emitted from the light source 230 though the aperture 670. In one embodiment, the intensity 740 of the emitted light is mapped with respect to the output 750 of the emission detector 260 of the light source 230. Measuring the output of emission detector 260 will allow the patient monitoring system 100 to calculate a close approximation of the intensity 740 of light being simultaneously emitted from the light source 230 through the aperture 670.

Figure 6:
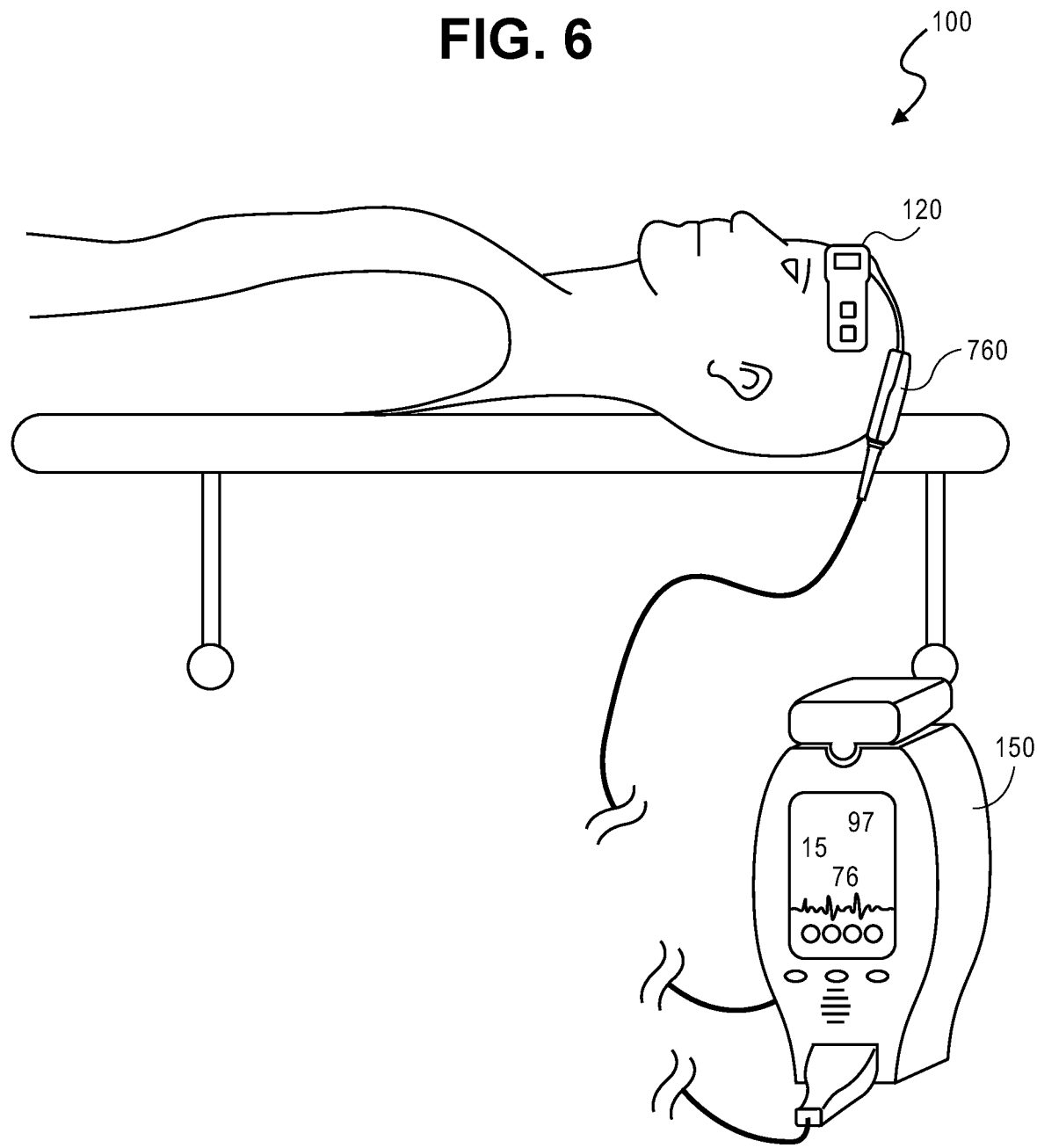
FIG. 6 illustrates an embodiment of a forehead sensor communicating with a brain oximetry unit contained inside a connector, which in turn communicates with a pulse oximeter configured to monitor and/or display a state of consciousness through brain oxygenation.

FIG. 6 illustrates another embodiment of the patient monitoring system that incorporates that brain oximetry unit 140 into a connector 760 for the sensor 120. This advantageously allows for a streamlined profile and reduced manufacturing costs of the brain oximetry unit 140 and associated wires. In this embodiment, the circuitry for driving the front end and controlling the drive signal of the brain oxygenation sensor 300 may be in the brain oximetry unit 140 which may advantageously be partially or entirely housed by the connector 760, or may advantageously be partially or entirely housed by the pulse oximeter 150 or other multi-parameter patient monitor. Additionally, the circuitry for processing the signals detected by the detectors 260 of brain oxygenation sensor 300 may also be partially or entirely housed by the connector 760.

In an embodiment, the connector 760 may also house various other components that control and process the signals from various sensors associated with a patient monitoring system 100. For example, the connector 760 may house the circuitry for a blood oxygenation sensor 310 in, for example, an embodiment where the sensor 120 incorporates an ear blood oxygenation sensor or other blood oxygenation sensor 310. In another embodiment, the circuitry for processing, detecting and/or driving the signals for the temperature sensor 320, or EEG sensor 330 may advantageously be incorporated into the sensor connector 760.

Also, the signal processing and conditioning circuitry processor for a patient sedation monitor capable of monitoring the EEG signals of a patient and providing feedback on the depth of sedation or awareness of a patient undergoing anesthesia may be partially or entirely incorporated into the connector. Sedation brain function monitors, including those similar to the SEDLine sedation monitor commercially available from Masimo Corporation of Irvine, Calif., and disclosed herein with reference to U.S. Pat. Nos. 6,128,521, 6,301,493, 6,317,627, 6,430,437, among others assigned to Masimo Corporation. The connector 760 may house the circuit board, with six channels for six detectors and the SEDLine algorithm. In this embodiment, a conventional pulse oximeter may include upgraded programming to recognize the connection of a brain oximetry unit 140, whether separate or housed inside connector 760, and provide communication and power to the unit 140. The unit 140 performs the processing and other functionality for the sensor 120, including storing various algorithms for the associated sensors 120.

Integration of all or the majority of the associated circuitry and processing components of several different patient monitoring sensors 120 in a single connector 760 advantageously provides a caregiver a simple device that can be attached to the patient's forehead or other areas on the patient, to provide minimal discomfort to the patient and minimal amount of wires and connections to cause electrical interference with instruments in the hospital environment. Additionally, the caregiver will need to spend less time hooking various sensors to a patient where each would otherwise require its own associated monitoring station. Furthermore, this integration of sensor 120 processing components allows some of the processing components to have shared functionality and therefore saves considerably on manufacturing costs. For example, memory chips, processors, or other electrical components may be shared by the various sensors in the connector 760.

FIGS. 7-13 illustrate various embodiments of the construction of the sensor 120. FIGS. 7A-7E illustrate an embodiment of the sensor without the EEG sensor 330 incorporated and includes the disposable portion 410, reusable portion 420, interface 510, connector 760, sensor compartments 540, light sources 230 and detectors 260. The part of the interface 510 on the disposable portion 410 slides into the interface 510 on the reusable portion 420. The interface 510 on the reusable portion 420 may be integrated into the connector 760 or may be separate and located elsewhere on the body of the sensor. In an embodiment, the interface 510 on the disposable portion 410 may slide into the interface 510 on the reusable portion 420 and lock or be somehow be held into place until it needs to be removed.

The interface 510 may include an EEPROM or other memory device from an authorized manufacturer in order to provide quality control. Also, the interface 510 may also include software programming or functionality for determining how many uses it has gone through, how many times it has been used or applied to a patient, or the date of manufacture to determine if it has expired. Also, the interface 510 may include an EEPROM for storing information unique to the electrodes that can be read by the patient monitoring system 100 or pulse oximeter 150. The pulse oximeter 150 or patient monitoring system 100 can then determine how many electrodes are contained on the disposable portion 410, for example, and other information.

FIG. 7E illustrates the placement of the light sources 230 and the detectors 260 for the brain oxygenation sensor 300. The light source 230 may be at the outer end of the sensor 120 and emits light into the cerebral cavity of a patient. The two detectors 260 closest to each light source 230 detect light emitted from the light source 230. For example, the right side light source 230 emits light into the head of a patient and some of the light is returned to the detector 260 closest to the light source 230 and some returns to the detector that is just to the right of the center of the sensor 120. The path that the light travels through the head of a patient to the closer detector generally does not enter the cerebral cavity and travels as deep as the skull. The light path taken by light detected by the further detector 260 generally enters the cerebral cavity. In an embodiment, the signal from the first detector 260 can be subtracted from the second detector 260 in order to provide the information necessary to calculate the cerebral oxygenation as disclosed herein.

FIGS. 8A-8D illustrate an embodiment of the sensor 120 with the EEG sensor 330 integrated into the sensor 120. In this embodiment, the disposable portion includes the EEG electrodes 440, which are electrically connected to the connector 760 through wires integrated into the body of the disposable portion 410. In another embodiment, the disposable portion 410 includes the EEG electrodes 440 for electrical contact with a patient's skin. In this embodiment, the disposable portion may not include any wiring except for electrically connecting the EEG electrodes 440 to the reusable portion 420.

FIGS. 9A-9E illustrate an embodiment of the reusable portion 420 that allows the reusable portion to be disconnected from connector 760. In other embodiments, the reusable portion 430 may be permanently connected to the connector 760. In an embodiment, the reusable portion 420 may be more difficult to disconnect from connector 760 than the disposable portion 410, and may require the operator to open or disassemble at least a part of connector 760.

FIG. 9E illustrates an embodiment of the reusable portion 420 with light sources 230 and detectors 260 some or all of which may take advantage of several features to allow light piping. In an embodiment, the detectors 260 and light sources 230 may have a raised lip 800 that contacts the skin to create a barrier that prevents light from escaping from the light source 230 or detector 260 to the ambient. In an embodiment, the raised lip 800 may be black and absorbent, or reflective. The light sources 230 and detectors 260 may also have a valley or depression on the glass or other transparent or near transparent parts that increases in depth towards the middle of the component. This valley or depression will also advantageously assist with light piping as greater and firmer contact will be made around the edge of the light source 230 or detector 260 allowing less light to escape to the ambient from the light source 230 or emanating from the skin to the detector 230.

FIGS. 10A-10D illustrate various embodiments of the reusable portion 420 of the sensor 120. In an embodiment, the reusable portion 420 has multiple layers that are overlaid and connected together. In an embodiment, the layers include a top flexible sleeve 810, a flex circuit support 820, a flex circuit 830 and a bottom flexible sleeve 840. In an embodiment, the top and bottom flex circuit sleeves 810, 840, may be bonded together or connected together either at the edges or through other means known in the art with the flex circuit support 820 and flex circuit 830 inside and in-between. The top flexible sleeve 810 may be made of silicone or another suitable material and may be white or another color. The bottom flexible sleeve 840 may be made from silicon or other material and may be black. The flex circuit support 820 may be made from cyrlex, polyester or another suitable material and provides support for flex circuit 830. Flex circuit 830 may include EEPROM(s), the flexible circuit, the light sources 230 and detectors 260 for the brain oxygenation sensor 300 and the interface 510. The bottom sleeve includes recesses 850 for the light sources 230, detectors 260 and temperature sensor 320.

FIGS. 11A-11E illustrate an embodiment of the connector 760. The connector 760, in this embodiment, includes a housing 860 that houses the components of the connector 760, including for example, printed circuit boards 870 for various functions, such as, for example, SEDLine monitoring, brain oximetry, pulse oximetry, other blood parameter or physiological parameter calculators, combinations of the same or the like. The connector 760 also includes the interface 510 for the disposable portion 410 and reusable portion 420. The interface 510 in the connector 760 includes a slot 880 for interface 510 on the disposable portion 410.

FIGS. 12A-12D illustrate an embodiment of the disposable portion 410 that does not include the components for the EEG sensor 330 but includes the components for the brain oxygenation sensor 300. In this embodiment, the sensor 120 includes the sensory compartments 540 and the interface 510 which may include an EEPROM for security. In an embodiment, the disposable portion 410 includes an adhesive layer 890 that includes a layer of adhesive and a base material to attach the adhesive layer to the main body of the disposable portion 410. The adhesive layer 890 includes the adhesive for attaching the sensor 120 to the patient's skin. In an embodiment, where the disposable portion 410 does not have the EEG sensor 330 components, the disposable portion 410 will not contain any wires or any other electrical components allowing it to be inexpensively manufactured.

FIGS. 13A-13D illustrate an embodiment of the disposable portion 410 that includes the EEG sensor 330 components. In this embodiment, the disposable portion has the EEG electrodes 440 and wiring for the EEG electrodes 440. The EEG electrodes 440 may include pads 900 for contact with the patient's skin. The pads 900 fit into openings 910 in the adhesive layer 890 in order to make direct contact with the skin.

Figure 14:
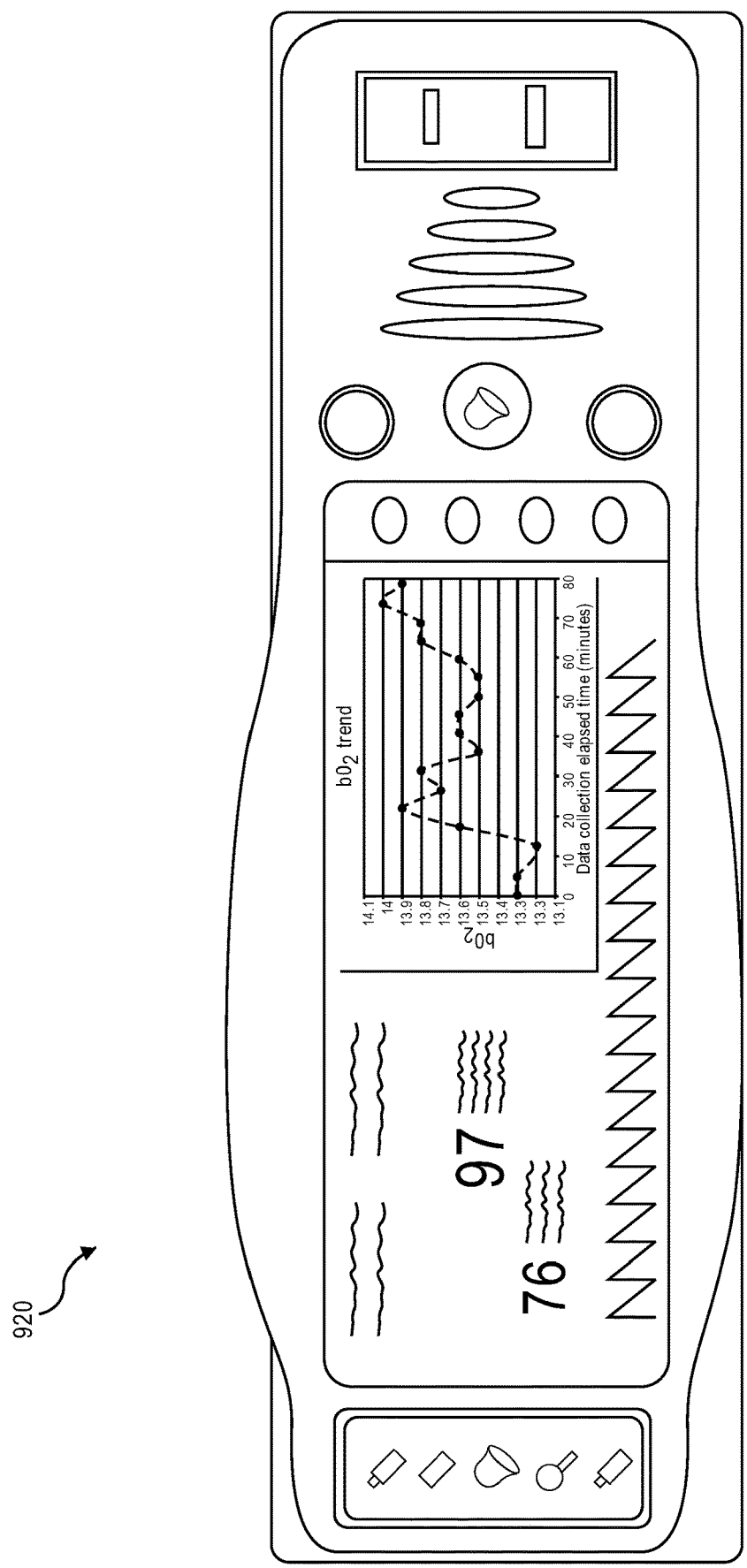
FIG. 14 illustrates an embodiment of an exemplary display showing potential brain oximetry parameters that could be displayed in an embodiment of the brain oximetry sensor.

FIG. 14 illustrates an example of a display 920 that may be utilized for the sensor 120. Shown is the brain oxygenation level ($bO_2$), the heart rate, blood oxygenation, and the sedation level from the SEDLine brain function monitor. As other sensors have been described or could be integrated into the sensor 120 additional parameters may be shown on the display 920.

Although the foregoing disclosure has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present disclosure is not intended to be limited by the reaction of the preferred embodiments, but is to be defined by reference to the appended claims.

Additionally, all publications, patents, and patent applications mentioned in this specification are herein incorporated by reference to the same extent as if each individual publication, patent, or patent application was specifically and individually indicated to be incorporated by reference.

What is claimed is:

1. A sensor assembly comprising:
    a reusable portion that comprises a temperature sensor including a lead, a first emitter, and a second emitter; and
    a disposable portion that is removably connectable to the reusable portion, said disposable portion comprising an adhesive tape configured to secure the disposable portion to a skin of a patient, wherein the adhesive tape comprises an opening that is aligned with respect to a position of the lead on the reusable portion, said opening further configured to receive the lead and expose the lead for contacting a measurement site on the skin of the patient,
    wherein the temperature sensor is positioned in between the first emitter and the second emitter.

2. The sensor assembly of claim 1, wherein the temperature sensor comprises a thermistor.

3. The sensor assembly of claim 1, wherein the reusable portion further comprises a brain oxygenation sensor.

4. The sensor assembly of claim 1, further comprising a connector configured to house electronics for processing sensor data.

5. The sensor assembly of claim 1, wherein the reusable portion comprises circuitry for wireless transmission of sensor data.

6. The sensor assembly of claim 1, wherein the reusable portion and disposable portion are flexible.

7. A patient monitoring system, said patient monitoring system comprising a sensor assembly according to claim 1, wherein the patient monitoring system further comprises a first detector corresponding to the first emitter and a second detector corresponding to the second emitter.

8. The sensor assembly of claim 1, wherein the disposable portion includes a plurality of electrodes.

* * * * *